United States Patent
Toutov et al.

(10) Patent No.: US 11,104,693 B2
(45) Date of Patent: Aug. 31, 2021

(54) HYDROXIDE-CATALYZED FORMATION OF SILICON-OXYGEN BONDS BY DEHYDROGENATIVE COUPLING OF HYDROSILANES AND ALCOHOLS

(71) Applicant: California Institute Of Technology, Pasadena, CA (US)

(72) Inventors: Anton Toutov, Pasadena, CA (US); Kerry Betz, Boulder, CO (US); Andrew M. Romine, Kennett Square, PA (US); Robert H. Grubbs, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 16/384,178

(22) Filed: Apr. 15, 2019

(65) Prior Publication Data

US 2019/0241587 A1 Aug. 8, 2019

Related U.S. Application Data

(62) Division of application No. 15/219,710, filed on Jul. 26, 2016, now Pat. No. 10,259,831.

(60) Provisional application No. 62/198,405, filed on Jul. 29, 2015, provisional application No. 62/269,746, filed on Dec. 18, 2015.

(51) Int. Cl.
| | | |
|---|---|---|
| C07F 7/21 | (2006.01) | |
| C07D 235/08 | (2006.01) | |
| C07F 7/18 | (2006.01) | |
| C07F 7/08 | (2006.01) | |

(52) U.S. Cl.
CPC .......... *C07F 7/1804* (2013.01); *C07D 235/08* (2013.01); *C07F 7/0896* (2013.01); *C07F 7/21* (2013.01)

(58) Field of Classification Search
CPC ...... C07F 7/1844; C07F 7/1868; C07F 7/184; C07F 7/21; C07D 235/08
USPC ................................................ 548/110, 406
See application file for complete search history.

(56) References Cited

FOREIGN PATENT DOCUMENTS

| | | |
|---|---|---|
| CN | 1542014 A | 11/2004 |
| CN | 1814602 A | 8/2006 |
| CN | 101070380 A | 11/2007 |
| GB | 1007028 A | 10/1965 |
| WO | 2014/055587 A1 | 4/2014 |

OTHER PUBLICATIONS

Grajewska, A. and M. Oestreich, "Base-catalyzed dehydrogenative Si—O coupling of dihydrosilanes: silylene protection of diols", Synlett 2010, 16: pp. 2482-2484. (Year: 2010).*
Koike, T. and A. Mori, "Palladium-catalyzed cross-coupling reaction of silicone with aryl chlorides", Synlett 2003, 12: pp. 1850-1852. (Year: 2003).*
Huang, C., N. Ghavtadze, B. Chattopadhyay and V. Gevorgyan, "Synthesis of catechols from phenols via pd-catalyzed silanol-directed C—H oxygenation", J. Am. Chem. Soc. 2011, 133: p. S1-S42 (supplemental information). (Year: 2011).*
Fernández-Salas, J., S. Manzini and S. Nolan, "Facile and efficient KOH-catalysed reduction of esters and tertiary amides", Chem. Commun., 2013, 49, pp. 9758-9760. (Year: 2013).*
Fernández-Salas, J., S. Manzini and S. Nolan, "Facile and efficient KOH-catalysed reduction of esters and tertiary amides", Chem. Commun., 2013, 49, pp. 9758-9760 (Supplemental information). (Year: 2013).*
Anastas et al., "Origins, Current Status, and Future Challenges of Green Chemistry", Acc. Chem. Res., Jun. 2002, 35(9), 686-694.
Azizi, N. et al., "Novel and Efficient Method for the Silylation of Hydroxyl Groups with Hexamethyldisilazane (HMDS) under Solvent-Free and Neutral Conditions", Organometallics, 2004, vol. 23, No. 6, pp. 1457-1458 (Epub. Nov. 8, 2003).
Bedard et al., "Conversion of hydrosilanes to alkoxysilanes catalyzed by Cp2TiCl2/n Buli", Journal of Organometallic Chemistry, May 1992, 428(3), 315-333.
Berger et al., "Toward a Versatile Allylation Reagent: Practical, Enantioselective Allylation of Acylhydrazones Using Strained Silacycles", J. Am. Chem. Soc., 2003, 125, 9596-9597.
Bergman, "C—H Activation", Organometallic Chemistry, Mar. 2007, 446, 391-393.
Boe, B., "The Mechanism of the Acid-Catalyzed Propanolysis of 2-Sila-1,3-Dioxolanes", Journal of Organometallic Chemistry, Oct. 1972, 43(2), 275-284.
Chattejee, B., et al., Chemical Communications, 2014, 50 (7), 888-890.
Cheng et al., "Rhodium-Catalyzed Intermolecular C—H Silylation of Arenes with High Steric Regiocontrol", Science, Feb. 2014, 343(6173), 853-857.
Chrusciel, J.J., "29Si NMR studies on the mechanism of dehydrocoupling of hydrosilanes with hydroxylic reagents in DMF—The role of DMF", Canadian Journal of Chemistry, 2005, 83(5), 508-516.
Chuit et al., "Reactivity of Penta-and Hexacoordinate Silicon Compounds and Their Role as Reaction Intermediates", Chemical Reviews, 1993, 93(4), 1371-1448.
Clark, J.H., "Green Chemistry: Challenges and Opportunities", Green Chemistry, Feb. 1999, 1-8.

(Continued)

*Primary Examiner* — Joseph R Kosack
*Assistant Examiner* — Sagar Patel
(74) *Attorney, Agent, or Firm* — BakerHostetler

(57) ABSTRACT

The present disclosure is directed to methods for dehydrogenatively coupled hydrosilanes and alcohols, the methods comprising contacting an organic substrate having at least one organic alcohol moiety with a mixture of at least one hydrosilane and sodium and/or potassium hydroxide, the contacting resulting in the formation of a dehydrogenatively coupled silyl ether. The disclosure further described associated compositions and methods of using the formed products.

21 Claims, 1 Drawing Sheet

(56) References Cited

OTHER PUBLICATIONS

Corey et al., "Diisopropylsilyl Ditriflate and Di-tert-Butysilyl Ditriflate: New Reagents for the Protection of Diols", Tetrahedron Letters, 1982, 23(47), 4871-4874.
Corey et al., "Protection of Hydroxyl Groups as tert-Butyldimethylsilyl Derivatives", Journal of the American Chemical Society, 1972, 94(7), 6190-6191.
Cragg, R. H., and R. Lane, "Contributions to Group IV Organometallic Chemistry Part XIII Preparation and Properties of some Organo-1,3,2-dioxasilacycloalkanes", Main Group Metal Chemistry (1987), 10 (5), pp. 315-351. (Year: 1987).
Curran, D. P. et al., Journal of the Chemical Society, Perkin Transactions 1: Organic and Bio-Organic Chemistry (1972-1999), 1995, 24, 3049-3060.
Das et al., "Selective Catalytic Monoreduction of Phthalimides and Imidazolidine-2,4-diones", Angewandte Chemie, Sep. 2011, 50(39), 9180-9184.
Denmark et al., "Design and Implementation of New, Silicon-Based, Cross-Coupling Reactions: Importance of Silicon-Oxygen Bonds", Acc. Chem. Res., 2002, 35, 835-84.
Denmark et al., "Palladium-Catalyzed Cross-Coupling Reactions of Organosilanols and Their Salts: Practical Alternatives to Boron- and Tin-Based Methods", Acc. Chem. Res., Oct. 2008, 41(11), 1486-1499.
Denmark et al., "Palladium-Catalyzed Cross-Coupling Reactions of Silanolates: A Paradigm Shift in Silicon-Based Cross-Coupling Reactions", Chemistry European Journal, Jun. 2006, 12(19), 4954-4963.
Denmark et al., "Reaction Mechanisms: Lewis Base Catalysis in Organic Synthesis", Angew. Chem. Int. Ed., 2008, 47, 1560-1638.
Donadel et al., "The tert-butyl dimethyl silyl group as an enhancer of drug cytotoxicity against human tumor cells", Bioorganic & Medicinal Chemistry Letters, Aug. 2005, 15(1), 3536-3539.
Eaborn, C., "Cleavages of Aryl-Silicon and Related Bonds by Electrophiles", Journal of Organometallic Chemistry, Oct. 1975, 100(1), 43-57.
Fedorov et al., "Lewis-Base Silane Activation: From Reductive Cleavage of Aryl Ethers to Selective Ortho-Silylation", Chem. Sci., 2013, 4, 1640-1645.
Fernandes, et al., Chem. Comm., "[MoO2Cl2] as catalyst for hydrosilylation of aldehydes and ketones", 2005, 2, 213-214.
Franz et al., "Organosilicon Molecules with Medicinal Applications", Journal of Medicinal Chemistry, 2013, 56(2), 388-405.
Fujiki et al., "Optically Active Polysilanes. Ten Years of Progress and New Polymer Twist for Nanoscience and Nanotechnology", Polymer Journal, 2003, 35(4), 297-344.
Gevorgyan, V., L. Borisova and E. Lukevics, "Palladium-catalyzed rearrangement of silanes containing oxygen or halogen to silicon" J. Organomet. Chem. (1992), 436 (3), pp. 277-285. (Year: 1992).
Godula et al., "C—H Bond functionalization in Complex Organic Synthesis", Science, Apr. 2006, 312, 67-72.
Goldberg, Y., et al., Journal of Organometallic Chemistry, 1991, 410 (2), 127-133.
Goldberg, Y., et al., Synthetic Communications, 1990, 20 (16), 2439-2446.
Grajewska et al., "Base-Catalyzed Dehydrogenative Si—O Coupling of Dihydrosilanes: Silylene Protection of Diols", Synlett, 2010, 16, 2482-2484.
Grishina, Y. V., N. S. Fedotov and V. D. Sheludyakov, "Chemical Conversions of Alkyl (Silyl Ethyl) Adamantanes", Journ. Gen. Chem. (1988), 58 (8), pp. 1849-1853. (Year: 1988).
Hartwig et al., "Borylation and Silylation of C—H Bonds: A Platform for Diverse C—H Bond Functionalizations", Acc. Chem. Res. 2012, 45(6), 864-873.
Horner, L., et al., Journal of Organometallic Chemistry, 1985, 282, 155-174.
Huang et al., "Silanol—A Traceless Directing Group for Pd-Catalyzed o-Alkenylation of Phenols", J Am Chem Soc, Aug. 2011, 133(32), 12406-12409.

Huang et al., "Synthesis of Catechols from Phenols via Pd-Catalyzed Silanol-Directed C—H Oxygenation", J. Am. Chem. Soc., Nov. 2011, 133(44), 17630-17633.
Hunter et al., "Organo-Silicon Polymers. The Cyclic Dimethyl Siloxanes", Journal of the American Chemical Society, Apr. 1946, 68(4), 667-672.
Igarashi, M., et al., Chemistry Letters, 2014, 43 (4), 429-431.
Itagaki, S., et al., Chemistry Letters, 2013, 42 (9), 980-982.
Kamino et al., "The use of siloxanes, silsesquioxanes, and silicones in organic semiconducting materials", Chem. Soc. Rev., 2013, 42, 5119-5230.
Kaplan et al., "Hydrogen Isotope Effects in the Alkaline Cleavage of Triorganosilanes1", Journal of the American Chemical Society, 1955, 77(5), 1297-1302.
Kennedy-Smith, J. J., et al., J. Amer. Chem. Soc., 2003, 125 (14), 4056-4057.
Kim et al., "Thermally stable transparent sol-gel based siloxane hybrid material with high refractive index for light emitting diode (LED) encapsulation", Chem. Mater., 2010, 22, 3549-3555.
Kita, Y., et al., Tetrahedron Letters, 1983, 24 (12), 1273-1276.
Kuroda et al., "Utilization of Alkoxysilyl Groups for the Creation of Structurally Controlled Siloxane-Based Nanomaterials", Chem. Mater., 2014, 26(1) 211-220.
Labinger et al., "Understanding and exploiting C—H Bond activation", Nature, May 2002, 417, 507-514.
Le Bideau, F., T. Coradin, J. Henique, and E. Samuel "On a new catalyzed silylation of alcohols by phenylhydrosilanes" Chem. Commun. (2001), pp. 1408-1409.
Le Bideau, Williams, DBG and M. Lawton, Journ. Org. Chem, 2010, 75(24), 8351-8354.
Li et al., "Green Chemistry for Chemical Synthesis", PNAS, Sep. 2008, 105(36) 13197-13202.
Li et al., "Green Chemistry: The development of cross-dehydrogenative coupling (CDC) for chemical synthesis", Pure Appl. Chem., 2006, 78(5), 935-945.
Li, C.-J., "Cross-Dehydrogenative Coupling (CDC): Exploring C#C Bond Formations Beyond Functional Group Transformations", Acc. Chem. Res., 2009, 42(2) 335-344.
Lukevics et al., "The Alcoholysis of Hydrosilanes", Journal of Organometallic Chemistry, Nov. 1985, 295(3), 265-315.
Mai et al., "Alkylsilyl Cyanides as Silylating Agents", The Journal of Organic Chemistry, 1986, 15(18), 3545-3548.
Material Safety Data Sheet—Crown Ether/ Dicyclohexyl-18-crown-6. Midland scientific. http://www.midlandsci.com/customer/miscne/specpages/msdsu_811866.pdf.
Merker et al., "The Preparation and Properties of Some Silylmethyl and Silylpropyl Substituted Tin Compounds", JACS, Feb. 1959, 81, 975-978.
Mitsudome, T., et al., Chemistry—A European Journal, 2013, 19 (43), 14398-14402.
Mukherjee, D., R. Thompson, A. Ellern, and A. Sadow "Coordinatively saturated Tris(oxazolinyl)borato zinc hydride-catallyzed cross dehydrocoupling of silanes and alcohols" ACS Catal. (2011), 1: pp. 698-702.
Nakao et al., "Silicon-based cross-coupling reaction: an environmentally benign version", Chemical Society Reviews, May 2011, 40(10), 4893-4901.
Okano et al., "Copper-mediated aromatic animation reaction and its application to the total synthesis of natural products", Chemical Communications, Jul. 2014, 50(89), 13650-13663.
Pangborn et al., "Safe and Convenient Procedure for Solvent Purification", Organometallics, 1996, 15(5), 1518-1520.
Park, J. W. et al., "Highly Efficient O-Silylation of Alcohol with Vinylsilane Using a Rh(I)/HCL Catalyst at Room Temperature", Organic letters, 2009, vol. 9, No. 20, pp. 4073-4076 (Eupub. Sep. 8, 2007).
Price, F.P., "Mechanism of the Alkaline Cleavage of Silicon-Hydrogen Bonds: Temperature Coefficients of the Rate of Cleavage of Several Trialkylsilanes", Journal of the American Chemical Society, 1947, 69(11), 2600-2604.
Rendler et al., "Hypervalent Silicon as a Reactive Site in Selective Bond-Forming Processes", Synthesis, 2005, 11, 1727-1747.

(56) References Cited

OTHER PUBLICATIONS

Rendler, S. et al., "Stereoselective Alcohol Silylation by Dehydrogenative Si—O Coupling: Scope, Limitations and Mechanism of the Cu—H-Catalyzed Non-Enzymatic Kinetic Resolutuion with Silicon-Stereogenic Silanes", Chemistry—A European Journal, 2008, vol. 14, No. 36, pp. 11512-11528.
Revunova et al., "Base-Catalyzed Hydrosilylation of Ketones and Esters and Insight into the Mechanism", Chemistry European Journal, Jan. 2014, 20(3), 839-845.
Scheuermann, C.J., "Beyond Traditional Cross Couplings: The Scope of the Cross Dehydrogenative Coupling Reaction", Chemistry Asian Journal, Mar. 2010, 5(3) 436-451.
Schowen et al., "Evidence for Proton Transfer Concomitant with Hybride Expulsion from Silanes", Tetrahedron Letters, 1970, 11(48), 4177-4180.
Showell et al., "Chemistry challenges in lead optimization: silicon isosteres in drug discovery", Drug Discovery Today, Jun. 2003, 8(12), 551-556.
Sierra, M.A., et al., "Synthesis of Terpene and Steroid Dimers and Trimers Having Cyclobutadienyl-Co and Aromatic Tethers", The Journal of Organic Chemistry, vol. 72, No. 11, 2007, pp. 4213-4216 (Eupub. May 4, 20017).
Sommer et al., "Stereochemistry of asymmetric silicon. XIX. Nucleophilic substitutions involving hydrogen and carbon as leaving groups and further demonistration of stereochemistry crossover", Journal of the American Chemical Society, 1972, 94(10), 3463-3469.
Spletstoser et al., Tandem Silyformylation—Crotylsilylation/Tamo Oxidation of Internal Alkynes: A Remarkable Example of Generating Complexity from Simplicity, Organic Letters, 2008, 10(24), 5593-5596.
Tanabe et al., "Mild and Practical Method for the Silylation of Alcohols Using Hydrosilanes and Disilanes Promoted by TBAF Catalyst", Tetrahedron Letters, 1994, 35(45), 8413-8414.
Tanino, K., N. Yoshitani, F. Moriyama and I. Kuwajima, "Control of Stereochemistry by participation of a Silyl Group. A Novel Method for Diastereoselective Polyol Synthesis" J. Org. Chem. (1997), 62 (13), pp. 4206-4207. (Year: 1997).
Toutov et al., "Catalytic C—H bond silylation of aromatic heterocycles", Nature Protocols, Oct. 2015, 10, 1897-1903.
Toutov et al., "Silylation of CH bond in aromatic heterocycles by an Earth-abundant metal catalyst", Nature, Feb. 2015, 518(7537), 80-84.
Tucker, J.L., "Green Chemistry, A Pharmaceutical Perspective", Organic Process Research & Development, 2006, 10, 315-319.
Ueno et al., "Nucleiphilic aromatic substitution using Et3SiH/cat. t-Bu-P4 as a system for nucleophile activation", Chemical Communications, 2007, 22, 2264-2266.
Wang, et al,,Angew Chem Int Ed Engl. Feb. 9, 2015; 54(7): 2255-2259.
Weickgenannt et al., "Potassium tert-Butoxide-Catalyzed Dehydrogenative Si—O Coupling: Reactivity Pattern and Mechanism of an Underappreciated Alcohol Protection", Chemistry Asian Journal, Mar. 2009, 4(3), 406-410.
Williams, DBG and M. Lawton, "Drying of Organic Solvents: Quantitative Evaluation of the Efficiency of Several Dessiccants" Journ. Org. Chem. (2010), 75(24), pp. 8351-8354. (Year: 2010).
Yamamoto, K., et al., Bulletin of the Chemical Society of Japan, 1989, 62 (6), 2111-2113.
Zacuto, et al., "Tandem Intramolecular Silylformylation—Crotylsilylation: Highly Efficient Synthesis of Polyketide Fragments", J. Am. Chem. Soc., 2002, 124, 7890-7891.
Joffe et al., "Studies in silico-organic compounds. VIII. The preparation and properties of polyethers from trichlorosilane, continued 1, 2", Journal of Organic Chemistry, May 1, 1949, vol. 14, No. 3, pp. 421-428.

* cited by examiner

HYDROXIDE-CATALYZED FORMATION OF SILICON-OXYGEN BONDS BY DEHYDROGENATIVE COUPLING OF HYDROSILANES AND ALCOHOLS

CROSS REFERENCE TO RELATED APPLICATIONS

This application is a divisional of U.S. patent application Ser. No. 15/219,710, filed Jul. 26, 2016, that claims the benefit of priority from U.S. Patent Application Nos. 62/198,405, filed Jul. 29, 2015, and 62/269,746, filed Dec. 18, 2015 the contents of which are incorporated by reference herein for all purposes.

GOVERNMENT RIGHTS

This invention was made with government support under Grant No. CHE1212767 and CHE1205646 awarded by the National Science Foundation. The government has certain rights in the invention.

TECHNICAL FIELD

The present invention is directed at methods of forming silicon-oxygen bonds by dehydrogenative coupling of hydrosilanes and alcohols

BACKGROUND

The silicon-oxygen (Si—O) bond is an extremely useful feature in organic chemistry, at least for its use in protecting group chemistries, its utility as a traceless directing group in organic synthesis, and its prevalence in a number of important functional material classes. The silylative protection of alcohols has further been employed in drug discovery to improve pharmacokinetic properties of pharmaceutically relevant molecules and to enhance drug toxicity.

A large number of catalytic methods for the construction of O—Si bonds have been developed (FIG. 1A). The direct silylation of alcohols by transition metal catalysis or Bronsted and Lewis acids/bases and catalytic hydrosilylation of carbonyl compounds have been the most commonly employed protocols. However, despite decades of work, the most prominent method for the construction of the Si-0 bond is the treatment of alcohols with moisture-sensitive chlorosilanes in the presence of nucleophilic catalysts and a base to scavenge the HCl generated. Moreover, in certain challenging cases such as the silylene protection of 1,2-diols with certain silanes, the use of highly reactive or toxic electrophilic silicon reagents is necessary. As a result, the development of an effective, general, and convenient O—Si construction methodology which circumvents the production of stoichiometric salt by-products and avoids the use of toxic and moisture-sensitive electrophilic silicon sources, while simultaneously improving the scope in comparison to previous methods would be of considerable interest to chemists working in a variety of fields.

The present invention takes advantage of the discoveries cited herein to avoid at least some of the problems associated with previously known methods.

SUMMARY

Herein is disclosed a mild, efficient, and generally direct cross-dehydrogenative Si—O bond construction protocol employing NaOH and unactivated KOH as the catalyst is described (see, e.g., FIG. 1B). The method allows for the direct coupling of an O—H bond and a silane Si—H bond to furnish the corresponding O—Si bond in a single step, without the production of stoichiometric salt by-products. The catalysis proceeds under mild conditions, in the absence of transition metal salts, hydrogen acceptors, or other additives and liberates dihydrogen as the sole by-product. The scope of the method is broad, enabling the direct silylation of primary, secondary, and tertiary alcohols as well as diols, polyols, and phenols in the presence of halide, nitro, and carbonyl functionalities as well as strained rings, olefins, alkynes, and electron rich and electron deficient aromatic heterocycles. The scope of the hydrosilane is excellent, enabling high steric and electronic tunability of the resultant O—Si bond, which would be of value in a number of applications including protecting group chemistry, materials science, and even drug discovery. Facile scalability, low cost, and broad scope make this a practical and attractive O—Si bond construction strategy. Applications to directing group chemistry and a multi-gram scale synthesis of a novel cross-coupling reagent are demonstrated.

Various embodiments includes methods comprising or consisting essentially of contacting an organic substrate having at least one organic alcohol moiety with a mixture of at least one hydrosilane and a sodium and/or potassium hydroxide, in the absence of hydroxide activators, the contacting resulting in the formation of a dehydrogenatively coupled silyl ether. In related embodiments, the method is conducted in the substantial absence of transition metal catalysts, in the substantial absence of "superbases," such as alkoxides, hydrides, alkyl lithium reagents, anionic amide or phosphine bases, or any chemical known to enhance the activity of the NaOH or KOH (e.g., crown ethers), and in the substantial absence of fluoride ion.

In the methods and the related compositions, the at least one hydrosilane comprises a hydrosilane of Formula (I) or a hydrodisilane of Formula (II):

$(R)_{3-m}Si(H)_{m+1}$ (I)

$(R)_{2-m}(H)_{m+1}Si-Si(R)_{3-m}(H)_m$ (II)

where m is independently 0, 1, or 2; and each R is broadly defined herein. The hydrosilane may be monomeric, oligomeric, or polymeric, or tethered to insoluble or sparingly soluble support media.

In some embodiments, the organic substrate having at least one organic alcohol moiety has a structure of Formula (IIIA):

$R^1$—OH (IIIA)

where $R^1$ comprises an optionally substituted $C_{1-24}$ alkyl, optionally substituted $C_{2-24}$ alkenyl, optionally substituted $C_{2-24}$ alkynyl, optionally substituted $C_{6-24}$ aryl, optionally substituted $C_{1-24}$ heteroalkyl, optionally substituted 5- or 6-ring membered heteroaryl, optionally substituted $C_{7-24}$ aralkyl, optionally substituted heteroaralkyl, or optionally substituted metallocene.

In other embodiments, the organic substrate having at least one organic alcohol moiety is at least a diol, having a structure of Formula (IIIB):

HO—$R^2$—OH (IIIB), where $R^2$ comprises an optionally substituted $C_{2-12}$ alkylene, optionally substituted $C_{2-12}$ alkenylene, optionally substituted $C_{6-24}$ arylene, optionally substituted $C_{1-12}$ heteroalkylene, or an optionally substituted 5- or 6-ring membered heteroarylene. In some of these embodiments, the organic substrate having at least one organic alcohol moiety is or comprises an optionally substituted catechol moiety or has a Formula (IV):

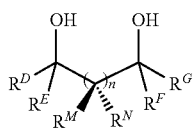

(IV)

wherein n is from 0 to 6, preferably 0 or 1;
$R^M$ and $R^N$ are independently H or methyl
$R^D$, $R^E$, $R^F$, and $R^G$ are independently H, $C_{1-6}$ alkyl, $C_{1-6}$ alkenyl, optionally substituted phenyl, optionally substituted benzyl, or an optionally substituted 5- or 6-ring membered heteroaryl, wherein the optional substituents are $C_{1-3}$ alkyl, $C_{1-3}$ alkoxy, or halo. Within this genus, the organic substrate includes substituted 1,2-diols, 1,3-diols, 1,4-diols, these being substituted with one or more alkyl and/or optionally substituted aryl or heteroaryl substituents. A range of such diols are discussed in this disclosure. The organic substrate having at least one organic alcohol moiety may be polymeric and/or comprise an aliphatic alcohol moiety, an aromatic or α-methyl aromatic alcohol moiety, or specifically an optionally substituted benzylic alcohol moiety.

In some embodiments, the methods may be used to prepare a range of synthons, which are useful in a range of downstream transformations, including the preparation of catechols (or other dihydroxylated aryl or heteroaryl moieties), ortho-alkenylated phenol (or other alkenylated 5- and 6-membered heteroaryl hydroxy moieties), ortho-carboxylic acid phenols (or other carboxylated 5- and 6-membered heteroaryl hydroxy moieties). Other of the methods provide for a range of dioxasilolane derivatives, which are useful as aryl transfer reagents (including reacting with aromatic halides, such as bromides or iodides, to form biaromatic product or aminating benzimidazoles) and for preparing beta-aromatic substituted $C_{1-6}$ propionate ester products. A range of specific hydrosilane/alcohol combinations are disclosed herein, as are the downstream transformations, each of which is considered an independent embodiment of the present invention.

Those compositions associated with the methods and transformations described herein are also considered independent embodiments within the scope of the present invention.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, processes, devices, and systems disclosed. In addition, the drawings are not necessarily drawn to scale. In the drawings.

DETAILED DESCRIPTION OF ILLUSTRATIVE EMBODIMENTS

Figure 1:
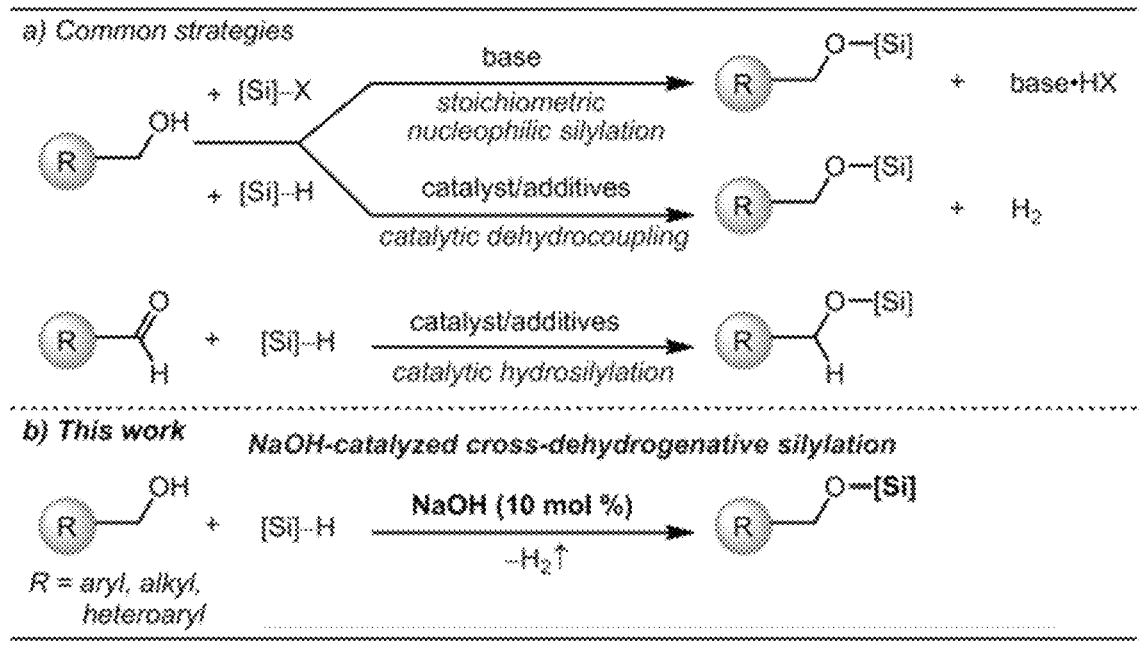
FIG. 1 illustrates various strategies for preparing silyl ethers.
Figure 2:
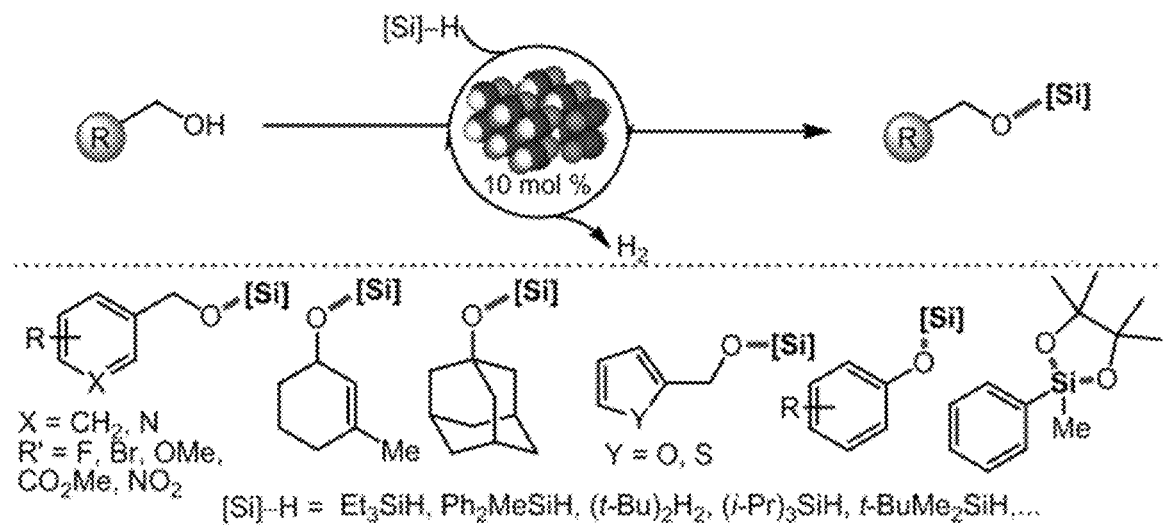
FIG. 2 provides an exemplary overview of the substrates considered within the scope of the present invention.

The present invention is founded on a set of reactions, each of which relies on simple mixtures of hydrosilanes and uncomplexed potassium hydroxide and sodium hydroxide, which together form in situ systems (the structure and nature of the active species is still unknown) able to dehydrogenative couple hydrosilanes and alcohols, and when combined, do so. Such transformations proceed without the required presence of transition metal catalysts, superbases, fluoride ion, UV radiation or electrical (including plasma) discharges. These reactions are relevant as an important advance in developing practical methods for the preparation of products important for agrochemical, electronics, fine chemicals, and pharmaceutical applications. They provide an important synthetic tool with respect to alcohol protection and directing strategies. Importantly this reaction is of further interest since it produces only environmentally benign silicates as the byproduct and can avoid metal waste streams or the use of harsh chemical catalysts. The remarkable facility exhibited by these systems provides a useful tool in the kit of chemists in these fields. Again, this utility can be leveraged when combined with other follow-on reactions.

The present invention may be understood more readily by reference to the following description taken in connection with the accompanying Figures and Examples, all of which form a part of this disclosure. It is to be understood that this invention is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to both the compositions and methods of making and using said compositions. That is, where the disclosure describes or claims a feature or embodiment associated with a composition or a method of making or using a composition, it is appreciated that such a description or claim is intended to attribute these features or embodiment to embodiments in each of these contexts (i.e., compositions, methods of making, and methods of using).

Methods of Dehydrogenatively Coupling Hydrosilanes and Alcohols

The present invention includes embodiments related to methods for dehydrogenatively coupling hydrosilanes and alcohols (or other hydroxy-containing materials, including inorganic materials), their related compositions, and methods of using the derived products.

Some embodiments provides methods comprising contacting an organic substrate having at least one organic alcohol moiety with a mixture of at least one hydrosilane and a sodium and/or potassium hydroxide, the contacting resulting in the formation of a dehydrogenatively coupled silyl ether. The use of NaOH, KOH, or a mixture thereof are considered independent embodiments of these methods. While throughout this disclosure, the invention is described in terms of organic substrates, it is important also to note that the methods and compositions are also directed to embodiments in which the substrate is or comprises an inorganic substrate, such as a hydrated oxide (e.g., of alumina, silica, titania, or zirconia, including hydroxylated aluminum, silicon, titanium, or zirconium surfaces) or water. In the former case, the product is a silylated inorganic surface; in the latter case, the product is a siloxane. The ability to append polysilanes onto hydrated inorganic oxides is especially valuable given the importance of Si—Si oligomers and polymers in materials science applications, as described in Fujiki, M. *Polymer Journal* 2003, 35, 297-344, this reference being incorporated by reference at least for its teaching of the methods of preparing and uses of such systems. Additionally, the reaction of diethylsilane with water under NaOH catalysis resulted in the formation of cyclic siloxanes, with trisiloxane being the major product by GC-MS analysis. These products are precursors to valuable polysiloxanes, as described for example in M. J. Hunter, et al., *J. Am. Chem. Soc.,* 1946, 68, 667-672. This reference is also incorporated by reference at least for its teaching of the methods of preparing and uses of such systems.

Base-catalyzed methods for the formation of O—Si bonds by dehydrocoupling have been investigated by others, but not under the reactions conditions considered in the present disclosure. Indeed, the use of simple base catalysts of the present invention are practically convenient and robust. In stark contrast, the catalysts previously used have tended to be highly basic, for example, using hydrides, alkoxides, and transition metal hydrides, with or without n-butyl lithium (the term "superbase" is used herein to describe these stronger bases). See, e.g., A, Weickgennant, et al., *Chem. Asian J.* 2009, 4, 406-410.) and A. Grajewska, et al., *Synlett,* 2010, 16, 2482-2484. Aside from the challenges of working with these highly reactive materials, these methods do not have the scope and/or practical convenience/cost benefits of the methods disclosed here. Silylation of alcohols by hydrosilanes or disilanes have also been facilitated by fluoride ion (as tetrabutyl ammonium fluoride). Potassium hydroxide has been previously used, but even here, the reactions conditions required the use of costly additives such as crown-ethers for activation. See, e.g., F. Le Bideau, et al., *Chem. Commun.* 2001, 1408-1409. Consequently, the resultant scope of previous reports have been modest: phenols are notably absent, as is monosilylation with dihydrosilanes, and very few functional groups of value in downstream modification are described.

In the present disclosure, it is shown that the use of a milder basic catalyst may greatly improve the scope of the reaction compared to previous methods such as allowing reactions with phenols and dihydrosilanes and could potentially tolerate valuable and sensitive functional groups on the alcohol substrate and on the hydrosilane. Furthermore, using a less sterically demanding base catalyst allows for the introduction of bulkier hydrosilane coupling partners, enabling the catalytic silylene protection of 1,2-diols, which can be otherwise challenging by both stoichiometric and catalytic means. The present methods provide a practical, convenient, and general cross-dehydrogenative O—Si bond construction protocol, enabled by alkali metal hydroxide-catalyzed Si—H/O—H bond coupling. The catalysts, NaOH and KOH, in the absence of crown ether activators, exhibit the attributes of (a) high functional group compatibility and mild basicity' (b) minimal steric demand to satisfy sterically demanding hydrosilanes and alcohol substrates; (c) ability to catalyze the dehydrocoupling reaction under mild conditions, and (d) have low toxicity and good tolerance to ambient conditions. The specific nature of the $K^+$ and especially $Na^+$ in the present systems appears to confer at least some of the benefits to the methods and systems.

The methods operate well in the complete or substantial absence of transition metal ions, compounds, or catalysts. As used herein, unless otherwise stated, the term "substantial absence" refers to the absence of deliberately added material, in this case of transition metal catalysts known to be or suspected of being operable in such dehydrogenative coupling reactions. Where otherwise specified, the term may also refer to the presence of the material at or below a certain threshold levels described elsewhere herein. In certain embodiments, the methods are conducted in the substantial absence of transition metal ions or catalysts. In other embodiments, the methods are conducted with less than 1000 ppm, 100 ppm, 50 ppm, or 10 ppm, based on the total weight of the system.

Likewise, these methods are also operable in the absence or substantially complete absence of other electromagnetic or thermal triggers needed for initiation or propagation. That is, these embodiments do not need or use UV irradiation or electric or plasma discharge conditions to operate.

In other embodiments, the methods are conducted in the substantial absence of "superbases," such as alkoxides, hydrides, alkyl lithium reagents, or any chemical known to enhance the activity of the NaOH or KOH (e.g., crown ethers). Specifically in the case of NaOH or KOH, unless otherwise explicitly specified, the use of NaOH or KOH refers to compositions or methods in which the systems which are completely or substantially devoid of crown ethers, cryptands, polyoxy- or polyamino-ligands, ionophores, or other alkali metal chelating agents which are known to chelate the $Na^+$ or $K^+$ cations. While other embodiments allow for their selective presence, as a general feature, the methods and systems avoid the use of these materials. In other embodiments, the methods are conducted in the complete or substantial absence of fluoride ion (which may be present as tetraalkyl ammonium fluoride, for example).

Within the scope of the disclosure, there are few limits placed on the nature of the hydrosilane reagents, at least in the sense that these may be individual discrete compounds, may be part of oligomeric or polymeric structures, or may be tethered to insoluble or sparingly soluble support media for ease of work-up. That said, the hydrosilanes used in the present work are conveniently presented as soluble or at least simple compounds, In certain embodiments, the hydrosilane has a structure of Formula (I) or of Formula (II):

where: m is independently 0, 1, or 2; and each R is independently optionally substituted $C_{1-24}$ alkyl or heteroalkyl, optionally substituted $C_{2-24}$ alkenyl or heteroalkenyl, optionally substituted $C_{2-24}$ alkynyl or heteroalkynyl, optionally substituted 6 to 18 ring membered aryl or 5 to 18 ring membered heteroaryl, optionally substituted 6 to 18 ring-membered alkaryl or 5 to 18 ring-membered heteroalkaryl, optionally substituted 6 to 18 ring-membered aralkyl or 5 to 18 ring-membered heteroaralkyl, optionally substituted —O—$C_{1-24}$ alkyl or heteroalkyl, optionally substituted 6 to 18 ring-membered aryloxy or 5 to 18 ring-membered heteroaryloxy, optionally substituted 6 to 18 ring-membered alkaryloxy or 5 to 18 ring-membered heteroalkaryloxy, or optionally substituted 6 to 18 ring-membered aralkoxy or 5 to 18 ring-membered heteroaralkoxy, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, 5 to 12 ring-membered arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon. In individual embodiments, m is 0, m is 1, m is 2. Each of the compounds of Formula (I) and Formula (II) represent independent embodiments.

In other embodiments, the hydrosilane is $(R)_3SiH$, $(R)_2SiH_2$, or $(R)SiH_3$, where R is independently $C_{1-6}$alkoxy, $C_{1-6}$alkyl, $C_{2-6}$alkenyl, $C_{6-24}$aryl, $C_{7-25}$aryloxy, a 5- of 6-ring membered heteroaryl, aralkyl, or heteroaralkyl compound or moiety. These substituents may be substituted or unsubstituted, the optional substituents being described elsewhere herein. In certain specific embodiments, the hydrosilane is a compound of Formula (I), where m is 1; in others, the hydrosilane is a compound of Formula (I), where m is 2. In other embodiments, the hydrosilane is $EtMe_2SiH$, $Et_3SiH$, $(n-Bu)_3SiH$, $(i-Pr)_3SiH$, $Et_2SiH_2$, $Ph_2MeSiH$, $(t-Bu)Me_2SiH$, $(t-Bu)_2SiH_2$, $PhMeSiH_2$, $PhMe_2SiH$, $BnMe_2SiH$, $(EtO)_3SiH$, $Me_2(pyridinyl)SiH$, $(i-Pr)_2(pyridinyl)SiH$, $Me_3Si—SiMe_2H$, or any of the hydrosilanes exemplified in the Examples.

One of the many important features of the present invention is the wide range of alcohols that can be used in the present methods. The methods are expected to be operable using mono-alcohols, diols, triols, polyols, sugars, polyhydridic alcohols (including so-called sugar alcohols, such as arabitol, erythritol, glycerol, mannitol, sorbitol, and xylitol) and oligomers and polymers comprising one or more alcohol moieties. In certain embodiment, for example, the organic substrate having at least one organic alcohol moiety has a structure of Formula (IIIA):

$$R^1—OH \qquad (IIIA)$$

where $R^1$ comprises an optionally substituted $C_{1-24}$ alkyl, optionally substituted $C_{2-24}$ alkenyl, optionally substituted $C_{2-24}$ alkynyl, optionally substituted $C_{6-24}$ aryl, optionally substituted $C_{1-24}$ heteroalkyl, optionally substituted 5- or 6-ring membered heteroaryl, optionally substituted $C_{7-24}$ aralkyl, optionally substituted heteroaralkyl, or optionally substituted metallocene. In other embodiments, the organic substrate has a structure of Formula (IIIB):

$$HO—R^2—OH \qquad (IIIB),$$

where $R^2$ comprises an optionally substituted $C_{2-12}$ alkylene, optionally substituted $C_{2-12}$ alkenylene, optionally substituted $C_{6-24}$ arylene, optionally substituted $C_{1-12}$ heteroalkylene, or an optionally substituted 5- or 6-ring membered heteroarylene. In both cases, the optional substituents are described elsewhere herein for these substituents. In the case of the diols, In certain, the organic substrate having at least one organic alcohol moiety can comprise an optionally substituted catechol, an optionally substituted neopentyldiol an optionally substituted pinacol, or a homolog thereof.

In more general embodiments, the organic substrate having at least one organic alcohol moiety is or comprises an optionally substituted catechol moiety or has a Formula (IV):

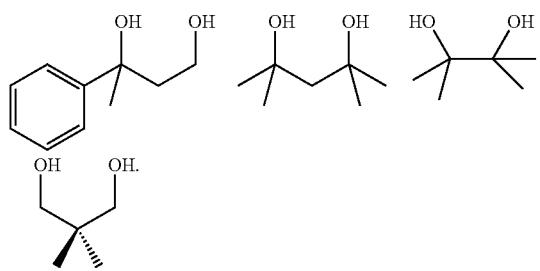

wherein n is from 0 to 6, preferably 0 or 1;

$R^M$ and $R^N$ are independently H or methyl $R^D$, $R^E$, $R^F$, and $R^G$ are independently H, $C_{1-6}$ alkyl, optionally substituted phenyl, optionally substituted benzyl, optionally substituted 5- or 6-ring membered heteroaryl, wherein the optional substituents are as described elsewhere herein, preferably $C_{1-3}$ alkyl, $C_{1-3}$ alkoxy, or halo. In certain of these embodiments, the organic substrate include substituted 1,2-diols, 1,3-diols, 1,4-diols, these being substituted with one or more alkyl (including methyl) and/or aryl (including optionally substituted aryl or heteroaryl. Depending on the substituents, the diols may be chiral or achiral, and those comprising chiral and achiral are considered independent embodiments within the scope of the present disclosure. For example:

As should be apparent to the skilled person, the terms 1,2-, 1,3-, and 1,4-diols refer to the relative positions of the diols with respect to one another, not necessarily with respect to a specific position on the carbon chain—see, e.g., the pinacol structure above may be considered a 1,2-diol, even though the diols are in the 2,3-positions.

Again, the organic substrate may be polymeric, containing one or more alcohol moieties in the polymer chain; e.g., polyvinyl alcohol, polyalkylene glycol, and vinyl alcohol copolymers (e.g., ethylene/vinyl alcohol copolymer). As shown in the Examples, in some embodiments, the at least one organic alcohol moiety comprises an alcohol having an organic framework comprising aliphatic, olefinic, acetylenic, cyclic, heterocyclic, or aromatic features. The methods also well tolerate the various functional groups as described as substituents herein (including, e.g., amides, esters, epoxides and other cyclic ethers, strained rings, etc.). In independent embodiments, the organic alcohol moiety may be bound to a primary, secondary, or tertiary carbon. Another of the attractive features of the present methods are the ability to form silyl ethers even with sterically crowded tertiary alcohols, for example, adamantol. The at least one organic alcohol moiety may also comprise an aromatic alcohol moiety, e.g., a phenol, naphthol, pyridinol, furanol, thiophenol, etc., or an α-methyl aromatic moiety, e.g., benzyl alcohol, pyridinyl-methanol, furanyl-methanol, thiophenyl-methanol, etc.

The Examples provide exemplary reaction conditions useful for affecting the desired transformations. In some embodiments, the conditions sufficient to silylate the organic substrate comprise heating the ingredients at a temperature in a range of about 10° C. to about 100° C. In some cases, the methods may be conducted with the reagents at a temperature defined by one or more of the ranges of from about 10° C. to 20° C., from 20° C. to 30° C., from 30° C. to 40° C., from 40° C. to 50° C., from 50° C. to 60° C., from 60° C. to 70° C., from 70° C. to 80° C., from 80° C. to 90° C., from 90° C. to 200° C., or higher. Any of the temperatures described in the Examples may be considered independent embodiments. Typical operating reaction times may range from about 2 hours, from about 4 hours, from about 6 hours, or from about 10 hours to about 28 days, to about 14 days, to about 7 days, to about 4 days, to about 3 days, to about 48 hours, to about 24 hours, to about 12 hours, or to about 6 hours. The methods may employ lesser or longer times as well.

These methods have been demonstrated using polar aprotic solvents, though other solvents may also be considered. Tetrahydrofuran, 1,2-dimethoxyethane, and dimethyl formamide have been shown to work especially well, but other polar aprotic solvents such as acetonitrile, dimethylacetamide (DMA), dimethyl formamide (DMF), dimethylsulfoxide, glycols and polyglycols (including, for example, dimethoxyethane, DME), optionally substituted dioxanes, dialkyl ethers (e.g., diethyl, dimethyl ether), hexamethylphosphoramide (HMPA), optionally substituted tetrahydrofurans (including 2-methyltetrahydrofuran) and furans, and N-methylpyrrolidone (NMP) are also expected to work well.

Downstream Reactions Using the Products of the Instant Disclosure

Once formed, the products of the disclosed methods can be used as convenient precursors to a range of "downstream" reactions (i.e., reactions to be applied subsequent to the disclosed coupling reactions), depending on the nature of the product. In certain embodiments, the various reactions may be done in so-called "one pot" conditions; in other embodiments, the coupled silyl ethers are isolated, and optionally purified, before progressing the downstream reactions. The present disclosure contemplates that methods employing these known methods, when coupled with the inventive methods described here, are within the scope of the present disclosure.

Given the flexibility of the methods, depending on the nature of hydrosilanes (for example, the size/bulk of the substituents) and alcohol precursors (as described above), a large array of products can be prepared, many of which are useful for downstream reactions. The Examples section provides a good overview of the types of manipulations available to the present method. In some cases, aside from the simpler chemistries, the present methods allows for the easy preparation of materials otherwise difficult to make or unaccessible by other means.

In one example of this flexibility, the reactivity of dihydrosilanes, $R_2SiH_2$, depends on the nature/bulk of the associated R-groups, as well as the relative hydrosilane/alcohol stoichiometry. Using bulky tertiary groups, such as tert-butyl, 2-methyl-butan-2-ol, or other alkyl-$C(CH_3)_2$—OH alcohols, as the substituents on the hydrosilanes (as in (tert-butyl)$_2$Si(H)$_2$), the resulting product is the corresponding simple hydrosilyl ether (less bulky dihydrosilanes tend to provide bridging silyl diethers—i.e., dialkoxysilanes—by double dehydrocoupling). See Examples 2.2.6 and 2.2.28 and compare Example 2.2.9. While many of the descriptions which follow are provided for the silylation of benzyl alcohol and phenol, respectively, it should be readily apparent that other mono-alcohols, including aryl or heteroaryl alcohols, would be similarly silylated to form the corresponding di-tert-butyl-hydrosilyl ether.

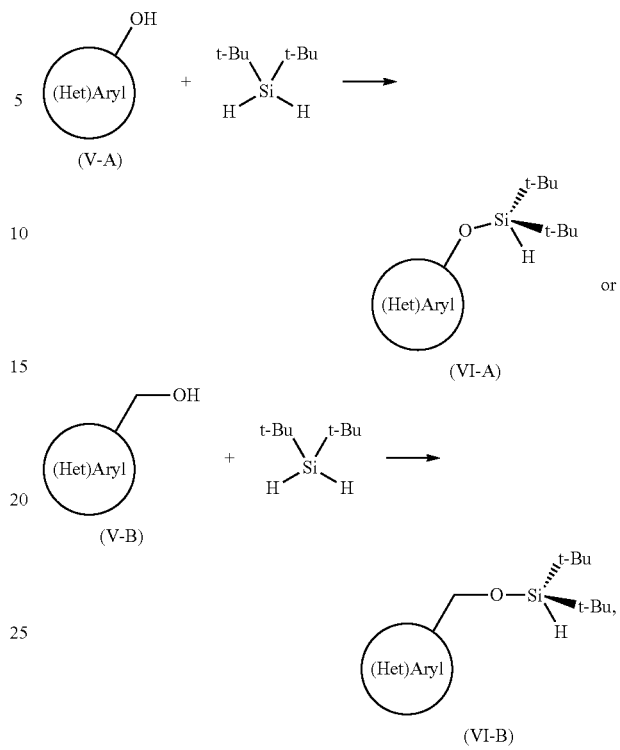

where (Het)aryl represents any phenyl, naphthyl, or 5- or 6-membered heteroaryl moiety. In one example of this class, where (Het)aryl is an optionally substituted phenyl, such a reaction may be represented schematically as:

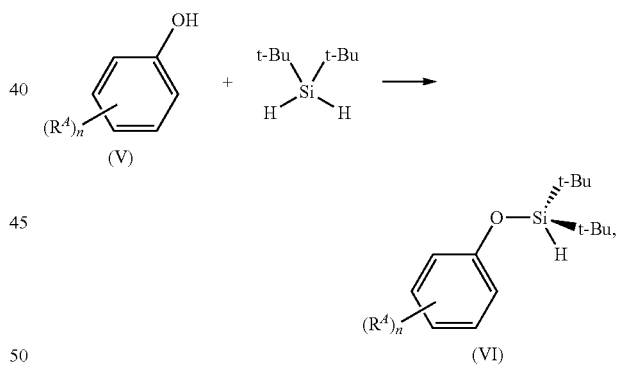

This example is presented here reflecting a phenol precursor, but again it is to be appreciated that an optionally substituted naphthol or hydroxylated 5- or 6-membered heteroaryl moiety may stand in the place of the phenyl ring of the phenol. In this regard, the following descriptions, while presented in the context of phenol chemistry, is expected to be operable as described for other aromatic (aryl and heteroaryl (Het (aryl))) alcohols, including, but not limited to those alcohols where Het(aryl) is or comprises a furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, or dibenzothiophene compound or moiety. Likewise, while this example is given using di-tert-butyl-dihydro-silane, it is also to be appreciated that other bulky substituents, for example tertiary alkyl groups, may be used instead of the tert-butyl groups. The following descriptions, then, while presented in the context of di-tert-butyl-dihydro-silane chemistry, is expected to be operable as described for other dihydrosilanes having similarly bulky substituents.

Within this framework, where at least one organic alcohol moiety is an optionally substituted phenol and the at least one hydrosilane is (tert-butyl)$_2$Si(H)$_2$, the reaction product comprising a di-tert-butyl silyl phenyl ether. Again, any hydroxylated naphthalene or 5- or 6-membered heteroaryl moiety made stand in place of the phenol and any bulky dihydrosilane may stand in the place of (tert-butyl)$_2$Si(H)$_2$. Without intending to limit the definition of the substitution on the phenol (or other aromatic), in certain embodiments, the phenol (or other aromatic) may be substituted as described in the structure of Formula (V), where n is 0, 1, 2, 3, 5, or 5, and R$^A$ is optionally at least one of aldehyde (—CHO), C$_{1-6}$ alkyl, C$_{1-6}$ alkylcarbonyl (—C(O)—C$_{1-6}$alkyl), C$_{1-6}$ alkoxy, C$_{1-6}$ alkoxycarbonyl (—C(O)—C$_{1-6}$alkyl), —C(O)—C$_{6-24}$ aryl), —C(O)—(5- or 6 membered heteroaryl), halo, nitrile, or nitro. In other embodiments, n is 2, and two R$^A$'s together with the phenyl ring form a fused 5- or 6 membered carbocyclic ring or 5- or 6 membered mono- or diether ring, e.g.,

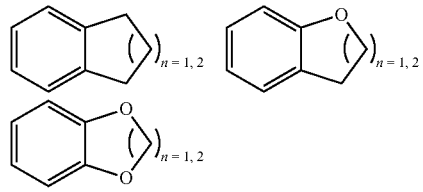

Such a reactions may be represented schematically as:

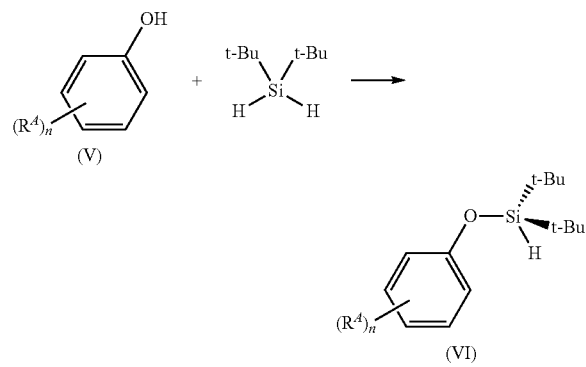

In further embodiments, the aromatic silyl ether (as exemplified by di-tert-butyl silyl phenyl ether) may be converted to a corresponding aromatic hydroxy silyl ether (e.g., di-tert-butyl hydroxy silyl phenyl ether). In certain aspects, this step comprises contacting the aromatic silyl ether with a base (e.g., hydroxide base) to form a aromatic hydroxy silyl ether. Without intending to limit the definition of the substitution of the substrates, in certain embodiments, the aromatic silyl ether has a structure of Formula (VI), or a corresponding structure for other aromatic analogs, where n is 0, 1, 2, 3, 5, or 5, and R$^A$ are described as elsewhere herein and the aromatic hydroxy silyl ether corresponding to Formula (VII) is correspondingly substituted. In certain of these embodiments, the base comprises a form of hydroxide, such as aqueous carbonate or basic (hydroxide-containing) DMF, as described for example in Huang, *J. Am. Chem. Soc.*, 2011, 133 (44), 17630-17633. Such a reaction may be represented schematically as:

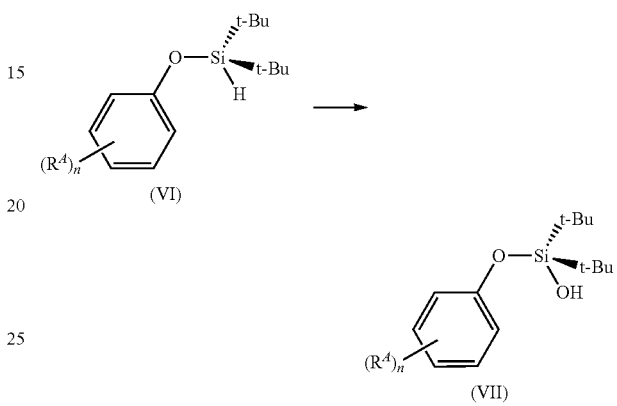

An overall exemplary transformation may be represented by the schematic:

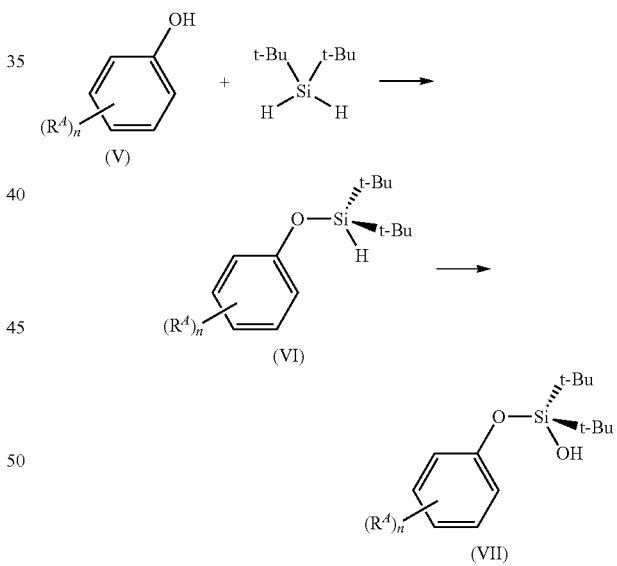

The phenyl version of this aromatic hydroxy silyl ether has been shown to be a useful intermediate for a range of reactions, some of which are described as follows, and it is expected that the corresponding aromatic analogs are equally useful.

In some embodiments, the aromatic hydroxy silyl ether (as exemplified by di-tert-butyl hydroxy silyl phenyl ether) can be converted to a 1,2-dihydroxy aromatic moiety (for example, catechol as derived from the phenol derivative). In some embodiments, this step comprises further contacting the aromatic hydroxy silyl ether (as exemplified by di-tert-butyl hydroxy silyl phenyl ether) with an acetoxylating reagent in the presence of a palladium catalyst to form to the 1,2-dihydroxy aromatic moiety (for example, catechol as derived from the phenol derivative). Again, without intending to limit the definition of the substitution of the substrates, in certain embodiments, the aromatic silyl ether has a structure of Formula (VII), or a corresponding structure for other aromatic analogs, where n is 0, 1, 2, 3, 5, or 5, and $R^A$ are described as elsewhere herein, and the corresponding catechol (or other aromatic 1,2-diol) of Formula (IX) is correspondingly substituted. In certain of these embodiments, the acetoxylating reagent is or comprises $PhI(OAc)_2$ and the palladium catalyst comprises a dicarboxylate of palladium (II). In the reactions described herein as comprising a dicarboxylate of palladium (II) (or copper carboxylate, as discussed below), the carboxylate can be any alkyl or aryl carboxylate, though typically in such reactions, acetates, benzoates, or pivalates are used. These reactions are analogous to those described in Huang, *J. Am. Chem. Soc.*, 2011, 133 (44), 17630-17633, which describes this transformation as a highly site-selective silanol-directed, Pd-catalyzed C—H oxygenation of phenols into catechols that operates via a silanol-directed acetoxylation, followed by a subsequent acid-catalyzed cyclization reaction into a cyclic silicon-protected catechol. The desilylation of the silacyle with TBAF to uncover the catechol product is described as routine. Exemplary reaction conditions in this reference includes reacting the 3-methyl derivative of the compound of Formula (VII) with $Pd(OPiv)_2$ (5 mol %), $PhI(OAc)_2$ (2 eq) in toluene at 100° C., for 6-12 hrs, followed by reaction with TBAF in THF. Such a reaction may be represented schematically as:

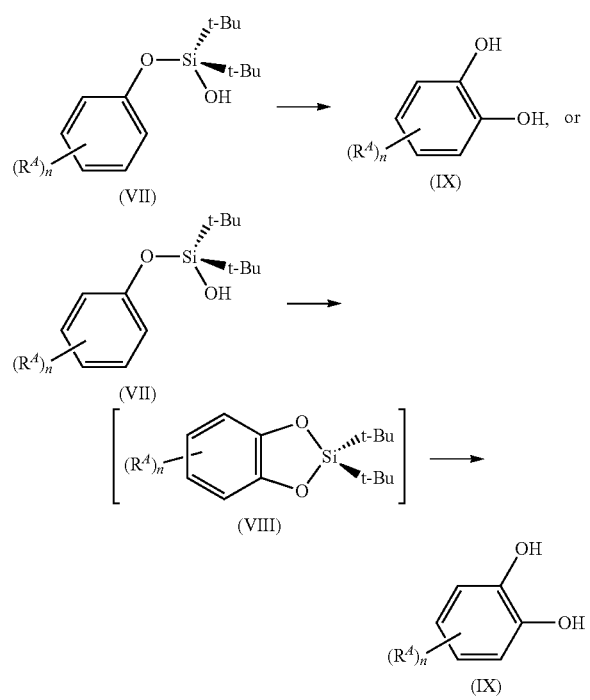

In other embodiments, the aromatic hydroxy silyl ether (as exemplified by di-tert-butyl hydroxy silyl phenyl ether) can be converted to an ortho-alkenylated aromatic alcohol (e.g., an ortho-alkenylated phenol). In some embodiments, this step comprises further contacting the aromatic hydroxy silyl ether (as exemplified by di-tert-butyl hydroxy silyl phenyl ether) with a terminal olefin in the presence of a palladium catalyst to form the ortho-alkenylated product. Again, without intending to limit the definition of the substitution of the substrates, in certain embodiments the terminal olefin has a structure comprising Formula (X):

where $R^B$ is H or $C_{1-12}$ alkyl and $R^C$ is aldehyde, —C(O)—$C_{1-12}$ alkyl, —C(O)—O$C_{1-12}$ alkyl, —S(O)$_2$—$C_{1-12}$ alkyl, —S(O)$_2$—$C_{6-24}$ aryl, —S(O)$_2$—O$C_{1-12}$ alkyl, —S(O)$_2$—O$C_{6-24}$ aryl, optionally substituted (with one or more halo or $C_{1-6}$ alkyl) phenyl, or an optionally substituted 5- or 6-membered heterocyclic group.

In some independent embodiments, the aromatic hydroxy silyl ether has a structure corresponding to the compound of Formula (VII), the ortho-alkenylated product has a structure corresponding to the compound of Formula (XI), where n is 0, 1, 2, 3, 5, or 5, and $R^A$ are described elsewhere herein, and the corresponding ortho-alkenylated product is correspondingly substituted. In certain of these embodiments, the palladium catalyst comprises a dicarboxylate of palladium (II) as described above. For phenols, C. Huang, et al., *J. Am. Chem. Soc.*, 2011, 133 (32), pp 12406-12409 describes this transformation as silanol-directed, Pd(II)-catalyzed ortho-C—H alkenylation of phenols. Exemplary reaction conditions in this reference includes reacting the 3,4-dimethyl derivative of the compound of Formula (VII) with a variety of functionalized terminal olefins (2-4 equiv) in the presence of $Pd(OAC)_2$ (10 mol %), (+)menthyl($O_2$C)-Leu-OH (20 mol %)), $Li_2CO_3$ (1 equiv), and AgOAc (4 equiv), in $C_6F_6$ at 100° C., followed by routine desilylation using TBAF/THF. Such a reaction may be represented schematically as:

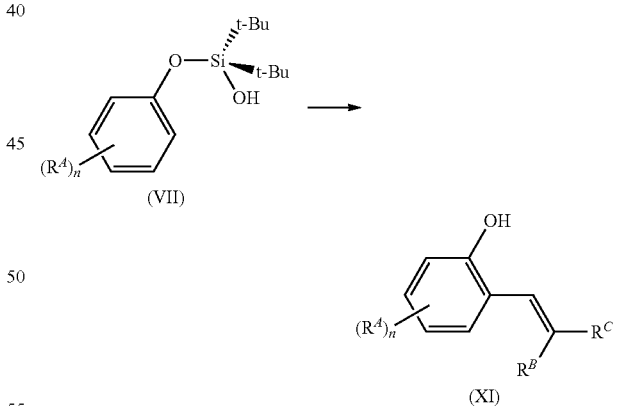

In sill other embodiments, the aromatic hydroxy silyl ether (again, as exemplified by di-tert-butyl hydroxy silyl phenyl ether) can be converted to an ortho-carboxylic acid aromatic alcohol. In certain aspects of these embodiments, this step further comprises contacting the aromatic hydroxy silyl ether with carbon monoxide (CO) in the presence of a palladium catalyst to form an ortho-carboxylic acid phenol. Each of the hydroxy and carboxy functional groups may be further functionalized by any means suitable for those functional groups. Again, without intending to limit the definition of the substitution of the substrates, in certain embodiments, the aromatic silyl ether has a structure of Formula (VII), or a corresponding structure for other aromatic analogs, where n is 0, 1, 2, 3, 5, or 5, and $R^A$ are described as elsewhere herein, and the corresponding ortho-carboxylic acid alcohol (as exemplified in Formula (XIII) is correspondingly substituted. This transformation for the phenol derivative is described in Y. Wang, et al., *Angew Chem Int Ed Engl.* 2015 Feb. 9; 54(7): 2255-2259. Exemplary reaction conditions in this reference includes reacting the 3-tert-butyl derivative of the compound of Formula (VII) with CO in the presence of Pd(OAC)$_2$ (10 mol %), Boc-Leu-OH (20 mol %)), AgOAc (3 equiv), and CF$_3$CH$_2$OH (3 equiv) in dichloroethane at 95° C. for 18 hours, to form the cyclic derivative corresponding to Formula (XII), followed by routine desilylation using TBAF/THF to form the salicyclic derivative (Formula (XIII)). Such a reaction may be represented schematically as:

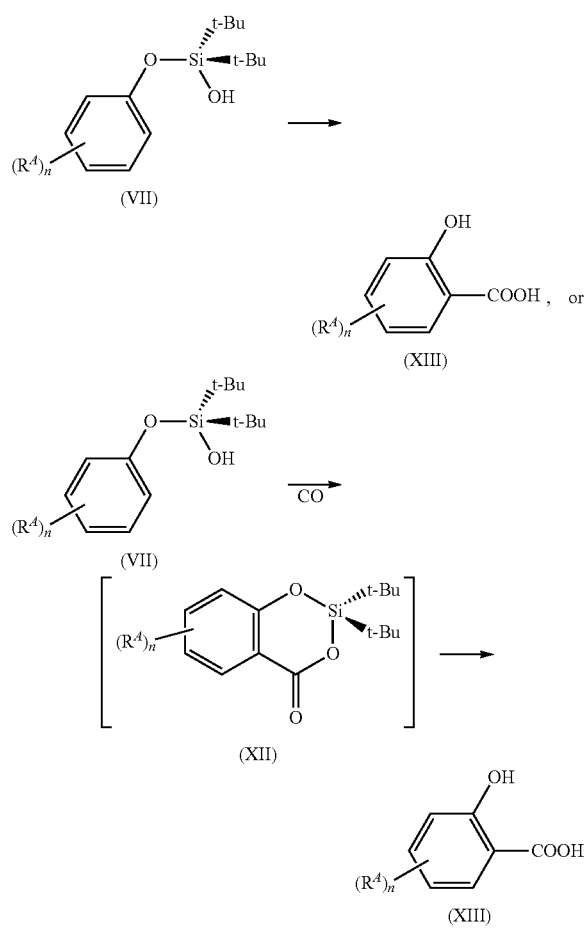

As described in another section and exemplified herein, the reaction of dihydrosilanes with diols (or polyols) provides entry into another class of cyclic dioxasilolane derivatives, and as shown in the Examples, such chemistries can afford useful synthons for a range of chemical transformations. As such, further embodiments include those where the products derived by the inventive methods discussed herein are further subjected to conditions conducive to these downstream transformations. Some of these are described as follows.

In some embodiments, the dihydrosilane may be described in terms of a structure $(R^J)(R^K)Si(H)_2$, where $R^J$ comprises an optionally substituted phenyl, optionally substituted naphthyl, or optionally substituted 5- or 6-membered heteroaryl moiety and where $R^K$ is a $C_{1-3}$ alkyl. More broadly, $R^J$ represents a moiety suitable for transfer to a suitable substrate when the corresponding cyclic dioxasilolane is used for that application (for example, the definition of $R^J$ may further include allyl) and $R^K$ is not.

In some embodiments, then $R^K$ is methyl. In other independent embodiments, the organic substrate having at least one organic alcohol moiety is a compound of Formula (IIIB) as described above, or a compound of structure (IV)

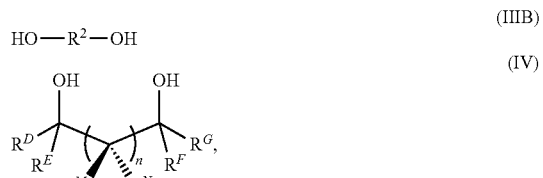

the product of the reaction comprising a cyclic dioxasilolane. In certain Aspects of this Embodiment, the product cyclic dioxasilolane has a structure of Formula (XV); wherein n is from 0 to 6; and $R^D$, $R^E$, $R^F$, and $R^G$ are independently H, $C_{1-6}$ alkyl, optionally substituted phenyl, optionally substituted benzyl, optionally substituted 5- or 6-ring membered heteroaryl, wherein the optional substituents are described elsewhere. In some embodiments, the optional substituents are $C_{1-3}$ alkyl, $C_{1-3}$ alkoxy, or halo. The reaction may be represented schematically as:

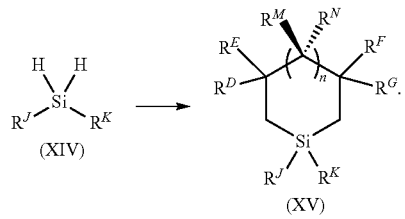

Where $R^K$ is methyl, this becomes:

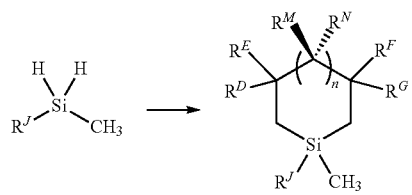

In some embodiments, $R^J$ comprises an optionally substituted phenyl. In other embodiments, the organic substrate having at least one organic alcohol moiety is optionally substituted 3-phenyl-butane-1,3-diol, 2,2-dimethyl-propane-1,3-diol, catechol, or pinacol. Without intending to necessarily limit the substituent pattern on the optionally substituted phenyl, in some embodiments, the structures of Formula (XIV) may be characterized as having the structure of Formula (XIV-A) and the product of the method as having a structure of any one of Formulae (XV-A), (XV-A1), (XV-A2), or (XV-A3), where $(R^A)_n$ is defined elsewhere herein.

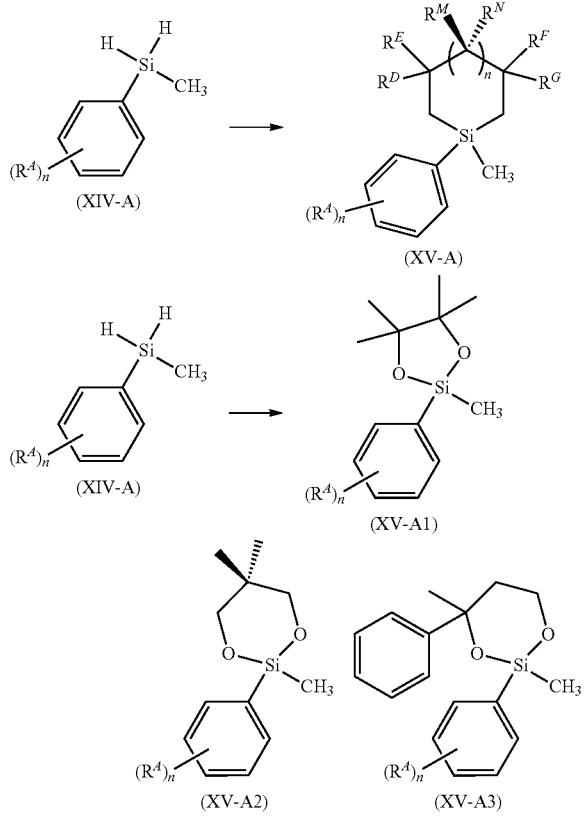

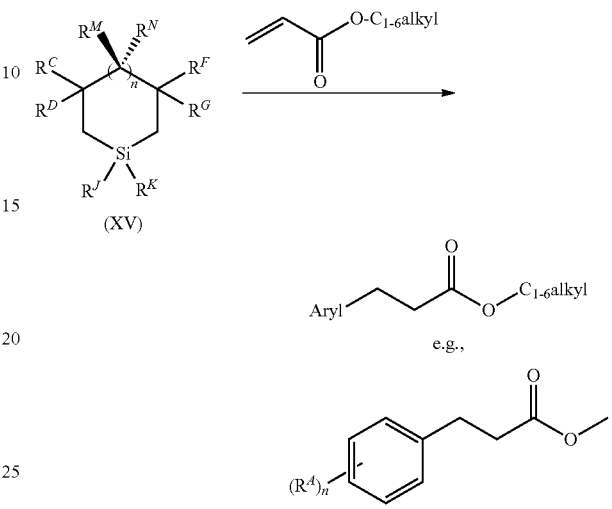

Likewise, any of the cyclic dioxasilolanes described herein by the formula $(R^J)(R^K)Si(H)_2$, whether prepared by the inventive methods or otherwise, may further be used in rhodium catalyzed coupling reactions to form beta-aromatic substituted $C_{1-6}$ propionate ester products:

For example, in some embodiments, the method comprises reacting the compound of Formula (XV) with $C_{1-6}$ acrylate ester in the presence of a rhodium catalyst under conditions sufficient to couple the aromatic $R^J$ moiety with the $C_{1-6}$ acrylate ester to form a beta-aromatic substituted $C_{1-6}$ propionate ester product. Exemplary rhodium catalysts include $[Rh(cyclooctadiene)Cl]_2$ and $[Rh(cyclooctene)_2Cl]_2$. Such reactions are described in C. Cheng and J. F. Hartwig, Science, 343 (6173), 853-857 (2014). Exemplary reaction conditions include the reaction of $(phenyl)SiMe(OTMS)_2$ with tert-butyl acrylate (0.5 equiv), $[Rh(cod)Cl]_2$ (0.02 equiv), TBAF (3 equiv), THF, $H_2O$, 100° C., 14 hours.

Any of the cyclic dioxasilolanes described herein by the formula $(R^J)(R^K)Si(H)_2$, whether prepared by the inventive methods or otherwise, may further be used in palladium catalyzed coupling reactions to form biaromatic compounds. In certain embodiments, these cyclic dioxasilolanes, for example as represented by the compound of Formula (XV) may be contacted with an aromatic bromide or iodide in the presence of a palladium catalyst under conditions sufficient to couple the aromatic $R^J$ moiety to the aromatic bromide or iodide to form a biaromatic product. In this context, the representation of Formula (XV) independently embodies any of the subgenera or specific compounds encompassed by this structure:

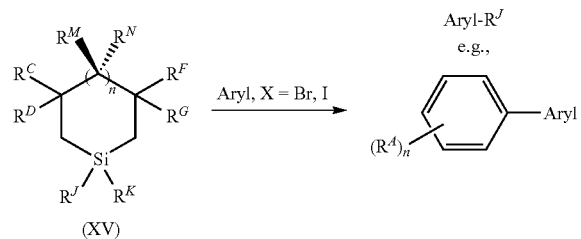

Similar reactions using disiloxane precursors (and not the cyclic dioxasilolanes of the instant invention) are described in C. Cheng and J. F. Hartwig, Science, 343 (6173), 853-857 (2014). Exemplary reaction conditions in this reference include the reaction of $(phenyl)SiMe(OTMS)_2$ with PhBr or 3-iodoanisole (0.7 to 1.5 equiv), KOTMS (3 equiv), $Pd(OAc)_2$ (0.05 equiv), dcpe (1,2-bis(dicyclohexylphosphino)ethane; 0.055 equiv), THF or toluene, 65 to 100° C., 5 to 14 hours.

Likewise, any of the cyclic dioxasilolanes described herein by the formula $(R^J)(R^K)Si(H)_2$, whether prepared by the inventive methods or otherwise, may further be used to couple $R^J$ with substituted benzimidazoles. In some embodiment, this involves the use of copper catalysts. For example, in some embodiments, this reaction comprises reacting the compound of Formula (XV) with an optionally substituted benzimidazole in the presence of a copper catalyst under conditions sufficient to aminate the benzimidazole with the aromatic $R^J$ moiety. Exemplary copper catalysts include copper carboxylates, where the carboxylates may include acetates, benzoates, and pivalates. Such reactions are described in C. Cheng and J. F. Hartwig, Science, 343 (6173), 853-857 (2014): Exemplary conditions are provided in this reaction for the reaction of $(phenyl)SiMe(OTMS)_2$ with benzimidazole (0.5 equiv), $Cu(OAc)_2$ (0.6 equiv), TBAF (1 equiv), dimethylformamide (DMF), 23° C., 36 hours.

The references to C. Cheng and J. F. Hartwig, Science, 343 (6173), 853-857 (2014), J. Am. Chem. Soc., 2011, 133 (32), pp 12406-12409, Huang, J. Am. Chem. Soc., 2011, 133 (44), 17630-17633, C. Huang, et al., and Y. Wang, et al., Angew Chem Int Ed Engl. 2015 Feb. 9; 54(7): 2255-2259 are incorporated by reference herein in their entireties, or at least for their teachings of the described transformations and the materials and conditions used for the same.

Compositions

The inventive concepts have been thusfar described in terms of the methods of dehydrogenatively decoupling hydrosilanes and alcohols to form silyl ethers. It should be appreciated that the products obtained from such methods, to the extent that they are not practically available by other means known at the time of this filing, and the composition or systems used in these methods, are all considered within the scope of the present disclosure.

Again, the scope of the present disclosure includes embodiments for any composition used or generated in any of these inventive methods. These compositions, in various embodiments, include the hydrosilanes, alcohols, sodium and/or potassium hydroxide, and optionally any of the products resulting from the reactions. For example, certain embodiments provide compositions comprising or consisting essentially of (a) at least one hydrosilane; (b) sodium and/or potassium hydroxide; (c) an organic substrate having at least one organic alcohol moiety; and optionally (d) a silyl ether resulting from the dehydrogenative coupling of the at least one hydrosilane and the at least one alcohol moiety. In other embodiments, the silyl ether resulting from the dehydrogenative coupling is present. In still other embodiments, the compositions comprise any of the aprotic polar solvents described as useful in the inventive methods.

As related to the compositions and methods, the term "consisting essentially of" refers compositions whose basic and novel characteristic(s) are those named ingredients necessary for the progress of the reaction, as defined herein, but which may also contain other ingredients which do not affect the progression of the reaction. For example, a composition consisting essentially of the four ingredients (a-d) might also contain a colorant, as such a material would not be expected to have any effect on the progress of the inventive methods, but it would not contain, for example, transition metal catalysts, ions, or compounds, "superbases," such as alkoxides, hydrides, alkyl lithium reagents, or any chemical known to enhance the activity of the NaOH or KOH (e.g., crown ethers), and/or fluoride ion. While such materials are known to promote such dehydrogenative coupling reactions as described herein, they are not necessary or desirable in the present context, and in preferred embodiments, they are completely or substantially free these materials.

In the context of these compositions, various embodiments include those compositions comprising any genus, species, or individual of the hydrosilane, alcohol, and silyl ether described herein, in any combination or permutations. These include, but are not limited to, the hydrosilanes having a genus structure of Formulae (I), (II), (XIV), (XIV-A), $(R^J)(R^K)Si(H)_2$, or any subgenus or example thereof. In other various embodiments, the compositions include one or more of the alcohols described herein as useful in the methods, including by not limited to the substrates defined by the genus structures of Formulae (IIIA), (IIIB), (IV), (V), (V-A), (V-B) or any subgenus or example thereof. In other various embodiments, the compositions include one or more of the dehydrogenatively coupled silyl ethers described herein, including by not limited to the substrates defined by the genus structures of Formulae (VI), (VI-A), (VI-B), (XV), (XV-A), (XV-A1), (XV-A2), or (XV-A3) or any subgenus or example thereof.

Terms

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art.

When a value is expressed as an approximation, for example by use of the descriptor "about," it will be understood that the particular value forms another embodiment. In general, use of a term such as "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others. For example, where method steps are described as building from previous steps, it is intended that each individual step is an independent embodiment, without the necessary use of the recited precursor step.

The transitional terms "comprising," "consisting essentially of" and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps and those that do not materially affect the basic and novel characteristic(s) of the claimed invention. Embodiments described in terms of the phrase "comprising" (or its equivalents), also provide, as embodiments, those which are independently described in terms of "consisting of" and "consisting essentially of" For those embodiments provided in terms of "consisting essentially of" the basic and novel characteristic(s) is the facile operability of the methods to provide silylated products at meaningful yields (or the ability of the systems used in such methods to provide the product compositions at meaningful yields or the compositions derived therefrom); i.e., to dehydrogenatively couple hydrosilanes and alcohols to form silyl ethers using only those ingredients listed. The term "consisting essentially of" has been further discussed elsewhere herein.

The term "meaningful product yields" is intended to reflect product yields of greater than 20%, but when specified, this term may also refer to yields of 10%, 20%, 30%, 40%, 50%, 60%, 70%, 80%, or 90% or more, relative to the amount of original substrate.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C." Similarly, a designation such as $C_{1-3}$ includes not only $C_{1-3}$, but also $C_1$, $C_2$, $C_3$, $C_{1-2}$, $C_{2-3}$, and $C_{1,3,}$ as separate embodiments.

Throughout this specification, words are to be afforded their normal meaning, as would be understood by those skilled in the relevant art. However, so as to avoid misunderstanding, the meanings of certain terms will be specifically defined or clarified.

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, sec-butyl, isobutyl, tert-butyl, octyl, decyl, and the like, as well as cycloalkyl groups such as cyclopentyl, cyclohexyl and the like. Generally, although again not necessarily, alkyl groups herein contain 1 to about 12 carbon atoms. The term also includes "lower alkyl" as separate embodiments, which refers to an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl groups substituted with one or more substituent groups, and the terms "heteroatom-containing alkyl" and "heteroalkyl" refer to alkyl groups in which at least one carbon atom is replaced with a heteroatom, for example providing at least one amino, ether, sulfide, sulfoxide, sulfone, phosphino, phosphate, or phosphite linkage. If not otherwise indicated, the terms "alkyl" and "lower alkyl" include linear, branched, cyclic, unsubstituted, substituted, and/or heteroatom-containing alkyl and lower alkyl groups, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term also includes "lower alkenyl" as separate embodiments, which refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl groups substituted with one or more substituent groups, and the terms "heteroatom-containing alkenyl" and "heteroalkenyl" refer to alkenyl groups in which at least one carbon atom is replaced with a heteroatom, as described above for "alkyl." If not otherwise indicated, the terms "alkenyl" and "lower alkenyl" include linear, branched, cyclic, unsubstituted, substituted, and/or heteroatom-containing alkenyl and lower alkenyl groups, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term also includes "lower alkynyl" as separate embodiments, which refers to an alkynyl group substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include a linear, branched, unsubstituted, substituted, and/or heteroatom-containing alkynyl and lower alkynyl group, respectively.

The term "alkoxy" as used herein intends an alkyl group bound through a single, terminal ether linkage; that is, an "alkoxy" group may be represented as —O-alkyl where alkyl is as defined above. The term also includes "lower alkoxy" as separate embodiments, which refers to an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aromatic" refers to the ring moieties which satisfy the Hüuckel 4n+2 rule for aromaticity, and includes both aryl (i.e., carbocyclic) and heteroaryl (also called heteroaromatic) structures, including aryl, aralkyl, alkaryl, heteroaryl, heteroaralkyl, or alk-heteroaryl moieties, or pre-polymeric (e.g., monomeric, dimeric), oligomeric or polymeric analogs thereof.

The term "aryl" as used herein, and unless otherwise specified, refers to a carbocyclic aromatic substituent or structure containing a single aromatic ring or multiple aromatic rings that are fused together, directly linked, or indirectly linked (such that the different aromatic rings are bound to a common group such as a methylene or ethylene moiety). Preferred aryl groups contain 6 to 24 carbon atoms, and particularly preferred aryl groups contain 6 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail elsewhere herein. Exemplary embodiments of heteroaryl moieties or compounds include furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, or dibenzothiophene compound or moiety.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 6 to 24 carbon atoms, and particularly preferred aryloxy groups contain 6 to 14 carbon atoms. Examples of aryloxy groups include, without limitation, phenoxy, o-halo-phenoxy, m-halo-phenoxy, p-halophenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 7 to 24 carbon atoms, and particularly preferred alkaryl and aralkyl groups contain 7 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl," and "aralkyl" are as defined above.

The terms "cyclic" and "ring" refer to alicyclic or aromatic groups that may or may not be substituted and/or heteroatom-containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic. The term "acyclic" refers to a structure in which the double bond is not contained within a ring structure.

The terms "halo," "halide," and "halogen" are used in the conventional sense to refer to a chloro, bromo, fluoro, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated, and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Non-limiting examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

As used herein, the terms "substrate" or "organic substrate" are intended to connote both discrete small molecules (sometimes described as "organic compounds") and oligomers and polymers containing an alcoholic hydroxy group. The term "aromatic moieties" is intended to refer to those portions of the compounds, pre-polymers (i.e., monomeric compounds capable of polymerizing), oligomers, or polymers having at least one of the indicated aromatic structures. Where shown as structures, the moieties contain at least that which is shown, as well as containing further functionalization, substituents, or both, including but not limited to the functionalization described as "Fn" herein.

By "substituted" as in "substituted hydrocarbyl," "substituted alkyl," "substituted aryl," and the like, as alluded to in some of the aforementioned definitions, is meant that in the hydrocarbyl, alkyl, aryl, heteroaryl, or other moiety, at least one hydrogen atom bound to a carbon (or other) atom is replaced with one or more non-hydrogen substituents. Examples of such substituents include, without limitation: functional groups referred to herein as "Fn," such as halo (e.g., F, Cl, Br, I), hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_1$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl ((C))—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ alkyl)), di-($C_1$-$C_{24}$ haloalkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—NH$_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl),N—($C_5$-$C_{24}$ aryl)-substituted thiocarbamoyl, carbamido (—NH—(CO)—NH$_2$), cyano(-C≡N), cyanato (—O—C≡N), thiocyanato (—S—C≡N), formyl (—(CO)—H), thioformyl (—(CS)—H), amino (—NH$_2$), mono-(C$_1$-C$_{24}$ alkyl)-substituted amino, di-(C$_1$-C$_{24}$ alkyl)-substituted amino, mono-(C$_5$-C$_{24}$ aryl)substituted amino, di-(C$_5$-C$_{24}$ aryl)-substituted amino, C$_1$-C$_{24}$ alkylamido (—NH—(CO)-alkyl), C$_6$-C$_{24}$ arylamido (—NH—(CO)-aryl), imino (—CR=NH where R=hydrogen, C$_1$-C$_{24}$ alkyl, C$_5$-C$_{24}$ aryl, C$_6$-C$_{24}$ alkaryl, C$_6$-C$_{24}$ aralkyl, etc.), C$_2$-C$_{20}$ alkylimino (—CR=N(alkyl), where R=hydrogen, C$_1$-C$_{24}$ alkyl, C$_5$-C$_{24}$ aryl, C$_6$-C$_{24}$ alkaryl, C$_6$-C$_{24}$ aralkyl, etc.), arylimino (—CR=N(aryl), where R=hydrogen, C$_1$-C$_{20}$ alkyl, C$_5$-C$_{24}$ aryl, C$_6$-C$_{24}$ alkaryl, C$_6$-C$_{24}$ aralkyl, etc.), nitro (—NO$_2$), nitroso (—NO), sulfo (—SO$_2$OH), sulfonate (SO$_2$O—), C$_1$-C$_{24}$ alkylsulfanyl (—S-alkyl; also termed "alkylthio"), C$_5$-C$_{24}$ arylsulfanyl (—S-aryl; also termed "arylthio"), C$_1$-C$_{24}$ alkylsulfinyl (—(SO)-alkyl), C$_5$-C$_{24}$ arylsulfinyl (—(SO)-aryl), C$_1$-C$_{24}$ alkylsulfonyl (—SO$_2$-alkyl), C$_1$-C$_{24}$ monoalkylaminosulfonyl-SO$_2$—N(H) alkyl), C$_1$-C$_{24}$ dialkylaminosulfonyl-SO$_2$—N(alkyl)$_2$, C$_5$-C$_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O—)$_2$), phosphinato (P(O)(O—)), phospho (—PO$_2$), and phosphine (—PH$_2$); and the hydrocarbyl moieties C$_1$-C$_{24}$ alkyl (preferably C$_1$-C$_{12}$ alkyl, more preferably C$_1$-C$_6$ alkyl), C$_2$-C$_{24}$ alkenyl (preferably C$_2$-C$_{12}$ alkenyl, more preferably C$_2$-C$_6$ alkenyl), C$_2$-C$_{24}$ alkynyl (preferably C$_2$-C$_{12}$ alkynyl, more preferably C$_2$-C$_6$ alkynyl), C$_5$-C$_{24}$ aryl (preferably C$_5$-C$_{24}$ aryl), C$_6$-C$_{24}$ alkaryl (preferably C$_6$-C$_{16}$ alkaryl), and C$_6$-C$_{24}$ aralkyl (preferably C$_6$-C$_{16}$ aralkyl). Within these substituent structures, the "alkyl," "alkylene," "alkenyl," "alkenylene," "alkynyl," "alkynylene," "alkoxy," "aromatic," "aryl," "aryloxy," "alkaryl," and "aralkyl" moieties may be optionally fluorinated or perfluorinated. Additionally, reference to alcohols, aldehydes, amines, carboxylic acids, ketones, or other similarly reactive functional groups also includes their protected analogs. For example, reference to hydroxy or alcohol also includes those substituents wherein the hydroxy is protected by acetyl (Ac), benzoyl (Bz), benzyl (Bn), β-Methoxyethoxymethyl ether (MEM), dimethoxytrityl, [bis-(4-methoxyphenyl)phenylmethyl] (DMT), methoxymethyl ether (MOM), methoxytrityl [(4-methoxyphenyl)diphenylmethyl, MMT), p-methoxybenzyl ether (PMB), methylthiomethyl ether, pivaloyl (Piv), tetrahydropyranyl (THP), tetrahydrofuran (THF), trityl (triphenylmethyl, Tr), silyl ether (most popular ones include trimethylsilyl (TMS), tert-butyldimethylsilyl (TBDMS), tri-iso-propylsilyloxymethyl (TOM), and triisopropylsilyl (TIPS) ethers), ethoxyethyl ethers (EE). Reference to amines also includes those substituents wherein the amine is protected by a BOC glycine, carbobenzyloxy (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), carbamate, p-methoxybenzyl (PMB), 3,4-dimethoxybenzyl (DMPM), p-methoxyphenyl (PMP), tosyl (Ts) group, or sulfonamide (Nosyl & Nps) group. Reference to substituent containing a carbonyl group also includes those substituents wherein the carbonyl is protected by an acetal or ketal, acylal, or diathane group. Reference to substituent containing a carboxylic acid or carboxylate group also includes those substituents wherein the carboxylic acid or carboxylate group is protected by its methyl ester, benzyl ester, tert-butyl ester, an ester of 2,6-disubstituted phenol (e.g. 2,6-dimethylphenol, 2,6-diisopropylphenol, 2,6-di-tert-butylphenol), a silyl ester, an orthoester, or an oxazoline. Preferred substituents are those identified herein as not or less affecting the silylation chemistries, for example, including those substituents comprising alkyls; alkoxides, aryloxides, aralkylalkoxides, protected carbonyl groups; aryls optionally substituted with F, Cl, —CF$_3$; epoxides; N-alkyl aziridines; cis- and trans-olefins; acetylenes; pyridines, primary, secondary and tertiary amines; phosphines; and hydroxides.

By "functionalized" as in "functionalized hydrocarbyl," "functionalized alkyl," "functionalized olefin," "functionalized cyclic olefin," and the like, is meant that in the hydrocarbyl, alkyl, aryl, heteroaryl, olefin, cyclic olefin, or other moiety, at least one hydrogen atom bound to a carbon (or other) atom is replaced with one or more functional groups such as those described herein and above. The term "functional group" is meant to include any of the substituents described herein with the ambit of "Fn.".

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom or organic moiety, and, thus, the description includes structures wherein a non-hydrogen substituent is present and structures wherein a non-hydrogen substituent is not present.

As used herein, the terms "organosilane" or "hydrosilane" may be used interchangeably and refer to a compound or reagent having at least one silicon-hydrogen (Si—H) bond and preferably at least one carbon-containing moiety. The organosilane may further contain a silicon-carbon, a silicon-oxygen (i.e., encompassing the term "organosiloxane"), a silicon-nitrogen bond, a silicon-silicon, or a combination thereof, and may be monomeric, dimeric (disilane) or contained within an oligomeric or polymeric framework, including being tethered to a heterogeneous or homogeneous support structure.

As used herein, the terms "hydrodisilane," "organodisilane" and "disilane" are used interchangeably and refer to a compound or reagent having at least one Si—Si bond. These terms include those embodiments where the disilane contains at least one Si—H bond. The organodisilane may further contain a silicon-carbon, a silicon-oxygen, a silicon-nitrogen bond, or a combination thereof, and may be monomeric, or contained within an oligomeric or polymeric framework, including being tethered to a heterogeneous or homogeneous support structure.

As used herein, unless explicitly stated to the contrary, the hydrosilanes or hydrodisilanes are intended to refer to materials that contain no Si-halogen bonds. However, in some embodiments, the hydrosilanes or hydrodisilanes may contain a Si-halogen bond.

As used herein, the terms "dehydrogenative coupling," "silylating" or "silylation" refer to the forming of silicon-oxygen bonds. As the name suggests, dehydrogenative coupling may be seen as coupling of a O—H and Si—H bond to form a O—Si bond, with the release of H$_2$.

As used herein, the term "substantially free" or "substantially absence of," for example, of a transition-metal compound (or any of the other materials to which this term is applied), is intended to reflect that the system is effective for its intended purpose of dehydrogenative coupling hydrosilanes and alcohols under the relatively mild conditions described herein, even in the absence of any exogenous (i.e., deliberately added or otherwise) materials, in this case transition-metal catalyst(s). While certain embodiments provide that transition metals, including those capable of catalyzing silylation reactions, may be present within the systems or methods described herein at levels normally associated with such catalytic activity (for example, in the case where the substrates comprise metallocenes), the presence of such metals (either as catalysts or spectator compounds) is not required and in many cases is not desirable. As such, in many preferred embodiments, the system and methods are at least "substantially free," if not completely free of transition-metal compounds (or the other materials to which this term is directed). Unless otherwise stated, then, the term "substantially free of a transition-metal compound" is defined to reflect the absence of deliberately added materials (transition metals or the other materials to which this term is applied). In other specified embodiment, the term "substantially free" refers to a condition in which the total level of transition metal (or the other materials) in the reaction medium, independently or in the presence of organic substrate, is less than about 5 ppm, as measured by ICP-MS. When expressly stated as such, additional embodiments also provide that the concentration of transition metals (or the other materials) is less than about 10 wt %, 5 wt %, 1 wt %, 100 ppm, 50 ppm, 30 ppm, 25 ppm, 20 ppm, 15 ppm, 10 ppm, or 5 ppm to about 1 ppm or 0 ppm. As used herein, the term "transition metal" is defined to include d-block elements, for example Ag, Au, Co, Cr, Rh, Ir, Fe, Ru, Os, Ni, Pd, Pt, Cu, Zn, or combinations thereof. In further specific independent embodiments, the concentration of Ni, as measured by ICP-MS, is less than 25 ppm, less than 10 ppm, less than 5 ppm, or less than 1 ppm. The term "substantially free" is applied in this context to superbases, fluoride ions, and crown ethers. As used herein, the terms "crown ether" is intended to encopass "cryptands" and other cyclic or caged material containing several ether groups capable of binding sodium and especially potassium cations, for example 12-crown-4, 15-crown-5, 18-crown-6, dibenzo-18-crown-6, diaza-18-crown-6, and 2.2.2-cryptand materials. In preferred embodiments, the presence of these types of chelants, or other similar Na$^+$ or K$^+$ selective binding agents are absent While it may not be necessary to limit the system's exposure to water and oxygen, in some embodiments, the chemical systems and the methods are done in an environment substantially free of water, oxygen, or both water and oxygen. In other embodiments, air and/or water are present. Unless otherwise specified, the term "substantially free of water" refers to levels of water less than about 500 ppm and "substantially free of oxygen" refers to oxygen levels corresponding to partial pressures less than 1 torr. Where stated, additional independent embodiments may provide that "substantially free of water" refers to levels of water less than 1.5 wt %, 1 wt %, 0.5 wt %, 1000 ppm, 500 ppm, 250 ppm, 100 ppm, 50 ppm, 10 ppm, or 1 ppm and "substantially free of oxygen" refers to oxygen levels corresponding to partial pressures less than 50 torr, 10 torr, 5 torr, 1 torr, 500 millitorr, 250 millitorr, 100 millitorr, 50 millitorr, or 10 millitorr. In the General Procedure described herein, deliberate efforts were made to exclude both water and oxygen, unless otherwise specified.

The term "silyl ether" refers to product of the reactions as described herein, comprising at least one C—O—Si linkage, as would be understood by those skilled in the art.

The following listing of embodiments is intended to complement, rather than displace or supersede, the previous descriptions.

Embodiment 1. A method comprising contacting substrate (preferably an organic substrate) having at least one hydroxy (e.g., organic alcohol) moiety with a mixture of at least one hydrosilane and a sodium and/or potassium hydroxide, the contacting resulting in the formation of a dehydrogenatively coupled silyl ether. In related Aspects of this Embodiment, the substrate is or comprises an inorganic substrate, such as a hydrated oxide (e.g., of alumina, silica, titania, or zirconia) or water. In the former case, the product is a silylated inorganic surface; in the latter case, the product is a siloxane, for example, a mono-, di-, or polysilane and/or a cyclic polysiloxane. In certain Aspects of this Embodiment, the method is conducted in the complete or substantial absence of transition metal ions, compounds, or catalysts. In other Aspects of this Embodiment, the methods are conducted in the substantial absence of "superbases," such as alkoxides, hydrides, alkyl lithium, anionic amides, or phosphines reagents, or any chemical known to enhance the activity of the NaOH or KOH (e.g., crown ethers or cryptands). In other Aspects of this Embodiment, the methods are conducted in the complete or substantial absence of fluoride ion (typically present as tetraalkyl ammonium fluoride, for example). In still other Aspects of this Embodiment, the methods are conducted using aprotic polar solvents such as acetonitrile, dimethylacetamide, dimethyl formamide, dimethylsulfoxide, glycols or polyglycols (including, for example, dimethoxyethane, DME), optionally substituted dioxanes, dialkyl ethers (e.g., diethyl, dimethyl ether), hexamethylphosphoramide (HMPA), optionally substituted THF and furans, and N-methylpyrrolidone (NMP). Oxygen donor solvents, such as THF, optionally in the presence of DMF, have been shown to work well in these reactions.

Embodiment 2. The method of Embodiment 1, wherein the hydrosilane contains at least one Si—H bond and preferably has a structure of Formula (I) or of Formula (II):

where: m is independently 0, 1, or 2; and each R is independently optionally substituted $C_{1-24}$ alkyl or heteroalkyl, optionally substituted $C_2$-24 alkenyl or heteroalkenyl, optionally substituted $C_2$-24 alkynyl or heteroalkynyl, optionally substituted 6 to 18 ring membered aryl or 5 to 18 ring membered heteroaryl, optionally substituted 6 to 18 ring-membered alkaryl or 5 to 18 ring-membered heteroalkaryl, optionally substituted 6 to 18 ring-membered aralkyl or 5 to 18 ring-membered heteroaralkyl, optionally substituted —O—$C_{1-24}$ alkyl or heteroalkyl, optionally substituted 6 to 18 ring-membered aryloxy or 5 to 18 ring-membered heteroaryloxy, optionally substituted 6 to 18 ring-membered alkaryloxy or 5 to 18 ring-membered heteroalkaryloxy, or optionally substituted 6 to 18 ring-membered aralkoxy or 5 to 18 ring-membered heteroaralkoxy, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, 5 to 12 ring-membered arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon. In individual Aspects of this Embodiment, m is 0, m is 1, m is 2. The compounds of Formula (I) and Formula (II) represent independent Aspects of this Embodiment.

Embodiment 3. The method of Embodiment 1 or 2, wherein the hydrosilane is $(R)_3SiH$, $(R)_2SiH_2$, or $(R)SiH_3$, where R is independently $C_{1-6}$alkoxy, $C_{1-6}$alkyl, $C_{2-6}$alkenyl, $C_{6-24}$aryl, $C_{7-25}$aryloxy, a 5- of 6-ring membered heteroaryl, aralkyl, or heteroaralkyl compound or moiety.

Embodiment 4. The method of any one of Embodiments 1 to 3, wherein the alkali metal hydroxide is sodium hydroxide (NaOH).

Embodiment 5. The method of any one of Embodiments 1 to 4, wherein the alkali metal hydroxide is potassium hydroxide (KOH). It should be appreciated that in these Embodiments, the KOH is present and used in the absence of crown ether or other hydroxide activating chemistries.

Embodiment 6. The method of any one of Embodiments 2 to 5, wherein the hydrosilane is a hydrosilane of Formula (I), where m is 1.

Embodiment 7. The method of any one of Embodiments 2 to 5, wherein the hydrosilane is a hydrosilane of Formula (I), where m is 2.

Embodiment 8. The method of any one of Embodiments 1 to 7, wherein the hydrosilane is $EtMe_2SiH$, $Et_3SiH$, $(n-Bu)_3SiH$, $(i-Pr)_3SiH$, $Et_2SiH_2$, $Ph_2MeSiH$, $(t-Bu)Me_2SiH$, $(t-Bu)_2SiH_2$, $PhMeSiH_2$, $PhMe_2SiH$, $BnMe_2SiH$, $(EtO)_3SiH$, $Me_2(pyridinyl)SiH$, $(i-Pr)_2(pyridinyl)SiH$, or $Me_3Si—SiMe_2H$.

Embodiment 9. The method of any one of Embodiments 1 to 8, wherein the organic substrate having at least one organic alcohol moiety has a structure of Formula (IIIA):

$$R^1—OH \quad \text{(IIIA)}$$

where $R^1$ comprises an optionally substituted $C_{1-24}$ alkyl, optionally substituted $C_{2-24}$ alkenyl, optionally substituted $C_{2-24}$ alkynyl, optionally substituted $C_{6-24}$ aryl, optionally substituted $C_{1-24}$ heteroalkyl, optionally substituted 5- or 6-ring membered heteroaryl, optionally substituted $C_{7-24}$ aralkyl, optionally substituted heteroaralkyl, or optionally substituted metallocene.

Embodiment 10. The method of any one of Embodiments 1 to 8, wherein the organic substrate having at least one organic alcohol moiety has structure of Formula (IIIB):

$$HO—R^2—OH \quad \text{(IIIB)},$$

where $R^2$ comprises an optionally substituted $C_{2-12}$ alkylene, optionally substituted $C_{2-12}$ alkenylene, optionally substituted $C_{6-24}$ arylene, optionally substituted $C_{1-12}$ heteroalkylene, or an optionally substituted 5- or 6-ring membered heteroarylene. In certain Aspects of this Embodiment, the organic substrate having at least one organic alcohol moiety is a catechol, a neopentyl-diol, or a pinacol.

Embodiment 11. The method of any one of Embodiments 1 to 8 or 10, wherein the organic substrate having at least one organic alcohol moiety is or comprises an optionally substituted catechol compound or moiety or has a Formula (IV):

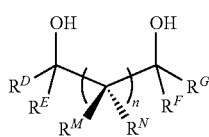

(IV)

wherein n is from 0 to 6;

$R^M$ and $R^N$ are independently H or methyl $R^D$, $R^E$, $R^F$, and $R^G$ are independently H, $C_{1-6}$ alkyl, optionally substituted phenyl, optionally substituted benzyl, optionally substituted 5- or 6-ring membered heteroaryl, wherein the optional substituents are $C_{1-3}$ alkyl, $C_{1-3}$ alkoxy, or halo. In certain Aspects of this Embodiment, the organic substrate include substituted 1,2-diols, 1,3-diols, 1,4-diols, these being substituted with one or more alkyl (including methyl) and/or aryl (including optionally substituted aryl or heteroaryl—e.g., pinacol, 2,4-dimethyl-pentane-2,4-diol, 3-phenyl-butane-1,3-diol, or 2,2-dimethyl-propane-1,3-diol.

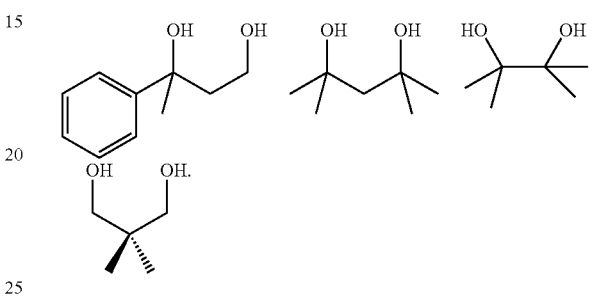

Embodiment 12. The method of any one of Embodiments 1 to 11, wherein the organic substrate having at least one organic alcohol moiety is polymeric.

Embodiment 13. The method of any one of Embodiments 1 to 12, wherein the at least one organic alcohol moiety comprises an aliphatic alcohol moiety.

Embodiment 14. The method of any one of Embodiments 1 to 13, wherein the at least one organic alcohol moiety comprises an aromatic or α-methyl aromatic alcohol moiety.

Embodiment 15. The method of any one of Embodiments 1 to 14, wherein the at least one organic alcohol moiety comprises an optionally substituted benzylic alcohol moiety.

Embodiment 16. The method of Embodiment 14, wherein at least one organic alcohol moiety is an optionally substituted phenol (or other aromatic alcohol moiety) and the at least one hydrosilane is $(tert-butyl)_2Si(H)_2$ (or a similarly bulky dihydrosilane), the reaction product comprising a di-tert-butyl silyl phenyl ether (or corresponding aromatic silyl ether). In related Aspects of this Embodiment, any hydroxylated naphthalene or 5- or 6-membered heteroaryl moiety made stand in place of the phenol. Without intending to limit the definition of the substitution on the phenol, in certain Aspects of this Embodiment, the phenol has a structure of Formula (V), where n is 0, 1, 2, 3, 5, or 5, and $R^A$ is optionally at least one of aldehyde (CHO), $C_{1-6}$ alkyl, $C_{1-6}$ alkylcarbonyl (—C(O)—$C_{1-6}$alkyl), $C_{1-6}$ alkoxy, $C_{1-6}$ alkoxycarbonyl (—C(O)—$C_{1-6}$alkyl), —C(O)—$C_{6-24}$ aryl), —C(O)-5- or 6 membered heteroaryl, halo, nitrile, or nitro. In other Aspects of this Embodiment, n is 2, and two $R^A$'s together with the phenyl ring form a fused 5- or 6 membered carbocyclic ring or 5- or 6 membered mono- or diether ring. Such a reactions may be represented schematically as:

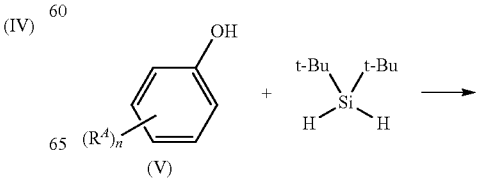

(V)

-continued

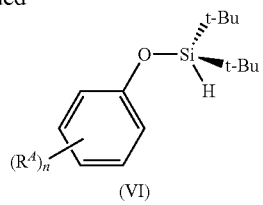

(VI)

It should be appreciated that an optionally substituted naphthol or hydroxylated 5- or 6-membered heteroaryll may stand in the place of the phenol, in which case the descriptions of this and the following Embodiments also include those Aspects where the structures are defined by the corresponding hydroxylated aromatic structures and are expected to be operable as described for the phenol derivative.

Embodiment 17. The method of Embodiment 16, further comprising converting the di-tert-butyl silyl phenyl ether to a di-tert-butyl hydroxy silyl phenyl ether. Again, other aromatic silyl ethers are considered within the scope of this Embodiment. In certain Aspects of this Embodiment, this step further comprises contacting the di-tert-butyl silyl phenyl ether described in Embodiment 16 with a base to form a di-tert-butyl hydroxy silyl phenyl ether. Without intending to limit the definition of the substitution of the substrates, in certain Aspects of this Embodiment, the di-tert-butyl silyl phenyl ether has a structure of Formula (VI), where n is 0, 1, 2, 3, 5, or 5, and $R^A$ are described as in Embodiment 16 and the di-tert-butyl hydroxy silyl phenyl ether of Formula (VII) is correspondingly substituted. In certain Aspects of this of this Embodiment, the base comprises a form of hydroxide, such as aqueous carbonate or basic (hydroxide-containing) DMF, as described for example in Huang, *J. Am. Chem. Soc.*, 2011, 133 (44), 17630-17633. Such a reaction may be represented schematically as:

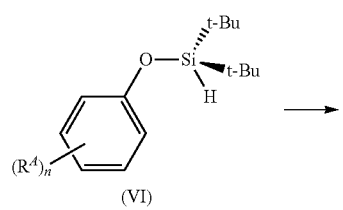

(VI)

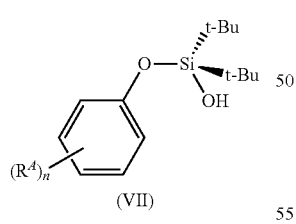

(VII)

and together Embodiments 16 and 17 may be represented by the schematic:

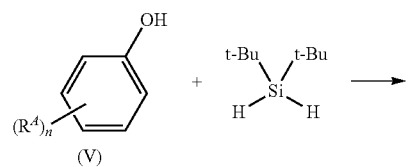

(V)

-continued

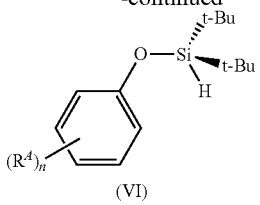

(VI)

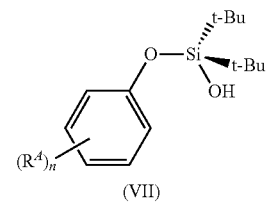

(VII)

Embodiment 18. The method of Embodiment 17, further comprising converting the di-tert-butyl hydroxy silyl phenyl ether to a catechol. Again, other aromatic hydroxy silyl ethers are considered within the scope of this Embodiment. In certain Aspects of this Embodiment, this step further comprises contacting the di-tert-butyl hydroxy silyl phenyl ether of Embodiment 17 with an acetoxylating reagent in the presence of a palladium catalyst to form to a catechol. Again, without intending to limit the definition of the substitution of the substrates, in certain Aspects of this Embodiment, the di-tert-butyl hydroxy silyl phenyl ether described in Embodiment 17 has a structure of Formula (VII), where n is 0, 1, 2, 3, 5, or 5, and $R^A$ are described as in Embodiment 16, and the corresponding catechol of Formula (IX) is correspondingly substituted. In certain Aspects of this of this Embodiment, the acetoxylating reagent is or comprises PhI(OAc)$_2$, as described in Huang, *J. Am. Chem. Soc.*, 2011, 133 (44), 17630-17633, which describes this transformation as a highly site-selective silanol-directed, Pd-catalyzed C—H oxygenation of phenols into catechols that operates via a silanol-directed acetoxylation, followed by a subsequent acid-catalyzed cyclization reaction into a cyclic silicon-protected catechol. The desilylation of the silacyle with TBAF to uncover the catechol product is described as routine. Exemplary reaction conditions in this reference includes reacting the 3-methyl derivative of the compound of Formula (VII) with Pd(OPiv)$_2$ (5 mol %), PhI(OAc)$_2$ (2 eq) in toluene at 100° C., for 6-12 hrs, followed by reaction with TBAF in THF. Such a reaction may be represented schematically as:

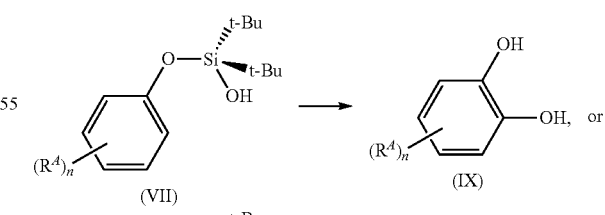

(VII) (IX)

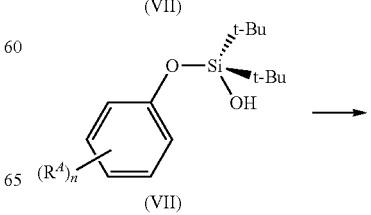

(VII)

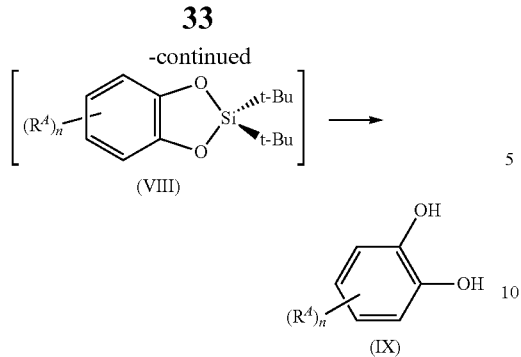

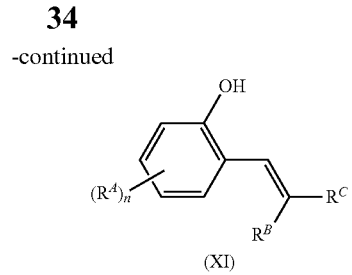

Embodiment 19. The method of Embodiment 17, further comprising converting the di-tert-butyl hydroxy silyl phenyl ether to an ortho-alkenylated phenol. Again, other aromatic hydroxy silyl ethers are considered within the scope of this Embodiment. In certain Aspects of this Embodiment, this step further comprises contacting the di-tert-butyl hydroxy silyl phenyl ether of Embodiment 17 with a terminal olefin in the presence of a palladium catalyst to form an ortho-alkenylated phenol. Again, without intending to limit the definition of the substitution of the substrates, in certain Aspects of this Embodiment the terminal olefin has a structure comprising Formula (X):

where $R^B$ is H or $C_{1-12}$ alkyl and $R^C$ is aldehyde, —C(O)—$C_{1-12}$ alkyl, —C(O)—$OC_{1-12}$ alkyl, —S(O)$_2$—$C_{1-12}$ alkyl, —S(O)$_2$—$C_{6-24}$ aryl, —S(O)$_2$—$OC_{1-12}$ alkyl, —S(O)$_2$—$OC_{6-24}$ aryl, optionally substituted (with one or more halo or $C_{1-6}$ alkyl) phenyl, or an optionally substituted 5- or 6-membered heterocyclic group. In certain independent Aspects of this Embodiment, the di-tert-butyl hydroxy silyl phenyl ether described in Embodiment 17 has a structure of Formula (VII), the ortho-alkenylated phenol has a structure of Formula (XI), where n is 0, 1, 2, 3, 5, or 5, and $R^A$ are described as in Embodiment 16, and the corresponding ortho-alkenylated phenol is correspondingly substituted. C. Huang, et al., *J. Am. Chem. Soc.*, 2011, 133 (32), pp 12406-12409 describes this transformation as silanol-directed, Pd(II)-catalyzed ortho-C—H alkenylation of phenols. Exemplary reaction conditions in this reference includes reacting the 3,4-dimethyl derivative of the compound of Formula (VII) with a variety of functionalized terminal olefins (2-4 equiv) in the presence of Pd(OAC)$_2$ (10 mol %), (+)menthyl(O$_2$C)-Leu-OH (20 mol %)), Li$_2$CO$_3$ (1 equiv), and AgOAc (4 equiv), in C$_6$F$_6$ at 100° C., followed by routine desilylation using TBAF/THF. Such a reaction may be represented schematically as:

Embodiment 20. The method of Embodiment 17, further comprising converting the di-tert-butyl hydroxy silyl phenyl ether to an ortho-carboxylic acid phenol. Again, other aromatic analogs are considered within the scope of this Embodiment. In certain Aspects of this Embodiment, this step further comprises contacting the di-tert-butyl hydroxy silyl phenyl ether of Embodiment 17 with carbon monoxide (CO) in the presence of a palladium catalyst to form an ortho-carboxylic acid phenol. Without intending to limit the definition of the substitution of the substrates, in certain Aspects of this Embodiment, the di-tert-butyl hydroxy silyl phenyl ether described in Embodiment 17 has a structure of Formula (VII), where n is 0, 1, 2, 3, 5, or 5, and RA are described as in Embodiment 16, and the corresponding ortho-carboxylic acid phenol of Formula (XIII) is correspondingly substituted. This transformation is described in Y. Wang, et al., *Angew Chem Int Ed Engl.* 2015 Feb. 9; 54(7): 2255-2259. Exemplary reaction conditions in this reference includes reacting the 3-tert-butyl derivative of the compound of Formula (VII) with CO in the presence of Pd(OAC)$_2$ (10 mol %), Boc-Leu-OH (20 mol %)), AgOAc (3 equiv), and CF$_3$CH$_2$OH (3 equiv) in dichloroethane at 95° C. for 18 hours, to form the cyclic derivative corresponding to Formula (XII), followed by routine desilylation using TBAF/THF to form the salicyclic derivative (Formula (XIII)). Such a reaction may be represented schematically as:

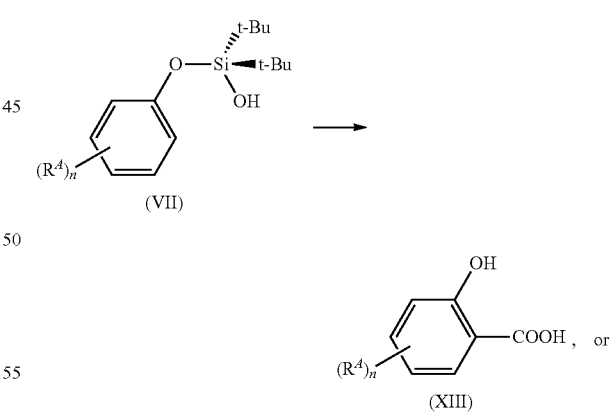

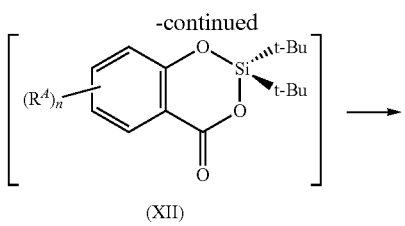

(XII)

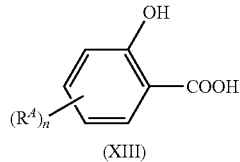

(XIII)

Embodiment 21. The method of any one of Embodiments 1 to 15, wherein the at least one hydrosilane is $(R^J)(R^K)Si(H)_2$, where $R^J$ comprises an optionally substituted phenyl, optionally substituted naphthyl, or optionally substituted 5- or 6-membered heteroaryl moiety and where $R^K$ is a $C_{1-3}$ alkyl.

Embodiment 22. The method of Embodiment 21, wherein $R^K$ is methyl and the organic substrate having at least one organic alcohol moiety is

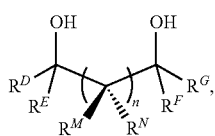

(IV)

the product of the reaction comprising a cyclic dioxasilolane. In certain Aspects of this Embodiment, the product cyclic dioxasilolane has a structure of Formula (XV);

wherein n is from 0 to 6; and $R^D$, $R^E$, $R^F$, and $R^G$ are defined as above in Embodiment 11 as independently H, $C_{1-6}$ alkyl, optionally substituted phenyl, optionally substituted benzyl, optionally substituted 5- or 6-ring membered heteroaryl, wherein the optional substituents are $C_{1-3}$ alkyl, $C_{1-3}$ alkoxy, or halo. Again, other substituted aromatic analogs are considered within the scope of this Embodiment. In some Aspects, the reaction may be represented schematically as:

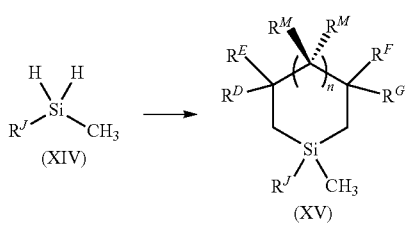

Embodiment 23. The method of Embodiment 21 or 22, wherein $R^J$ comprises an optionally substituted phenyl and the organic substrate having at least one organic alcohol moiety is 3-phenyl-butane-1,3-diol, 2,2-dimethyl-propane-1,3-diol, catechol, or pinacol. Without intending to necessarily limit the substituent pattern on the optionally substituted phenyl, in some Aspects of this Embodiment, the structures of Formula (XIV) may be characterized as having the structure of Formula (XIV-A) and the product of the method having a structure of any one of Formulae (XV-A), (XV-A1), (XV-A2), or (XV-A3). In some Aspects of this Embodiment, $(R^A)_n$ may be defined as described elsewhere herein (for example, in Embodiment 11).

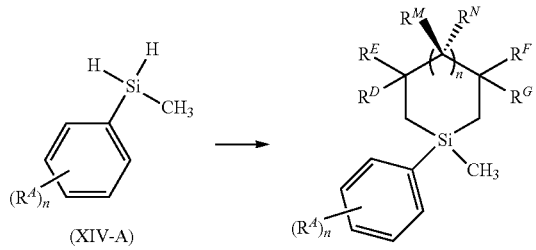

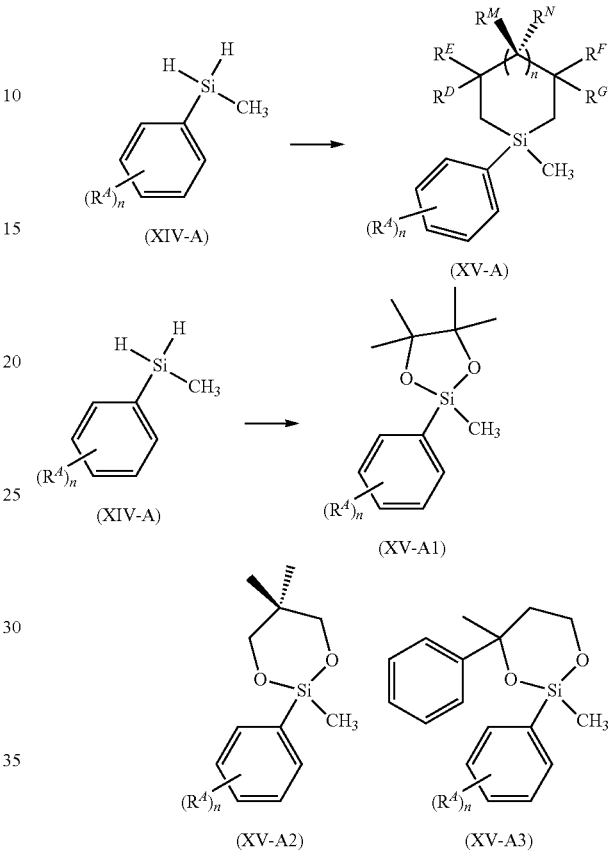

Embodiment 24. The method of any one of Embodiments 21 to 23, further comprising reacting the compound of Formula (XV) with an aromatic bromide or iodide in the presence of a palladium catalyst under conditions sufficient to couple the aromatic $R^J$ moiety to the aromatic bromide or iodide to form a biaromatic product. Exemplary conditions are described elsewhere herein.

Embodiment 25. The method of any one of Embodiments 21 to 23, further comprising reacting the compound of Formula (XV) with $C_{1-6}$ acrylate ester in the presence of a rhodium catalyst under conditions sufficient to couple the aromatic $R^J$ moiety with the $C_{1-6}$ acrylate ester to form a beta-aromatic substituted $C_{1-6}$ propionate ester product. Exemplary conditions are described elsewhere herein.

Embodiment 26. The method of any one of claims 21 to 23, further comprising reacting the compound of Formula (XV) with an optionally substituted benzimidazole in the presence of a copper catalyst under conditions sufficient to aminate the benzimidazole with the aromatic $R^J$ moiety. Exemplary conditions are described elsewhere herein.

Embodiment 27. A composition comprising or consisting essentially of (a) at least one hydrosilane; (b) sodium and/or potassium hydroxide; (c) an organic substrate having at least one organic alcohol moiety; and optionally (d) a silyl ether resulting from the dehydrogenative coupling of the at least one hydrosilane and the at least one alcohol moiety. As described in Embodiment 1, certain independent Aspects of this Embodiment 27 provide that the composition is substantially free of absence of transition metal catalysts; substantially free of "superbases," such as alkoxides, hydrides, alkyl lithium reagents, or any chemical known to enhance the activity of the NaOH or KOH (e.g., crown ethers), and/or substantially free of added fluoride ion. In still other Aspects of this Embodiment, the compositions comprise aprotic polar solvents such as acetonitrile, dimethylacetamide, dimethyl formamide, dimethylsulfoxide, polyglycols (including, for example, dimethoxyethane, DME), optionally substituted dioxanes, dialkyl ethers (e.g., diethyl, dimethyl ether), hexamethylphosphoramide (HMPA), optionally substituted THF and furans, and N-methylpyrrolidone (NMP). The presence of NaOH, KOH, or a combination of NaOH and KOH represent independent Aspects of this Embodiment.

Embodiment 28. The composition of Embodiment 27, wherein the hydrosilane has a structure of Formula (I) or a hydrodisilane structure of Formula (II):

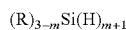  (I)

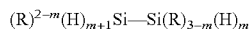  (II)

where: m is independently 0, 1, or 2; and each R is independently optionally substituted $C_{1-24}$ alkyl or heteroalkyl, optionally substituted $C_{2-24}$ alkenyl or heteroalkenyl, optionally substituted $C_{2-24}$ alkynyl or heteroalkynyl, optionally substituted 6 to 18 ring membered aryl or 5 to 18 ring membered heteroaryl, optionally substituted 6 to 18 ring-membered alkaryl or 5 to 18 ring-membered heteroalkaryl, optionally substituted 6 to 18 ring-membered aralkyl or 5 to 18 ring-membered heteroaralkyl, optionally substituted —O—$C_{1-24}$ alkyl or heteroalkyl, optionally substituted 6 to 18 ring-membered aryloxy or 5 to 18 ring-membered heteroaryloxy, optionally substituted 6 to 18 ring-membered alkaryloxy or 5 to 18 ring-membered heteroalkaryloxy, or optionally substituted 6 to 18 ring-membered aralkoxy or 5 to 18 ring-membered heteroaralkoxy, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, 5 to 12 ring-membered arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon. In individual Aspects of this Embodiment, m is 0, m is 1, m is 2. In certain independent Aspects of this embodiment, the hydrosilane is a compound of Formula (I); in other Aspects, the hydrosilane is a compound of Formula (II). In other independent Aspects of this Embodiment, the hydrosilane is a hydrosilane of Formula (I), where m is 1 or where m is 2. In still other Aspects, the hydrosilane is or comprises EtMe$_2$SiH, Et$_3$SiH, (n-Bu)$_3$SiH, (i-Pr)$_3$SiH, Et$_2$SiH$_2$, Ph$_2$MeSiH, (t-Bu)Me$_2$SiH, (t-Bu)$_2$SiH$_2$, PhMeSiH$_2$, PhMe$_2$SiH, BnMe$_2$SiH, (EtO)$_3$SiH, Me$_2$(pyridinyl)SiH, (i-Pr)$_2$(pyridinyl)SiH, or Me$_3$Si—SiMe$_2$H Embodiment 29. The composition of Embodiments 27 or 28, wherein the organic substrate having at least one organic alcohol moiety has a formula of R$^1$—OH or HO—R$^2$—OH, as describe elsewhere herein. In some Aspects of this Embodiment, the organic substrate having at least one organic alcohol moiety is or comprises an optionally substituted catechol compound or moiety or has a Formula (IV), or its various permutations as described above:

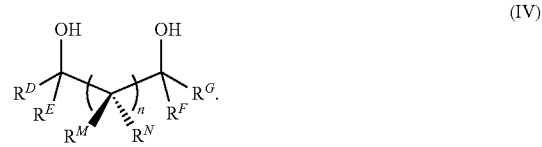

In independent Aspects of this Embodiment, the organic substrate may be polymeric, comprise an aliphatic alcohol moiety, comprise an aromatic or α-methyl aromatic alcohol moiety, or comprises an optionally substituted benzylic alcohol moiety.

Embodiment 30. The composition of any one of Embodiments 27 to 29, wherein the hydrosilane is (tert-butyl)$_2$Si(H)$_2$, at least one organic alcohol moiety is an optionally substituted phenol, naphthol, or hydroxylated 5- or 6-membered heteroaryl, and the reaction product comprises the corresponding di-tert-butyl silyl ether.

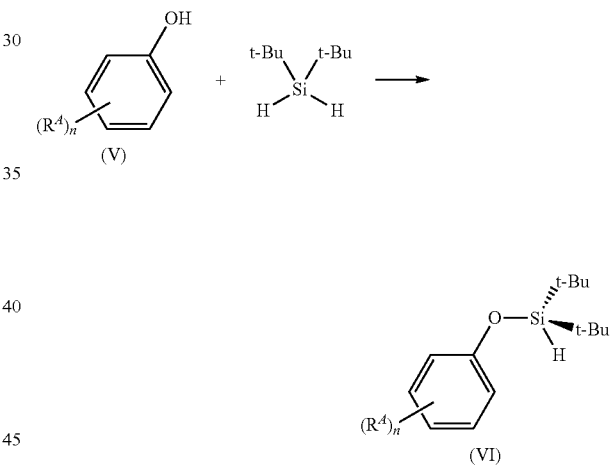

It should be appreciated that an optionally substituted naphthol or hydroxylated 1 may stand in the place of the phenol, in which case the descriptions of this and the following Embodiments also include those Aspects where the structures are defined by the corresponding hydroxylated aromatic structures and are expected to be operable as described for the phenol derivative.

Embodiment 31. The composition of any one of Embodiments 27 to 29, wherein the at least one hydrosilane is (R$^J$)(R$^K$)Si(H)$_2$, where R$^J$ comprises an optionally substituted phenyl, optionally substituted naphthyl, or optionally substituted 5- or 6-membered heteroaryl as described elsewhere herein and where R$^K$ is a C$_{1-3}$ alkyl. Again, other substituted aromatic analogs are considered within the scope of this Embodiment.

Embodiment 32. The composition of Embodiment 31, wherein R$^K$ is methyl and the organic substrate having at least one organic alcohol moiety is or comprises a compound of Formula (IV) or any of the permutations of this structure described elsewhere herein:

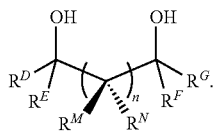
(IV)

In certain Aspects of this Embodiment, the reaction product is present and comprises as cyclic dioxasilolane. In certain Aspects of this Embodiment, the product cyclic dioxasilolane has a structure of Formula (XV), or any of the permutations of this structure described elsewhere herein, including but not limited to structures of Formulae (XV-A), (XV-A1), (XV-A2), or (XV-A3).

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Example 1. Materials and Methods

Unless otherwise stated, reactions were performed in oven-dried brand-new Fisherbrand scintillation vials flushed with argon or in flame-dried Schlenk flasks under argon connected on a Schlenk line using dry, degassed solvents and brand-new stirring bars. Solvents were dried by passage through an activated alumina column under argon. Reaction progress was monitored by thin-layer chromatography (TLC) or GC-FID analyses. TLC was performed using E. Merck silica gel 60 F254 precoated glass plates (0.25 mm) and visualized by UV fluorescence quenching, phosphomolybdic acid, or KMnO$_4$ staining. Silicycle SiliaFlash P60 Academic Silica gel (particle size 40-63 nm) was used for flash chromatography. $^1$H NMR spectra were recorded on a Varian Inova 500 MHz spectrometer in CDCl$_3$, THF-d8, or C$_6$D$_6$ and are reported relative to residual solvent peak at δ 7.26 ppm, δ 3.58 ppm, or δ 7.16 ppm respectively. $^{13}$C NMR spectra were recorded on a Varian Inova 500 MHz spectrometer (126 MHz) in CDCl$_3$, THF-d8, or C$_6$D$_6$ and are reported relative to residual solvent peak at δ 77.16 ppm, δ 67.21 ppm, or δ 67.21 ppm respectively. Data for $^1$H NMR are reported as follows: chemical shift (δ ppm) (multiplicity, coupling constant (Hz), integration). Multiplicities are reported as follows: s=singlet, d=doublet, t=triplet, q=quartet, p=pentet, sept=septet, m=multiplet, br s=broad singlet, br d=broad doublet, app=apparent. Data for $^{13}$C NMR are reported in terms of chemical shifts (δ ppm). IR spectra were obtained on a Perkin Elmer Spectrum BXII spectrometer using thin films deposited on NaCl plates and reported in frequency of absorption (cm$^{-1}$). GC-FID analyses were obtained on an Agilent 6890N gas chromatograph equipped with a HP-5 (5%-phenyl)-methylpolysiloxane capillary column (Agilent). GC-MS analyses were obtained on an Agilent 6850 gas chromatograph equipped with a HP-5 (5%-phenyl)-methylpolysiloxane capillary column (Agilent). High resolution mass spectra (HRMS) were acquired from the California Institute of Technology Mass Spectrometry Facility. ICP-MS analysis was conducted at the California Institute of Technology Mass Spectrometry Facility.

Silanes were purchased from Aldrich and distilled before use. NaOH was purchased from Aldrich (semiconductor grade, pellets, 99.99% trace metals basis) and was pulverized (mortar and pestle) and heated (150° C.) under vacuum prior to use. Powdered and vacuum-dried (as above) ACS grade ≥97% NaOH from Aldrich gives identical results. Alcohol and phenol substrates were purchased from Aldrich, TCI, or Acros.

Example 2. Screening Studies

Example 2.1. Reaction Optimization

Procedure for reaction condition optimization: In a nitrogen-filled glovebox, catalyst and alcohol 1a (0.1 mmol, 1 equiv) were added to a 2 dram scintillation vial equipped with a magnetic stirring bar. Next, hydrosilane and solvent (0.1 mL) were added. The vial was sealed and the mixture was stirred at the indicated temperature for the indicated time. The vial was then removed from the glovebox, diluted with diethyl ether (1 mL), and concentrated under reduced pressure. The yield was determined by $^1$H NMR or GC analysis of the crude mixture using an internal standard.

The initial studies showed that THF and DME proved to be suitable solvents. The addition of DMF to reaction mixtures enabled the silylation in challenging cases; curiously, several substrates failed to silylate without the addition of DMF. See characterization data (Part II) for a comprehensive view of all substrates that required addition of DMF. No product was observed in the absence of the hydroxide catalyst.

Example 2.2. Experimental and Analytics

Example 2.2.1. General Procedure for Cross-Dehydrogenative O—H Silylation and Characterization Data.

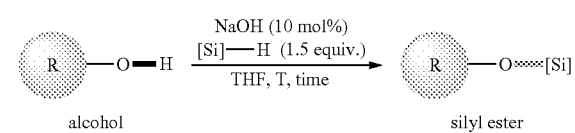

NaOH (0.05 mmol, 10 mol %) was added to a hot, oven-dried 2 dram scintillation vial equipped with a magnetic stirring bar, and the vial was purged with argon until cool. Alcohol (0.5 mmol, 1 equiv) was then added under a steady stream of argon, followed by solvent (0.5 mL) and silane (0.75 mmol, 1.5 equiv). The vial was then sealed and the mixture was stirred at the indicated temperature for the indicated time. After the reaction was complete, the reaction mixture was diluted with diethyl ether (2 mL), filtered through a short pad of silica gel, and concentrated under reduced pressure. Volatiles were removed under high vacuum and the resultant material was purified by silica gel flash chromatography if necessary to give the desired O—Si product.

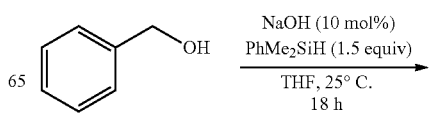

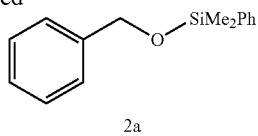

2a

Example 2.2.2. (Benzyloxy)dimethyl(phenyl)silane 2a: The general procedure was followed. The reaction was performed with NaOH (2.0 mg, 0.05 mmol, 10 mol %), benzyl alcohol (54 mg, 0.5 mmol, 1.0 equiv), PhMe$_2$SiH (102 mg, 115 µL, 0.75 mmol, 1.5 equiv), and 0.5 mL of tetrahydrofuran (THF) at 25° C. for 18 h. The desired product 2a (113.9 mg, 94% yield) was obtained as a colorless oil by silica gel flash chromatography (5% EtOAc in hexanes). R$_f$=0.53 (5% EtOAc in hexanes); $^1$H NMR (500 MHz, CDCl$_3$) δ 7.70-7.66 (m, 2H), 7.48-7.42 (m, 3H), 7.40-7.35 (m, 4H), 7.30 (dddd, J=6.7, 6.2, 3.1, 1.7 Hz, 1H), 4.77 (s, 2H), 0.49 (s, 6H). This compound has been previously characterized. See Mitsudome, T., et al., *Chemistry A European Journal*, 2013, 19 (43), 14398-14402.

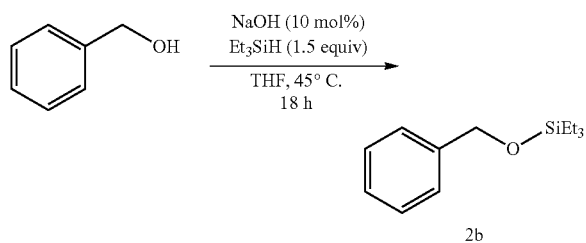

2b

Example 2.2.3. (Benzyloxy)triethylsilane 2b: The general procedure was followed. The reaction was performed with NaOH (2.0 mg, 0.05 mmol, 10 mol %), benzyl alcohol (54 mg, 0.5 mmol, 1.0 equiv), Et$_3$SiH (87 mg, 120 µL, 0.75 mmol, 1.5 equiv), and 0.5 mL of tetrahydrofuran (THF) at 45° C. for 18 h. The desired product 2b (101.2 mg, 91% yield) was obtained as a colorless oil by silica gel flash chromatography (5% EtOAc in hexanes). R$_f$=0.27 (5% EtOAc in hexanes); $^1$H NMR (500 MHz, CDCl$_3$) δ 7.36-7.31 (m, 4H), 7.27-7.23 (m, 1H), 4.75 (s, 2H), 1.00 (t, J=8.0 Hz, 9H), 0.67 (q, J=7.9 Hz, 5H). This compound has been previously characterized. See Abri, A., et al., *Journal of the Chinese Chemical Society*, 2012, 59 (11), 1449-1454.

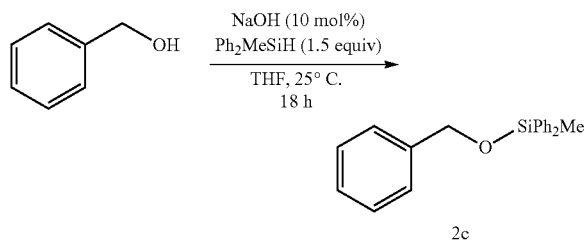

2c

Example 2.2.4. (Benzyloxy)(methyl)diphenylsilane 2c: The general procedure was followed. The reaction was performed with NaOH (2.0 mg, 0.05 mmol, 10 mol %), benzyl alcohol (54 mg, 0.5 mmol, 1.0 equiv), Ph$_2$MeSiH (149 mg, 150 µL, 0.75 mmol, 1.5 equiv), and 0.5 mL of tetrahydrofuran (THF) at 25° C. for 18 h. The desired product 2c (129.4 mg, 85% yield) was obtained as a colorless oil by silica gel flash chromatography (5% EtOAc in hexanes). R$_f$=0.50 (5% EtOAc in hexanes); $^1$H NMR (500 MHz, CDCl$_3$) δ 7.72 (p, J=7.7, 7.0 Hz, 3H), 7.69-7.58 (m, 2H), 7.54-7.37 (m, 10H), 4.90 (dt, J=13.7, 3.0 Hz, 2H), 0.77 (dt, J=14.1, 2.9 Hz, 3H). This compound has been previously characterized. See Igarashi, M., et al. *Chemistry Letters*, 2014, 43 (4), 429-431

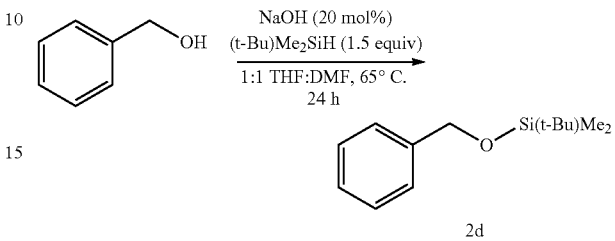

2d

Example 2.2.5. (Benzyloxy)(tert-butyl)dimethylsilane 2d: The general procedure was followed. The reaction was performed with NaOH (4.0 mg, 0.1 mmol, 20 mol %), benzyl alcohol (54 mg, 0.5 mmol, 1.0 equiv), (t-Bu)Me$_2$SiH (87 mg, 124 µL, 1.5 mmol, 3.0 equiv), 0.25 mL dimethylformamide (DMF) and 0.25 mL of tetrahydrofuran (THF) at 65° C. for 24 h. The desired product 2d (66.2 mg, 60% yield) was obtained as a colorless oil by silica gel flash chromatography (5% EtOAc in hexanes). R$_f$=0.42 (5% EtOAc in hexanes); $^1$H NMR (500 MHz, CDCl$_3$) δ 7.35 (d, J=4.6 Hz, 4H), 7.28-7.24 (m, 1H), 4.78 (d, J=0.6 Hz, 2H), 0.98 (s, 9H), 0.14 (s, 6H). This compound has been previously characterized. See Yamamoto, K., et al., *Bulletin of the Chemical Society of Japan*, 1989, 62 (6), 2111-2113.

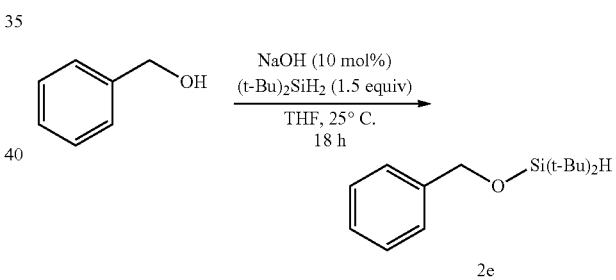

2e

Example 2.2.6. (Benzyloxy)di-tert-butylsilane 2e: The general procedure was followed. The reaction was performed with NaOH (2.0 mg, 0.05 mmol, 10 mol %), benzyl alcohol (54 mg, 0.5 mmol, 1.0 equiv), (t-Bu)$_2$SiH$_2$ (108 mg, 148 µL, 0.75 mmol, 1.5 equiv), and 0.5 mL of tetrahydrofuran (THF) at 25° C. for 18 h. The desired product 2e (120.2 mg, 96% yield) was obtained as a colorless oil after removal of volatiles under high vacuum (45 mtorr) for 2 hours. $^1$H NMR (500 MHz, CDCl$_3$) δ 7.39-7.34 (m, 4H), 7.29-7.25 (m, 1H), 4.88 (d, J=0.7 Hz, 2H), 4.12 (s, 1H), 1.05 (s, 18H). This compound has been previously characterized. See Curran, D. P. et al., *Journal of the Chemical Society, Perkin Transactions 1: Organic and Bio-Organic Chemistry (1972-1999)*, 1995, 24, 3049-3060

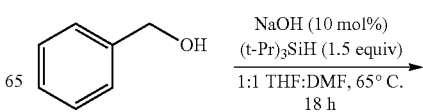

43

-continued

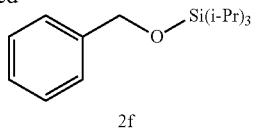

2f

Example 2.2.7. (Benzyloxy)triisopropylsilane 2f: The general procedure was followed. The reaction was performed with NaOH (2.0 mg, 0.05 mmol, 10 mol %), benzyl alcohol (54 mg, 0.5 mmol, 1.0 equiv), (i-Pr)$_3$SiH (119 mg, 154 µL, 0.75 mmol, 1.5 equiv), 0.25 mL dimethylformamide (DMF), and 0.25 mL of tetrahydrofuran (THF) at 65° C. for 18 h. The desired product 2f (112.4 mg, 85% yield) was obtained as a colorless oil by silica gel flash chromatography (5% EtOAc in hexanes). R$_f$=0.52 (5% EtOAc in hexanes); $^1$H NMR (500 MHz, CDCl$_3$) δ 1H NMR (500 MHz, Chloroform-d) d 7.40-7.32 (m, 4H), 7.27-7.23 (m, 1H), 4.87 (d, J=1.5 Hz, 2H), 1.26-1.17 (m, 3H), 1.15-1.11 (m, 18H). This compound has been previously characterized. See Khalafi-Nezhad, A., et al., *Tetrahedron*, 2000, 56 (38), 7503-7506.

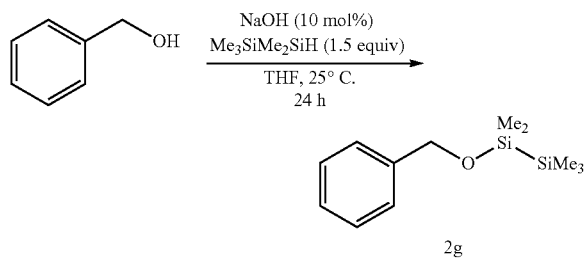

2g

Example 2.2.8. 1-(Benzyloxy)-1,1,2,2,2-pentamethyldisilane 2g: The general procedure was followed. The reaction was performed with NaOH (2.0 mg, 0.05 mmol, 10 mol %), benzyl alcohol (54 mg, 0.5 mmol, 1.0 equiv), Me$_5$Si$_2$H (99 mg, 137 µL, 0.75 mmol, 1.5 equiv), and 0.5 mL of tetrahydrofuran (THF) at 25° C. for 24 h. Concentration of the reaction mixture and purification of the resulting residue via Kugelrohr distillation (120 mTorr, 60° C.) gave 79.9 mg (67% yield) of 2g as a colorless oil. $^1$H NMR (500 MHz, THF-d8) δ 7.31-7.24 (m, 4H), 7.21-7.15 (m, 1H), 4.68 (q, J=0.7 Hz, 2H), 0.23 (s, 6H), 0.10 (s, 9H); $^{13}$C NMR (126 MHz, THF-d8) δ 142.61, 128.96, 127.71, 127.01, 66.02, −0.52, −1.79. IR (Neat Film NaCl) 3363, 3088, 3065, 3030, 2952, 2893, 1595, 1495, 1453, 1376, 1259, 1246, 1207, 1091, 1067, 1026, 835, 803, 766, 729, 695, 655, 617 cm$^{-1}$; HRMS (EI+) calc'd for C$_{12}$H$_{23}$OSi$_2$ [M+H]: 239.1288, found 239.1295.

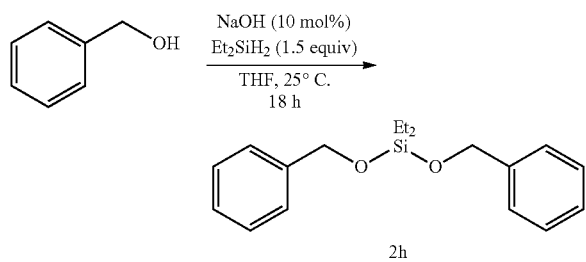

2h

44

Example 2.2.9. Bis(benzyloxy)diethylsilane 2h: The general procedure was followed. The reaction was performed with NaOH (2.0 mg, 0.05 mmol, 10 mol %), benzyl alcohol (108 mg, 1.0 mmol, 1.0 equiv), Et$_2$SiH$_2$ (49 mg, 71 µL, 0.55 mmol, 0.55 equiv), and 1.0 mL of tetrahydrofuran (THF) at 25° C. for 18 h. The desired product 2h (120.8 mg, 80% yield) was obtained as a colorless oil by silica gel flash chromatography (5% EtOAc in hexanes). R$_f$=0.43 (5% EtOAc in hexanes); $^1$H NMR (500 MHz, CDCl$_3$) δ 7.35 (d, J=4.4 Hz, 8H), 7.31-7.26 (m, 2H), 4.82 (s, 4H), 1.05 (t, J=7.9 Hz, 6H), 0.76 (q, J=8.0 Hz, 4H). This compound has been previously characterized. See Chatterjee, B., et al., *Chemical Communications*, 2014, 50 (7), 888-890

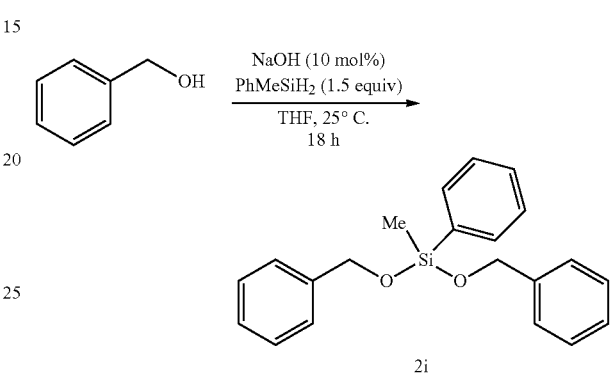

2i

Example 2.2.10. Bis(benzyloxy)(methyl)(phenyl)silane 2i: The general procedure was followed. The reaction was performed with NaOH (2.0 mg, 0.05 mmol, 10 mol %), benzyl alcohol (108 mg, 1.0 mmol, 1.0 equiv), MePhSiH$_2$ (67 mg, 76 µL, 0.55 mmol, 0.55 equiv), and 1.0 mL of tetrahydrofuran (THF) at 25° C. for 18 h. The desired product 2i (158.8 mg, 95% yield) was obtained as a colorless oil by silica gel flash chromatography (5% EtOAc in hexanes). R$_f$=0.44 (5% EtOAc in hexanes); $^1$H NMR (500 MHz, CDCl$_3$) δ 1H NMR (500 MHz, Chloroform-d) d 7.76 (dd, J=7.9, 1.5 Hz, 2H), 7.49-7.43 (m, 3H), 7.39-7.37 (m, 8H), 7.33-7.28 (m, 2H), 4.91-4.82 (m, 4H), 0.50 (s, 3H). This compound has been previously characterized. See Kita, Y., et al., *Tetrahedron Letters*, 1983, 24 (12), 1273-1276.

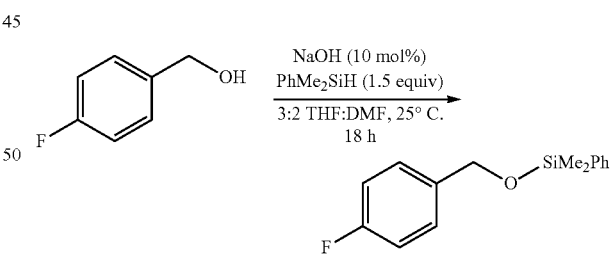

4a

Example 2.2.11. ((4-Fluorobenzyl)oxy)dimethyl(phenyl)silane 4a: The general procedure was followed. The reaction was performed with NaOH (2.0 mg, 0.05 mmol, 10 mol %), 4-fluorobenzyl alcohol (63 mg, 0.5 mmol, 1.0 equiv), PhMe$_2$SiH (102 mg, 115 µL, 0.75 mmol, 1.5 equiv), 0.2 mL dimethylformamide (DMF) and 0.3 mL of tetrahydrofuran (THF) at 25° C. for 18 h. The desired product 4a (146.0 mg, 79% yield) was obtained as a colorless oil by silica gel flash chromatography (5% EtOAc in hexanes). R$_f$=0.48 (5% EtOAc in hexanes); $^1$H NMR (500 MHz, CDCl$_3$) δ 7.65-7.59 (m, 2H), 7.46-7.37 (m, 3H), 7.31-7.25 (m, 2H), 7.06-

6.97 (m, 2H), 4.67 (q, J=0.8 Hz, 2H), 0.45 (s, 6H). $^{13}$C NMR (126 MHz, CDCl$_3$) δ 162.14 (d, J=244.4 Hz), 137.50, 136.53 (d, J=2.9 Hz), 133.64, 129.90, 128.37 (d, J=8.3 Hz), 128.06, 115.19 (d, J=21.1 Hz), 64.48, −1.60. IR (Neat Film NaCl) 3440, 3070, 3050, 3022, 2958, 2866, 1605, 1509, 1463, 1427, 1417, 1375, 1294, 1253, 1221, 1155, 1117, 1082, 1014, 826, 789, 741, 700, 645 cm$^{-1}$; HRMS (EI+) calc'd for C$_{15}$H$_{16}$OSiF [(M+H)−H$_2$]: 259.0955, found 259.0951.

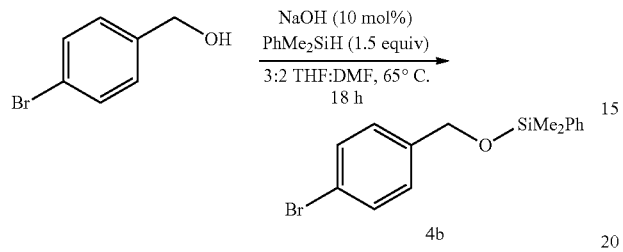

Example 2.2.11. ((4-Bromobenzyl)oxy)dimethyl(phenyl) silane 4b: The general procedure was followed. The reaction was performed with NaOH (2.0 mg, 0.05 mmol, 10 mol %), 4-bromobenzyl alcohol (94 mg, 0.5 mmol, 1.0 equiv), PhMe$_2$SiH (102 mg, 115 μL, 0.75 mmol, 1.5 equiv), 0.2 mL dimethylformamide (DMF) and 0.3 mL of tetrahydrofuran (THF) at 65° C. for 24 h. The desired product 4b (146.2 mg, 91% yield) was obtained as a colorless oil by silica gel flash chromatography (5% EtOAc in hexanes). R$_f$=0.48 (5% EtOAc in hexanes); $^1$H NMR (500 MHz, CDCl$_3$) δ 7.61 (dd, J=7.7, 1.8 Hz, 2H), 7.47-7.34 (m, 5H), 7.19 (dt, J=8.7, 0.7 Hz, 2H), 4.66 (d, J=0.8 Hz, 2H), 0.44 (s, 6H). This compound has been previously characterized. See Kennedy-Smith, J. J., et al., *J. Amer. Chem. Soc.*, 2003, 125 (14), 4056-4057.

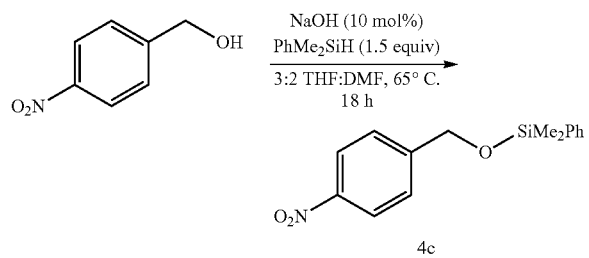

Example 2.2.12. Dimethyl((4-nitrobenzyl)oxy)(phenyl) silane 4c: The general procedure was followed. The reaction was performed with NaOH (2.0 mg, 0.05 mmol, 10 mol %), 4-nitrobenzyl alcohol (77 mg, 0.5 mmol, 1.0 equiv), PhMe$_2$SiH (102 mg, 115 μL, 0.75 mmol, 1.5 equiv), 0.2 mL dimethylformamide (DMF) and 0.3 mL of tetrahydrofuran (THF) at 65° C. for 18 h. The desired product 4c (102.2 mg, 71% yield) was obtained as a colorless oil by silica gel flash chromatography (5% EtOAc in hexanes). R$_f$=038 (5% EtOAc in hexanes); $^1$H NMR (500 MHz, CDCl$_3$) δ 8.21-8.15 (m, 2H), 7.60 (dd, J=7.8, 1.7 Hz, 2H), 7.47 (dt, J=8.8, 0.8 Hz, 2H), 7.44-7.38 (m, 3H), 4.79 (t, J=0.8 Hz, 2H), 0.47 (s, 6H); $^{13}$C NMR (126 MHz, CDCl$_3$) δ 148.51, 147.18, 136.92, 133.59, 130.13, 128.18, 126.77, 123.68, 64.03, −1.73. IR (Neat Film NaCl) 3423, 2958, 1641, 1608, 1519, 1527, 1253, 1117, 1094, 856, 830, 786, 735, 700 cm$^{-1}$; HRMS (EI+) calc'd for C$_{15}$H$_{18}$SiO$_3$N [M+H]: 288.1056, found 288.1058.

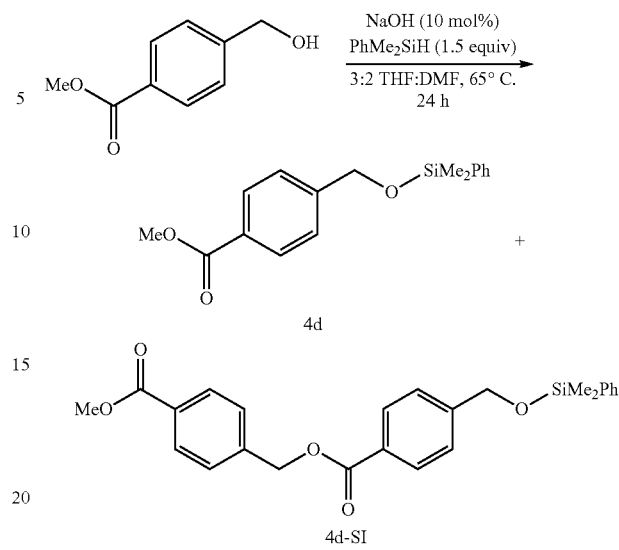

Example 2.2.11. Methyl 4-(((dimethyl(phenyl)silyl)oxy) methyl)benzoate 4d: The general procedure was followed. The reaction was performed with NaOH (2.0 mg, 0.05 mmol, 10 mol %), methyl 4-(hydroxymethyl)benzoate (83 mg, 0.5 mmol, 1.0 equiv), PhMe$_2$SiH (102 mg, 115 μL, 0.75 mmol, 1.5 equiv), 0.2 mL dimethylformamide (DMF) and 0.3 mL of tetrahydrofuran (THF) at 65° C. for 24 h. The desired product 4d (100.6 mg, 67% yield) was obtained as a colorless oil by silica gel flash chromatography (gradient 15% EtOAc to 30% EtOAc in hexanes). R$_f$=0.62 (15% EtOAc in hexanes); $^1$H NMR (500 MHz, CDCl$_3$) δ 8.01 (d, J=8.3 Hz, 2H), 7.63-7.60 (m, 2H), 7.45-7.36 (m, 5H), 4.76 (d, J=0.8 Hz, 2H), 3.92 (s, 3H), 0.46 (s, 6H). This compound has been previously characterized. See Fernandez, A. C., et al., *Chem. Comm.*, 2005, 2, 213-214

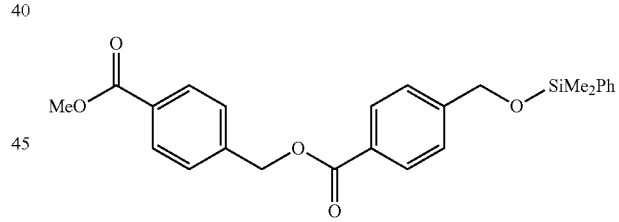

Example 2.2.12. 4-(Methoxycarbonyl)benzyl 4-(((dimethyl(phenyl)silyl)oxy)methyl)benzoate 4d-SI: Also isolated from the column was 4d-SI (36.9 mg, 34% silylation yield/ 17% yield based on methyl 4-(hydroxymethyl)benzoate stoichiometry) as a colorless solid. R$_f$=0.43 (15% EtOAc in hexanes); $^1$H NMR (500 MHz, CDCl$_3$) δ 8.08-8.03 (m, 4H), 7.62-7.58 (m, 2H), 7.51 (dt, J=8.6, 0.7 Hz, 2H), 7.43-7.37 (m, 5H), 5.42 (s, 2H), 4.76 (d, J=0.8 Hz, 2H), 3.93 (s, 3H), 0.44 (s, 6H); $^{13}$C NMR (126 MHz, CDCl$_3$) δ 166.88, 166.31, 146.62, 141.30, 137.26, 133.61, 130.02, 129.97, 129.90, 128.63, 128.09, 127.72, 126.27, 65.94, 64.53, 52.32, −1.64.

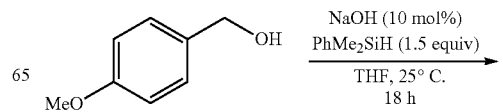

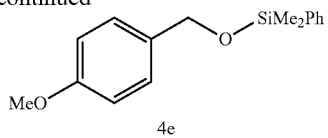

Example 2.2.13. ((4-Methoxybenzyl)oxy)dimethyl(phenyl)silane 4e: The general procedure was followed. The reaction was performed with NaOH (2.0 mg, 0.05 mmol, 10 mol %), 4-methoxybenzyl alcohol (69 mg, 0.5 mmol, 1.0 equiv), PhMe$_2$SiH (102 mg, 115 µL, 0.75 mmol, 1.5 equiv), and 0.5 mL of tetrahydrofuran (THF) at 25° C. for 18 h. The desired product 4e (117.9 mg, 87% yield) was obtained as a colorless oil by silica gel flash chromatography (5% EtOAc in hexanes). R$_f$=0.29 (5% EtOAc in hexanes); $^1$H NMR (500 MHz, CDCl$_3$) δ 7.62 (dd, J=7.5, 2.0 Hz, 2H), 7.44-7.37 (m, 3H), 7.25-7.20 (m, 2H), 6.87 (d, J=8.6 Hz, 2H), 4.64 (d, J=0.6 Hz, 2H), 3.81 (s, 3H), 0.42 (s, 6H). This compound has been previously characterized. See Bideau, F. L., et al., *Chem. Comm.* (*Cambridge, United Kingdom*), 2001, 15, 1408-1409

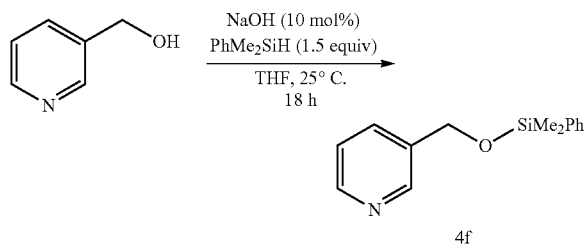

Example 2.2.14. 3-(((Dimethyl(phenyl)silyl)oxy)methyl)pyridinesilane 4f: The general procedure was followed. The reaction was performed with NaOH (2.0 mg, 0.05 mmol, 10 mol %), pyridin-3-ylmethanol (55 mg, 0.5 mmol, 1.0 equiv), PhMe$_2$SiH (102 mg, 115 µL, 0.75 mmol, 1.5 equiv), and 0.5 mL of tetrahydrofuran (THF) at 25° C. for 18 h. The desired product 4f (118.1 mg, 97% yield) was obtained as a colorless oil by removal of volatiles at 80° C. at 60 mTorr. $^1$H NMR (500 MHz, CDCl$_3$) δ 8.52 (dt, J=2.3, 0.8 Hz, 1H), 8.49 (dd, J=4.8, 1.6 Hz, 1H), 7.65 (dtd, J=7.8, 1.7, 0.9 Hz, 1H), 7.61-7.57 (m, 2H), 7.43-7.37 (m, 3H), 7.26 (ddd, J=7.9, 4.8, 0.9 Hz, 1H), 4.70 (dt, J=0.6 Hz, 2H), 0.44 (s, 6H). This compound has been previously characterized. See Goldberg, Y., et al., *Synthetic Communications*, 1990, 20 (16), 2439-2446.

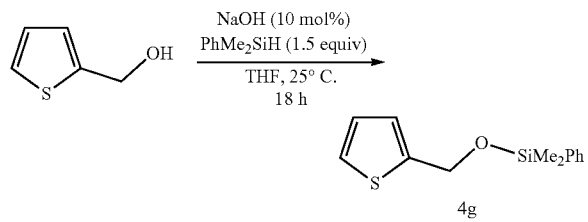

Example 2.2.15. Dimethyl(phenyl)(thiophen-2-ylmethoxy)silane 4g: The general procedure was followed. The reaction was performed with NaOH (2.0 mg, 0.05 mmol, 10 mol %), thiophen-2-ylmethanol (57 mg, 0.5 mmol, 1.0 equiv), PhMe$_2$SiH (102 mg, 115 µL, 0.75 mmol, 1.5 equiv), and 0.5 mL of tetrahydrofuran (THF) at 25° C. for 18 h. The desired product 4g (119.2 mg, 96% yield) was obtained as a colorless oil by removal of volatiles at 80° C. at 60 mTorr. $^1$H NMR (500 MHz, CDCl$_3$) δ 7.68-7.63 (m, 2H), 7.47-7.43 (m, 3H), 7.26 (dd, J=5.0, 1.3 Hz, 1H), 6.97 (dd, J=5.0, 3.4 Hz, 1H), 6.94-6.91 (m, 1H), 4.87 (d, J=0.8 Hz, 2H), 0.47 (s, 6H). This compound has been previously characterized. See Goldberg, Y., et al., *Journal of Organometallic Chemistry*, 1991, 410 (2), 127-133.

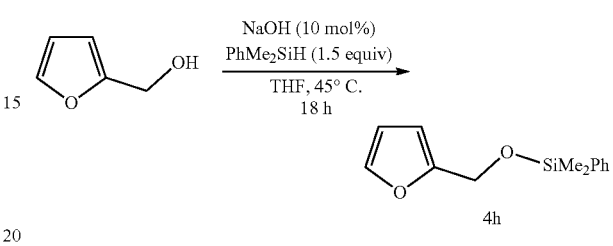

Example 2.2.16. (Furan-2-ylmethoxy)dimethyl(phenyl)silane 4h: The general procedure was followed. The reaction was performed with NaOH (2.0 mg, 0.05 mmol, 10 mol %), furfuryl alcohol (49 mg, 0.5 mmol, 1.0 equiv), PhMe$_2$SiH (102 mg, 115 µL, 0.75 mmol, 1.5 equiv), and 0.5 mL of tetrahydrofuran (THF) at 45° C. for 18 h. The desired product 4h (101.1 mg, 87% yield) was obtained as a colorless oil by removal of volatiles at 80° C. at 60 mTorr. $^1$H NMR (500 MHz, CDCl$_3$) δ 7.62 (ddd, J=7.5, 2.4, 1.3 Hz, 2H), 7.46-7.33 (m, 4H), 6.32 (dt, J=3.4, 1.8 Hz, 1H), 6.21 (t, J=2.5 Hz, 1H), 4.62 (d, J=2.0 Hz, 2H), 0.39-0.35 (m, 6H). This compound has been previously characterized. See Goldberg, Y., et al., *Journal of Organometallic Chemistry*, 1991, 410 (2), 127-133.

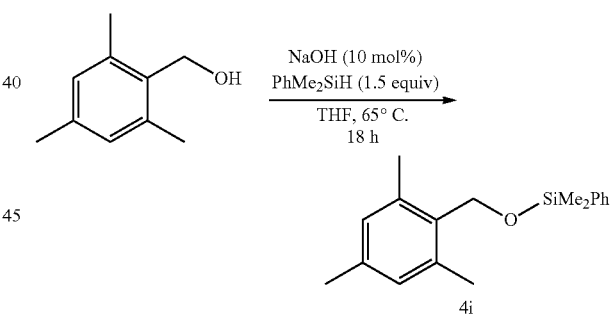

Example 2.2.17. Dimethyl(phenyl)((2,4,6-trimethylbenzyl)oxy)silane 4i: The general procedure was followed. The reaction was performed with NaOH (2.0 mg, 0.05 mmol, 10 mol %), mesitylmethanol (75 mg, 0.5 mmol, 1.0 equiv), PhMe$_2$SiH (102 mg, 115 µL, 0.75 mmol, 1.5 equiv), 0.2 mL dimethylformamide (DMF) and 0.3 mL of tetrahydrofuran (THF) at 65° C. for 18 h. Concentration of the reaction mixture and purification of the resulting residue via Kugelrohr distillation (100 mTorr, 210° C.) gave 118.7 mg (84% yield) of 4i as a colorless oil. (Note: the purified material obtained by Kugelrohr distillation was accompanied by ca. 5% unidentified by-products; however, further purification by chromatography was precluded by the instability of 4i on SiO$_2$ as well as its decomposition under prolonged heating). $^1$H NMR (500 MHz, THF-d8) δ 7.59-7.55 (m, 2H), 7.36-7.30 (m, 3H), 6.79-6.73 (m, 2H), 4.66 (s, 2H), 2.24 (t, J=0.6 Hz, 6H), 2.20 (s, 3H), 0.35 (s, 6H); $^{13}$C NMR (126 MHz, THF-d8) δ 139.02, 137.93, 137.61, 134.72, 134.46, 130.42, 129.65, 128.68, 59.98, 21.23, 19.79, −1.48. IR (Neat Film NaCl) 3421, 3069, 3048, 3008, 2957, 2918, 1614, 1583, 1427, 1373, 1253, 1147, 1118, 1046, 848, 829, 784, 740, 699, 644 cm$^{-1}$; HRMS (EI+) calc'd for C$_{16}$H$_{16}$FSi [(M+H)−H$_2$]: 283.1518, found 283.1526.

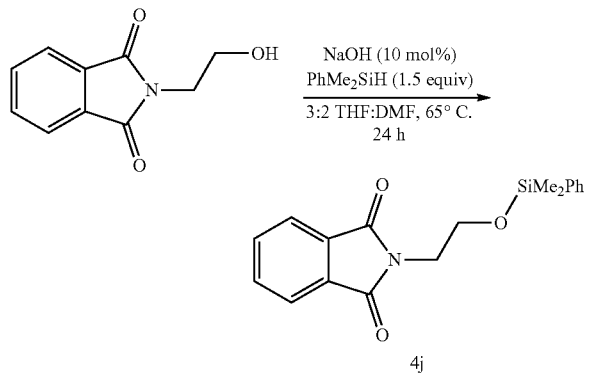

Example 2.2.18. 2-(2-((Dimethyl(phenyl)silyl)oxy)ethyl) isoindoline-1,3-dione 4j: The general procedure was followed. The reaction was performed with NaOH (2.0 mg, 0.05 mmol, 10 mol %), 2-(2-hydroxyethyl)isoindoline-1,3-dione (96 mg, 0.5 mmol, 1.0 equiv), PhMe$_2$SiH (102 mg, 115 μL, 0.75 mmol, 1.5 equiv), 0.2 mL dimethylformamide (DMF) and 0.3 mL of tetrahydrofuran (THF) at 65° C. for 24 h. The desired product 4j (101.6 mg, 62% yield) was obtained as a colorless oil by silica gel flash chromatography (20% EtOAc in hexanes). R$_f$=0.45 (20% EtOAc in hexanes); $^1$HNMR (500 MHz, Benzene-d6) δ 7.52-7.50 (m, 1H), 7.50 (dd, J=2.4, 0.6 Hz, 1H), 7.43 (dd, J=5.4, 3.0 Hz, 2H), 7.16-7.15 (m, 1H), 7.15-7.14 (m, 1H), 7.14 (d, J=2.3 Hz, 1H), 6.87 (ddd, J=5.5, 3.0, 0.5 Hz, 2H), 3.74-3.67 (m, 2H), 3.68-3.62 (m, 2H), 0.26 (s, 6H); $^{13}$C NMR (126 MHz, Benzene-d6) δ 167.96, 137.77, 133.81, 133.39, 132.66, 129.84, 128.13, 122.95, 60.16, 40.23, −1.81. IR (Neat Film NaCl) 2956, 1773, 1713, 1615, 1467, 1427, 1392, 1362, 1319, 1252, 1189, 1116, 1022, 929, 859, 829, 788, 718, 700 cm$^{-1}$; HRMS (EI+) calc'd for C$_{18}$H$_{20}$O$_3$SiN [M+H]: 326.1213, found 326.1223.

Example 2.2.19. Dimethyl(octyloxy)(phenyl)silane 4k: The general procedure was followed. The reaction was performed with NaOH (2.0 mg, 0.05 mmol, 10 mol %), 1-octanol (65 mg, 0.5 mmol, 1.0 equiv), PhMe$_2$SiH (102 mg, 115 μL, 0.75 mmol, 1.5 equiv), and 0.5 mL of tetrahydrofuran (THF) at 25° C. for 18 h. The desired product 4k (111.1 mg, 84% yield) was obtained as a colorless oil by silica gel flash chromatography (100% hexanes). R$_f$=0.49 (100% hexanes); $^1$H NMR (500 MHz, CDCl$_3$) δ 7.64-7.58 (m, 2H), 7.41 (dd, J=5.0, 1.9 Hz, 3H), 3.62 (t, J=6.7 Hz, 2H), 1.60-1.51 (m, 2H), 1.32-1.24 (m, 10H), 0.97-0.85 (m, 3H), 0.41 (s, 6H). This compound has been previously characterized. See Itagaki, S., et al., *Chemistry Letters*, 2013, 42 (9), 980-982

Example 2.2.20. Dimethyl((3-methylcyclohex-2-en-1-yl) oxy)(phenyl)silane 4l: The general procedure was followed. The reaction was performed with NaOH (2.0 mg, 0.05 mmol, 10 mol %), 3-methylcyclohex-2-en-1-ol (56 mg, 0.5 mmol, 1.0 equiv), PhMe$_2$SiH (102 mg, 115 μL, 0.75 mmol, 1.5 equiv), and 0.5 mL of tetrahydrofuran (THF) at 45° C. for 48 h. The desired product 4l (113.4 mg, 92% yield) was obtained as a colorless oil by silica gel flash chromatography (5% EtOAc in hexanes). R$_f$=0.43 (5% EtOAc in hexanes); $^1$H NMR (500 MHz, CDCl$_3$) δ 7.64-7.56 (m, 2H), 7.38 (dd, J=5.0, 1.9 Hz, 3H), 5.34 (dd, J=3.1, 1.6 Hz, 1H), 4.20 (dt, J=5.0, 1.6 Hz, 1H), 1.99-1.69 (m, 4H), 1.64 (tt, J=1.6, 0.9 Hz, 3H), 1.55-1.42 (m, 2H), 0.40 (d, J=1.1 Hz, 6H); $^{13}$C NMR (126 MHz, CDCl$_3$) δ 138.64, 137.78, 133.69, 129.59, 127.89, 125.14, 67.41, 32.13, 30.08, 23.80, 19.83, −0.80, −0.91. IR (Neat Film NaCl) 3423, 3069, 2935, 2862, 1645, 1427, 1251, 1116, 1074, 1024, 992, 894, 880, 828, 786, 738, 700 HRMS (EI+) calc'd for C$_{15}$H$_{21}$OSi [(M+H)−H$_2$]: 245.1362, found 245.1368.

Example 2.2.21. Dimethyl(phenyl)((5-phenylpentyl)oxy) silane 4m: The general procedure was followed. The reaction was performed with NaOH (2.0 mg, 0.05 mmol, 10 mol %), 5-phenylpentan-1-ol (82 mg, 0.5 mmol, 1.0 equiv), PhMe$_2$SiH (102 mg, 115 μL, 0.75 mmol, 1.5 equiv), and 0.5 mL of tetrahydrofuran (THF) at 45° C. for 18 h. The desired product 4m (146.3 mg, 98% yield) was obtained as a colorless oil by silica gel flash chromatography (5% EtOAc in hexanes). R$_f$=0.46 (5% EtOAc in hexanes); $^1$H NMR (500 MHz, CDCl$_3$) δ 7.63 (ddq, J=6.2, 1.9, 0.9 Hz, 2H), 7.46-7.41 (m, 3H), 7.32 (tt, J=7.5, 0.9 Hz, 2H), 7.22 (ddt, J=9.9, 7.3, 1.3 Hz, 3H), 3.65 (td, J=6.7, 1.1 Hz, 2H), 2.67-2.63 (m, 2H), 1.74-1.58 (m, 4H), 1.47-1.38 (m, 2H), 0.44 (t, J=1.0 Hz, 6H); $^{13}$C NMR (126 MHz, CDCl$_3$) δ 142.79, 138.10, 133.58, 129.66, 128.51, 128.34, 127.93, 125.71, 63.15, 36.04, 32.57, 31.41, 25.59, −1.65.IR (Neat Film NaCl) 3385, 3067, 3025, 2933, 2857, 1603, 1495, 1452, 1427, 1341, 1254, 1119, 1055, 831, 791, 726, 698 cm$^{-1}$; HRMS (EI+) calc'd for C$_{19}$H$_{27}$OSi [M+H]: 299.1831, found 299.1840.

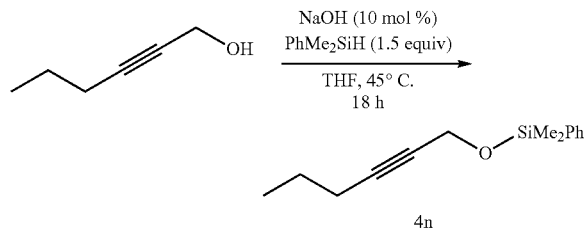

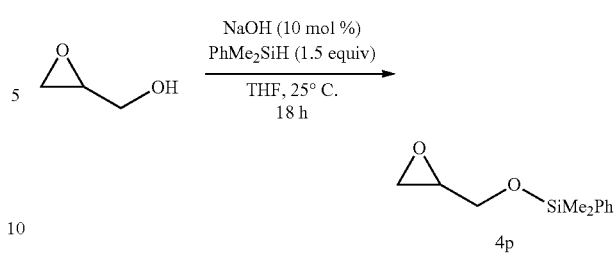

Example 2.2.22. (Hex-2-yn-1-yloxy)dimethyl(phenyl)silane 4n: The general procedure was followed. The reaction was performed with NaOH (2.0 mg, 0.05 mmol, 10 mol %), hex-2-yn-1-ol (49 mg, 0.5 mmol, 1.0 equiv), PhMe$_2$SiH (102 mg, 115 µL, 0.75 mmol, 1.5 equiv), and 0.5 mL of 1 tetrahydrofuran (THF) at 45° C. for 18 h. The desired product 4n (99.9 mg, 86% yield) was obtained as a colorless oil by silica gel flash chromatography (5% EtOAc in hexanes). R$_f$=0.43 (5% EtOAc in hexanes); $^1$HNMR (500 MHz, CDCl$_3$) δ 77.62-7.59 (m, 2H), 7.42-7.36 (m, 3H), 4.27 (t, J=2.2 Hz, 2H), 2.16 (tt, J=7.1, 2.2 Hz, 2H), 1.51 (h, J=7.3 Hz, 2H), 0.97 (t, J=7.3 Hz, 3H), 0.45 (s, 6H); $^{13}$C NMR (126 MHz, CDCl$_3$) δ 137.36, 133.71, 129.84, 127.97, 85.99, 78.37, 51.93, 22.11, 20.92, 13.66, −1.46. Note: this product decomposes slowly in CDCl$_3$. IR (Neat Film NaCl) 3420, 2956, 1646, 1254, 1118, 1067, 1026, 830, 789, 726, 698 cm$^{-1}$; HRMS (EI+) calc'd for C$_{14}$H$_{19}$OSi [M+H]: 231.1205, found 231.1207.

Example 2.2.24. Dimethyl(oxiran-2-ylmethoxy)(phenyl)silane 4p: The general procedure was followed. The reaction was performed with NaOH (2.0 mg, 0.05 mmol, 10 mol %), glycidol (37 mg, 0.5 mmol, 1.0 equiv), PhMe$_2$SiH (102 mg, 115 µL, 0.75 mmol, 1.5 equiv), and 0.5 mL of tetrahydrofuran (THF) at 25° C. for 18 h. The desired product 4p (74.8 mg, 72% yield) was obtained as a colorless oil by silica gel flash chromatography (10% EtOAc in hexanes). R$_f$=0.60 (10% EtOAc in hexanes); $^1$H NMR (500 MHz, Benzene-d6) δ 7.63-7.53 (m, 2H), 7.22 (dd, J=5.5, 1.8 Hz, 3H), 3.58 (dd, J=11.9, 2.9 Hz, 1H), 3.33 (dd, J=11.9, 5.3 Hz, 1H), 2.78 (ddt, J=5.4, 3.9, 2.7 Hz, 1H), 2.24 (dd, J=5.3, 4.0 Hz, 1H), 2.16 (dd, J=5.3, 2.6 Hz, 1H), 0.33 (s, 6H). This compound has been previously characterized. See Bideau, F. L., et al., *Chemical Communications (Cambridge, United Kingdom)*, 2001, 15, 1408-1409

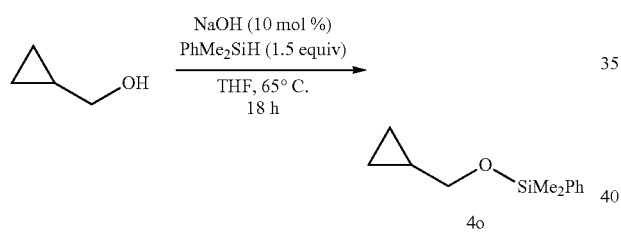

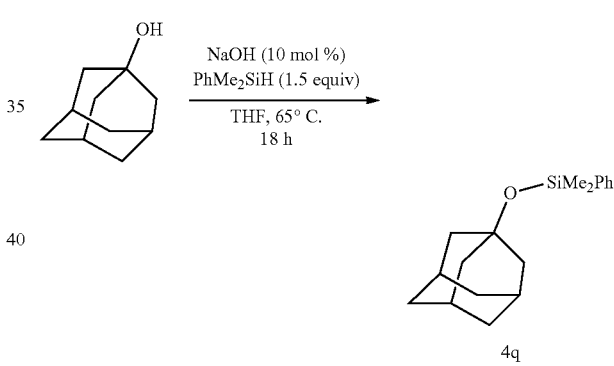

Example 2.2.23. (Cyclopropylmethoxy)dimethyl(phenyl)silane 4o: The general procedure was followed. The reaction was performed with NaOH (2.0 mg, 0.05 mmol, 10 mol %), cyclopropanemethanol (36 mg, 0.5 mmol, 1.0 equiv), PhMe$_2$SiH (102 mg, 115 µL, 0.75 mmol, 1.5 equiv), 0.2 mL dimethylformamide (DMF) and 0.3 mL of tetrahydrofuran (THF) at 65° C. for 18 h. Concentration of the reaction mixture and purification of the resulting residue via Kugelrohr distillation (120 mTorr, 65° C.) gave 65.4 mg (63% yield) of 4o as a colorless oil. Note: product is volatile under high vacuum. (Note: the purified material obtained by Kugelrohr distillation was accompanied by ca. 5% unidentified by-products; however, further purification by chromatography was precluded by the instability of 4o on SiO$_2$). $^1$H NMR (500 MHz, Benzene-d6) δ 7.63-7.58 (m, 2H), 7.27-7.19 (m, 3H), 3.40 (d, J=6.4 Hz, 2H), 0.95 (ttt, J=8.0, 6.4, 4.9 Hz, 1H), 0.34 (s, 6H), 0.32-0.28 (m, 2H), 0.12-0.05 (m, 2H). $^{13}$C NMR (126 MHz, Benzene-d6) δ 138.63, 133.92, 129.80, 128.15, 67.54, 13.68, 3.23, −1.38. IR (Neat Film NaCl) 3070, 3006, 2958, 2862, 1470, 1427, 1403, 1251, 1177, 1116, 1073, 851, 826, 785, 740, 699 cm$^{-1}$; HRMS (EI+) calc'd for C$_{12}$H$_{18}$OSi [M+·]: 206.1127, found 206.1148.

Example 2.2.25. (((3s,5s,7s)-Adamantan-1-yl)oxy)dimethyl(phenyl)silane 4q: The general procedure was followed. The reaction was performed with NaOH (2.0 mg, 0.05 mmol, 10 mol %), 1-adamantol (76 mg, 0.5 mmol, 1.0 equiv), PhMe$_2$SiH (102 mg, 115 µL, 0.75 mmol, 1.5 equiv), and 0.5 mL of tetrahydrofuran (THF) at 65° C. for 18 h. The desired product 4q (66.2 mg, 60% yield) was obtained as a colorless oil by removal of volatiles at 80° C. at 60 mTorr. $^1$H NMR (500 MHz, CDCl$_3$) δ 7.68-7.62 (m, 2H), 7.40-7.38 (m, 3H), 2.13-2.08 (m, 3H), 1.80 (dt, J=3.3, 0.8 Hz, 6H), 1.64-1.55 (m, 6H), 0.43 (s, 6H). This compound has been previously characterized. See Park, J.-W., et al., *Organic Letters*, 2007, vol. 9 (20), 4073-4076.

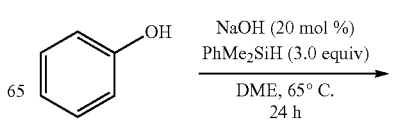

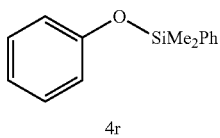

4r

Example 2.2.26. Dimethyl(phenoxy)(phenyl)silane 4r: The general procedure was followed. The reaction was performed with NaOH (2.0 mg, 0.05 mmol, 10 mol %), phenol (47 mg, 0.5 mmol, 1.0 equiv), PhMe$_2$SiH (102 mg, 115 μL, 0.75 mmol, 1.5 equiv), and 0.5 mL of dimethoxyethane (DME) at 65° C. for 24 h. The desired product 4r (101.6 mg, 89% yield) was obtained as a colorless oil by silica gel flash chromatography (5% EtOAc in hexanes). $R_f$=0.42 (5% EtOAc in hexanes); $^1$H NMR (500 MHz, CDCl$_3$) δ 7.75-7.71 (m, 2H), 7.52-7.47 (m, 3H), 7.31-7.24 (m, 2H), 7.05-7.00 (m, 1H), 6.93-6.88 (m, 2H), 0.61 (s, 6H). This compound has been previously characterized. See Horner, L., et al., *Journal of Organometallic Chemistry*, 1985, 282, 155-174.

The same reaction was conducted using NaOH (10 mol %), PhMe$_2$SiH (1.5 equiv) in THF at 45° C. for 48 hours to provide 4r in a yield of 85%

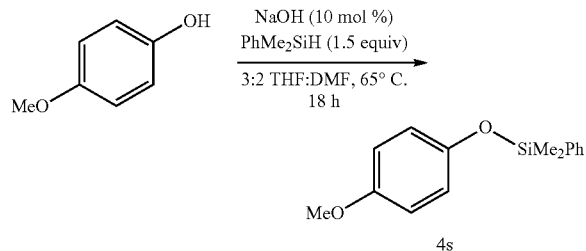

4s

Example 2.2.27. (4-Methoxyphenoxy)dimethyl(phenyl) silane 4s: The general procedure was followed. The reaction was performed with NaOH (2.0 mg, 0.05 mmol, 10 mol %), 4-methoxyphenol (62 mg, 0.5 mmol, 1.0 equiv), PhMe$_2$SiH (102 mg, 115 μL, 0.75 mmol, 1.5 equiv), 0.2 mL dimethylformamide (DMF) and 0.3 mL of tetrahydrofuran (THF) at 65° C. for 18 h. The desired product 4s (106.0 mg, 82% yield) was obtained as a colorless oil by silica gel flash chromatography (5% EtOAc in hexanes). $R_f$=0.45 (5% EtOAc in hexanes); $^1$H NMR (500 MHz, CDCl$_3$) δ 7.63 (dd, J=7.8, 1.7 Hz, 2H), 7.45-7.36 (m, 3H), 6.74 (s, 4H), 3.74 (s, 3H), 0.50 (s, 6H); $^{13}$C NMR (126 MHz, CDCl$_3$) δ 154.32, 148.85, 137.40, 133.61, 130.00, 128.06, 120.73, 114.57, 55.70, -1.11. IR (Neat Film NaCl) 3420, 2958, 2833, 1638, 1505, 1465, 1441, 1427, 1253, 1233, 1118, 1037, 911, 831, 787, 729, 700 cm$^{-1}$; HRMS (EI+) calc'd for C$_{15}$H$_{18}$O$_2$Si [M+·]: 258.1076, found 258.1083.

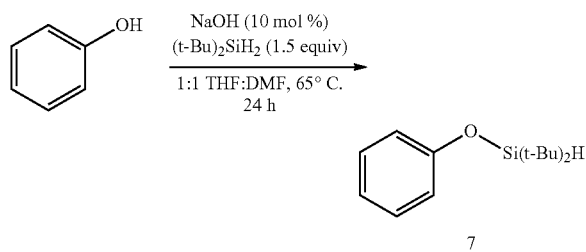

7

Example 2.2.28. Di-tert-butyl(phenoxy)silane 7: The general procedure was followed. The reaction was performed with NaOH (2.0 mg, 0.05 mmol, 10 mol %), phenol (47 mg, 0.5 mmol, 1.0 equiv), (t-Bu)$_2$SiH$_2$ (108 mg, 148 μL, 0.75 mmol, 1.5 equiv), 0.25 mL dimethylformamide (DMF) and 0.25 mL of tetrahydrofuran (THF) at 65° C. for 24 h. The desired product 7 (106.5 mg, 90% yield) was obtained as a colorless oil by silica gel flash chromatography (5% EtOAc in hexanes). $R_f$=0.77 (5% EtOAc in hexanes); $^1$H NMR (500 MHz, CDCl$_3$) δ 7.26-7.21 (m, 3H), 6.95-6.93 (m, 2H), 4.44 (s, 1H), 1.07 (s, 18H). This compound has been previously characterized. See Huang, C., et al., *Journal of the American Chemical Society*, 2011, 133 (32), 12406-12409.

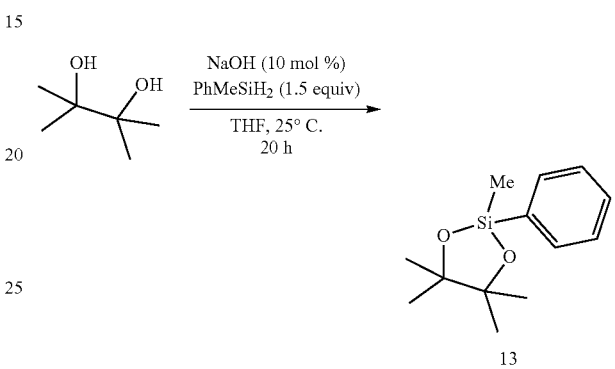

13

Example 2.2.28. 2,4,4,5,5-Pentamethyl-2-phenyl-1,3,2-dioxasilolane 13: The general procedure was followed. The reaction was performed with NaOH (40.0 mg, 1.0 mmol, 10 mol %), pinacol (1.18 g, 10.0 mmol, 1.0 equiv), MePhSiH$_2$ (1.83 g, 2.06 mL, 15.0 mmol, 1.5 equiv), and 10.0 mL of tetrahydrofuran (THF) at 25° C. for 20 h. Concentration of the reaction mixture and purification of the resulting residue via Kugelrohr distillation (150 mTorr, 120° C.) gave 2.19 g (93% yield) of 13 as a colorless oil. Note: product is volatile under high vacuum. $^1$H NMR (500 MHz, Benzene-d6) δ 7.77-7.71 (m, 2H), 7.20-7.17 (m, 3H), 1.22 (s, 6H), 1.16 (s, 6H), 0.43 (s, 3H); $^{13}$C NMR (126 MHz, CDCl$_3$) δ 136.58, 134.03, 130.42, 128.21, 81.80, 26.03, -0.35. IR (Neat Film NaCl) 3441, 3071, 2980, 1643, 1464, 1428, 1366, 1260, 1161, 1121, 1026, 793, 736, 699 cm$^{-1}$; HRMS (EI+) calc'd for C$_{13}$H$_{20}$O$_2$Si [M+·]: 236.1233, found 236.1237.

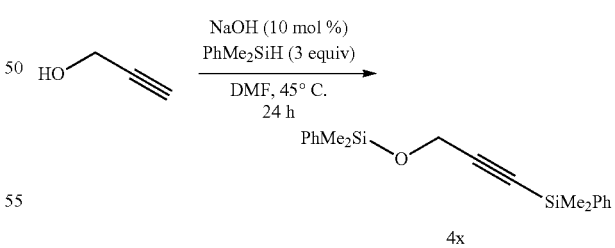

4x

Example 2.2.29. (3-((Dimethyl(phenyl)silyl)oxy)prop-1-yn-1-yl)dimethyl(phenyl)silane 4x: The general procedure was followed. The reaction was performed with NaOH (2.0 mg, 0.05 mmol, 10 mol %), prop-2-yn-1-ol (28 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 45° C. for 24 h. The desired product 4x (142.9 mg, 88% yield) was obtained as a colorless oil after solvent removal at 85° C. at 45 mtorr for 30 minutes. Careful heating is necessary, as the product is volatile under these conditions. $^1$H NMR (500 MHz, CDCl$_3$) δ 7.62 (ddt, J=6.4, 1.8, 0.9 Hz, 4H), 7.44-7.36 (m, 6H), 4.35 (s, 2H), 0.48 (s, 6H), 0.43 (s, 6H); $^{13}$C NMR (126 MHz, CDCl$_3$) δ 137.08, 136.80, 133.82, 133.73, 129.93, 129.57, 128.01, 127.98, 105.77, 88.23, 52.27, −0.93, −1.36. IR (Neat Film NaCl) 3069, 3049, 2959, 2177, 1428, 1363, 1250, 1117, 1085, 1043, 1004, 817, 782, 731, 698 cm$^{-1}$; HRMS (EI+) calc'd for C$_{19}$H$_{23}$OSi$_2$ [(M+H)−H$_2$]: 323.1288, found 323.1297.

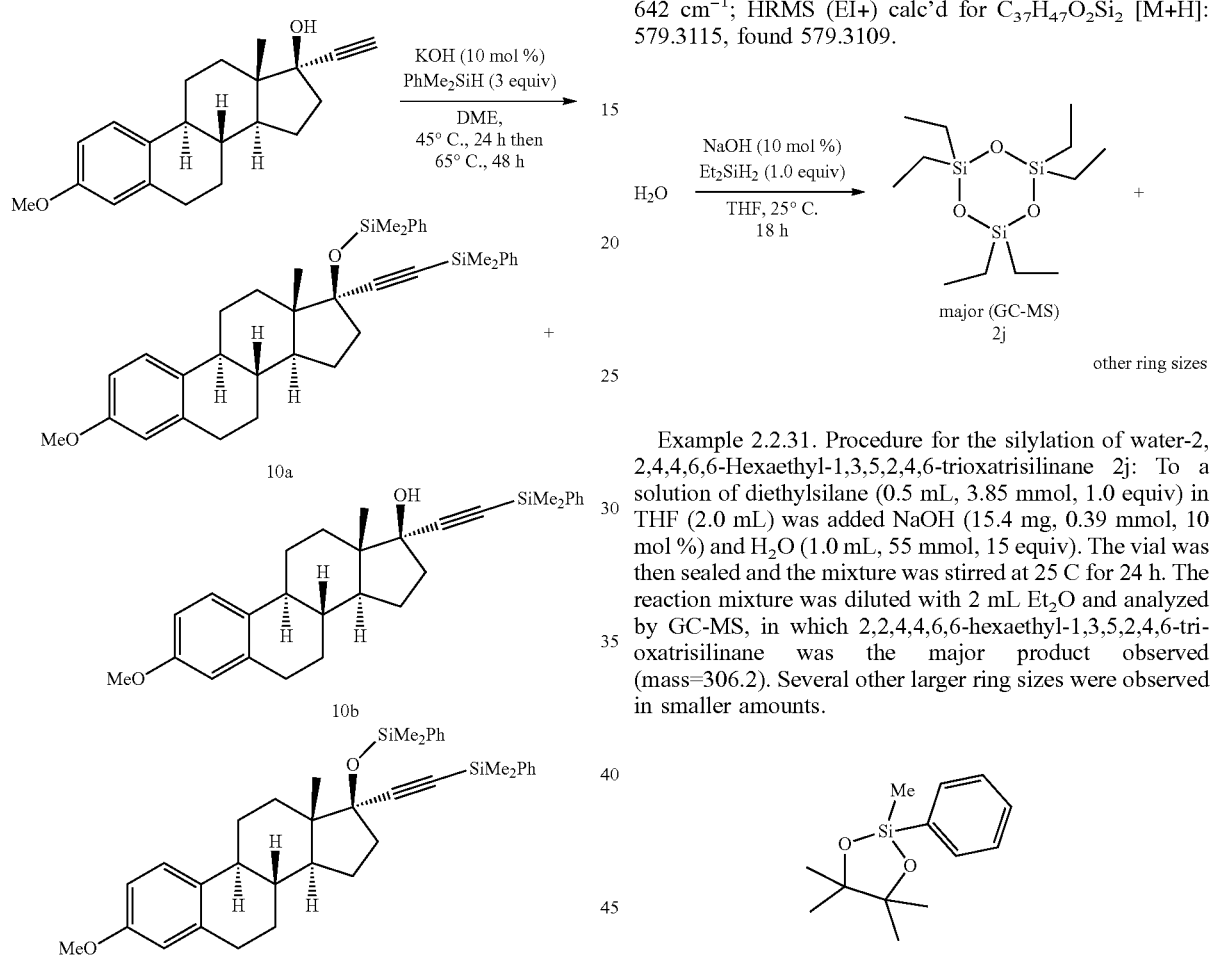

Example 2.2.30. (((8R,9S,13S,14S,17S)-17-((dimethyl (phenyl)silyl)ethynyl)-3-methoxy-13-methyl-7,8,9,11,12,13,14,15,16,17-decahydro-6H-cyclopenta[a]phenanthren-17-yl)oxy)dimethyl (phenyl)silane 10a: The general procedure was followed. The reaction was performed with KOH (2.8 mg, 0.05 mmol, 10 mol %), mestranol ((8R,9S,13S,14S,17R)-17-ethynyl-3-methoxy-13-methyl-7,8,9,11,12,13,14,15,16,17-decahydro-6H-cyclopenta[a]phenanthren-17-ol) (155 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 45° C. for 24 h then 65° C. for 48 h. The product 10a (185.5 mg, 64% yield) was obtained as a colorless oil by silica gel flash chromatography (1%→5% EtOAc in hexanes). $R_f$=0.50 (5% EtOAc in hexanes); $^1$H NMR (500 MHz, THF-d8) δ 7.62-7.56 (m, 4H), 7.30 (dtq, J=9.6, 5.1, 2.2 Hz, 6H), 7.16 (d, J=8.6 Hz, 1H), 6.63 (dd, J=8.5, 2.7 Hz, 1H), 6.59-6.55 (m, 1H), 3.69 (d, J=1.0 Hz, 3H), 2.88-2.75 (m, 2H), 2.42-2.23 (m, 2H), 2.18 (qd, J=10.8, 10.1, 3.5 Hz, 1H), 2.11-1.95 (m, 2H), 1.94-1.85 (m, 1H), 1.83-1.74 (m, 2H), 1.54-1.38 (m, 4H), 1.34 (ddt, J=24.2, 12.3, 5.9 Hz, 1H), 0.94 (d, J=2.0 Hz, 3H), 0.52-0.43 (m, 6H), 0.38-0.32 (m, 6H). $^{13}$C NMR (126 MHz, THF-d8) δ 158.87, 140.78, 138.42, 134.65, 134.38, 133.09, 130.31, 129.98, 128.73, 128.45, 127.12, 114.47, 112.88, 112.37, 90.44, 82.68, 55.34, 51.46, 49.86, 45.16, 41.66, 40.95, 34.17, 30.86, 28.64, 27.69, 24.01, 17.10, 13.81, 1.44, −0.61. IR (Neat Film NaCl) 3417, 3068, 3048, 2946, 2869, 2234, 2160, 2081, 1610, 1575, 1500, 1465, 1427, 1279, 1252, 1136, 1117, 1088, 1045, 929, 886, 818, 783, 730, 699, 642 cm$^{-1}$; HRMS (EI+) calc'd for C$_{37}$H$_{47}$O$_2$Si$_2$ [M+H]: 579.3115, found 579.3109.

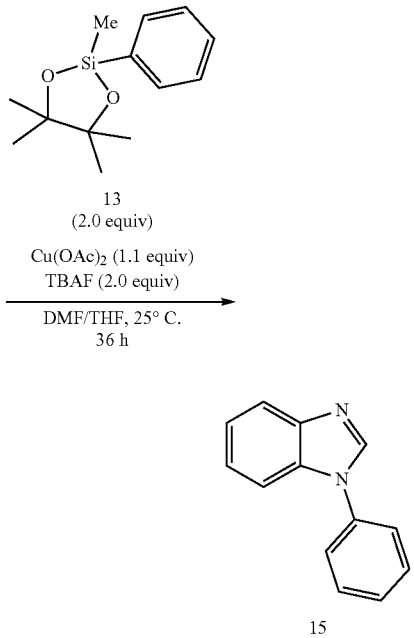

Example 2.2.31. Procedure for the silylation of water-2,2,4,4,6,6-Hexaethyl-1,3,5,2,4,6-trioxatrisilinane 2j: To a solution of diethylsilane (0.5 mL, 3.85 mmol, 1.0 equiv) in THF (2.0 mL) was added NaOH (15.4 mg, 0.39 mmol, 10 mol %) and H$_2$O (1.0 mL, 55 mmol, 15 equiv). The vial was then sealed and the mixture was stirred at 25 C for 24 h. The reaction mixture was diluted with 2 mL Et$_2$O and analyzed by GC-MS, in which 2,2,4,4,6,6-hexaethyl-1,3,5,2,4,6-trioxatrisilinane was the major product observed (mass=306.2). Several other larger ring sizes were observed in smaller amounts.

Example 2.2.32. Procedure for cross-coupling using 2,4,4,5,5-Pentamethyl-2-phenyl-1,3,2-dioxasilolane 13 to form 1-phenyl-1H-benzo[d]imidazole 15: To a mixture of the PhSi$^{Me}$(pin) reagent 13 (freshly prepared, 71.0 mg, 0.3 mmol, 2.0 equiv), benzimidazole 14 (17.6 mg, 0.15 mmol, 1.0 equiv) and Cu(OAc)$_2$ (30.0 mg, 0.165 mmol, 1.1 equiv) in DMF (1.5 mL) was added TBAF (0.3 mL, 1.0M solution in THF) dropwise at 25° C. The mixture was allowed to stir for 36 h at 25° C., after which NaHCO$_3$ saturated solution (2.0 mL) is carefully added and then the mixture was partitioned between EtOAc and hexanes (5.0 mL each). The aqueous layer was extracted with a 1:1 EtOAc:hexanes mixture (2×15 mL) then the combined organic layers were washed with H$_2$O (2×10 mL) and brine (1×10 mL), then dried over MgSO$_4$. The mixture was then filtered, the solvent was removed, and the resulting residue was purified via silica gel flash chromatography (gradient 20% EtOAc in hexanes to 70% EtOAC in hexanes) to yield a colorless solid (21.2 mg, 71% yield). R$_f$=0.25 (20% EtOAc in hexanes); $^1$H NMR (500 MHz, CDCl$_3$) δ 8.16 (s, 1H), 7.93-7.84 (m, 1H), 7.65-7.42 (m, 6H), 7.39-7.31 (m, 2H). This compound has been previously characterized. See Cheng, C., et al., *Science*, 2014, 343, 853-857.

Example 3. Discussion

Example 3.1. Using Benzyl Alcohol

Simple benzyl alcohol was chosen as the model substrate for initial studies along with PhMe$_2$SiH as an inexpensive and abundantly available silicon source (Table 1). The reaction proceeded in THF as the solvent with 10 mol % NaOH as the catalyst to afford 94% yield of the desired benzyl silyl ether 2a at ambient temperature. The reaction could be performed without regard for air and moisture with an identical yield; however some siloxane ((PhMe$_2$Si)$_2$O), arising from hydrolytic oxidation and subsequent coupling of the hydrosilane in the presence of adventitious H$_2$O, was produced as a byproduct.

TABLE 1

NaOH-catalyzed dehydrogenative Si—H/O—H cross coupling: scope of the hydrosilane[a, e]

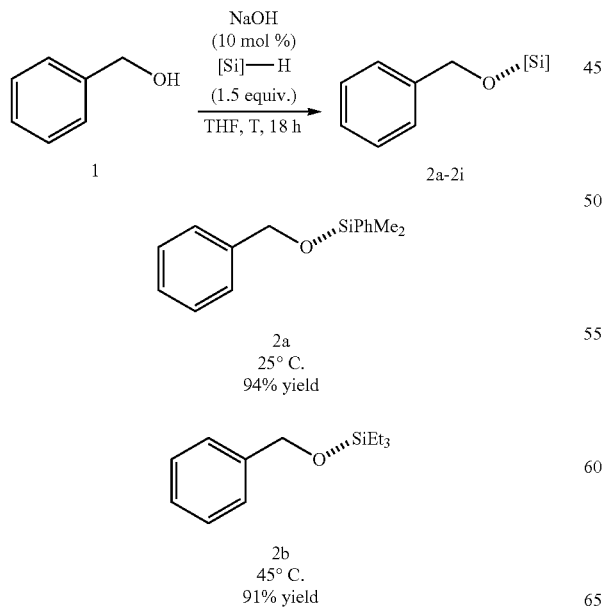

2a
25° C.
94% yield 2b
45° C.
91% yield

TABLE 1-continued

NaOH-catalyzed dehydrogenative Si—H/O—H cross coupling: scope of the hydrosilane[a, e]

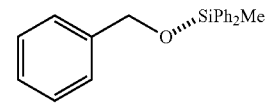

2c
25° C.
82% yield

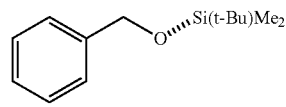

2d
65° C.
60% yield[b, c]

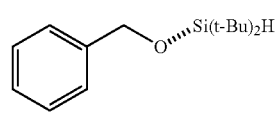

2e
25° C.
96% yield

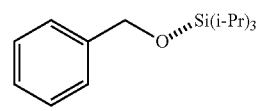

2f
65° C.
85% yield[b]

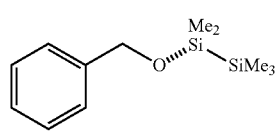

2g
25° C.
67% yield[d]

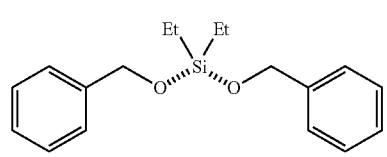

2h
25° C.
80% yield

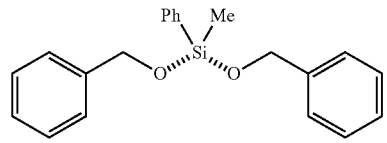

2f
25° C.
95% yield

TABLE 1-continued

NaOH-catalyzed dehydrogenative Si—H/O—H cross coupling: scope of the hydrosilane[a, e]

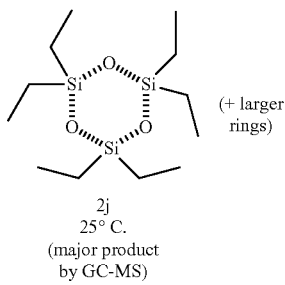

2j
25° C.
(major product by GC-MS)

(+ larger rings)

[a]Reactions performed with 0.5 mmol of starting material and 0.5 mL of THF at the prescribed temperature.
[b]A 1:1 mixture of DMF/THF was used as the solvent.
[c]3.0 equiv. of hydrosilane and 20 mol % NaOH.
[d]The reaction is conducted for 24 h.
[e]Yield of isolated material after purification.

Investigations of a wider scope of the hydrosilane showed that a number of sterically and electronically diverse hydrosilanes were amenable to the disclosed cross-coupling reaction (Table 1, 2a-2g). It was found that the use of DMF as a co-solvent was sometimes necessary to obtain high yields. It is noted here that DMF can also a role in transition metal-catalyzed dehydrogenative Si—O couplings. See Crusciel, J. J. Can. J. Chem. 2005, 83, 508-516. The use of di-tert-butyl silane led to efficient mono-silylation generating 2e in high yield; however, the use of less sterically hindered dihydrosilanes led to Si-tethered species 2h and 2i at ambient temperature. Remarkably, the cross-dehydrogenative O—Si coupling tolerated sensitive disilanes such as H—$Si_2(CH_3)_5$ leading to product 2g. In certain embodiments, then, the disclosed methods are also useful for appending polysilanes onto small molecules and hydroxy-containing surfaces of for example polymers (e.g., polyvinyl alcohol) and/or hydrated inorganic oxides (e.g., hydrated silica, alumina, etc., including surfaces comprising these hydrated oxides), which is especially valuable given the importance of Si—Si oligomers and polymers in materials science applications, as described in Fujiki, M. *Polymer Journal* 2003, 35, 297-344. Additionally, the reaction of diethylsilane with water under NaOH catalysis resulted in the formation of cyclic siloxanes, with the trisiloxane 2j being the major product by GC-MS analysis. These products are precursors to valuable polysiloxanes, as described for example in Hunter, M. J., et al., *J. Am. Chem. Soc.*, 1946, 68, 667-672

Example 2.2. Extending Alcohol Scope

Table 2 provides a sampling of the wide variety of hydroxyl-containing small molecules useful in the present methods. The disclosed cross-dehydrogenative coupling was amenable to substrates containing aromatic (Table 2, entries 1-11, 19, and 20) as well as aliphatic (entries 12, 15, and 17-20) moieties. The reaction proceeded well in the presence of arenes bearing halides (Table 1, entries 2 and 3), nitro- (entry 4), ether (entry 6), and alkyl (entry 10) functionalities leading to the corresponding silyl ethers in generally high yields. Molecules containing electron poor- (entry 7) and electron rich aromatic heterocycles (entries 8 and 9) were likewise excellent substrates for the dehydrocoupling. A secondary allylic alcohol (entry 13) and an internal alkyne (entry 15) also reacted well, with no reduction or hydrosilylation of the C—C multiple bonds detected. Strained rings (entries 16, and 17) were likewise tolerated with no undesired ring opening observed. Even the tertiary alcohol 1-adamantol (entry 18) was responsive to the dehydrocoupling yielding the silyl ether in excellent yield. The disclosed silylation methods were also amenable to the silylation of phenols, generating the corresponding silylated products in good yields (entries 19 and 20), though under somewhat more demanding reaction conditions.

Moreover, the functionalities such as an aromatic methyl ester (entry 5) and a phthalimide (entry 11), which are known to readily undergo hydrosilylation or direct reduction in the presence of Lewis bases and hydrosilanes, remain intact under these reaction conditions giving 4e and 4k respectively with no undesired hydrosilylation or reduction detected. This further demonstrated that the disclosed O—Si cross-dehydrocoupling is complementary to alternative methods in terms of scope and practicality and is evidence of the method's mild conditions and broad tolerance of sensitive functionalities.

TABLE 2

Scope of the alcohol partner[a, d, e]

| Entry | Silylated Product | T (° C) | Yield |
|---|---|---|---|
| 1 | [Si], R = H | 25 | 2a (94%) |
| 2 | R = 4-F | 25 | 4a (79%) |
| 3 | R = 4-Br | 65 | 4b (91%) |
| 4 | R = 4-$NO_2$ | 65 | 4c (71%) |
| 5 | R = 4-$CO_2Me$ | 65 | 4d (84%)[b] |
| 6 | R = 4-OMe | 25 | 4e (87%) |
| 7 | (pyridyl-CH2-O-[Si]) | 25 | 4f (97%) |
| 8 | (thienyl-CH2-O-[Si]) | 25 | 4g (96%) |
| 9 | (furyl-CH2-O-[Si]) | 45 | 4h (87%) |
| 10 | (2,4,6-trimethylbenzyl-O-[Si]) | 65 | 4i (92%)[b] |
| 11 | (phthalimido-CH2CH2-O-[Si]) | 65 | 4j (62%) |
| 12 | (alkyl-O-[Si], n = 5) | 25 | 4k (84%) |

TABLE 2-continued

Scope of the alcohol partner[a, d, e]

| Entry | Silylated Product | T (°C) | Yield |
|---|---|---|---|
| 13 | (cyclohexenyl-Me with O-[Si]) | 45 | 4l (92%)[b] |
| 14 | (phenyl-(CH2)n=4-O[Si]) | 45 | 4m (98%) |
| 15 | (pentynyl-CH2-O[Si]) | 45 | 4n (86%) |
| 16 | (cyclopropyl-CH2-O[Si]) | 65 | 4o (70%) |
| 17 | (glycidyl-O[Si]) | 25 | 4p (72%) |
| 18 | (1-adamantyl-O[Si]) | 65 | 4q (96%) |
| 19 | (PhO-[Si]) | 65 | 4r (89%)[c] |
| 20 | (4-MeO-C6H4-O[Si]) | 65 | 4s (82%) |

[a] Reactions performed with 0.5 mmol of starting material and 0.5 mL of THF at the prescribed temperature.
[b] 2:3 DMF/THF used as the solvent.
[c] 3.0 equiv. hydrosilane, 20 mol % NaOH, DME [1.0M] solvent.
[d] [Si] = PhMe$_2$SiH.
[e] Yield of isolated material after purification.
[f] Base-catalyzed transesterification by the pendant alcohol occurred with this substrate, resulting in a separable mixture containing approximately a 1:5 ratio of silylated dimer:silylated monomer; the combined silylated yield was 84%.

Example 3. Introduction of Silyl Ethers as Directing Groups

The disclosed cross-dehydrogenative silylation also proved to be a convenient one-step installation of directing groups of value in organic synthesis (Table 3).

TABLE 3

Applications to directing group chemistry[a, b]

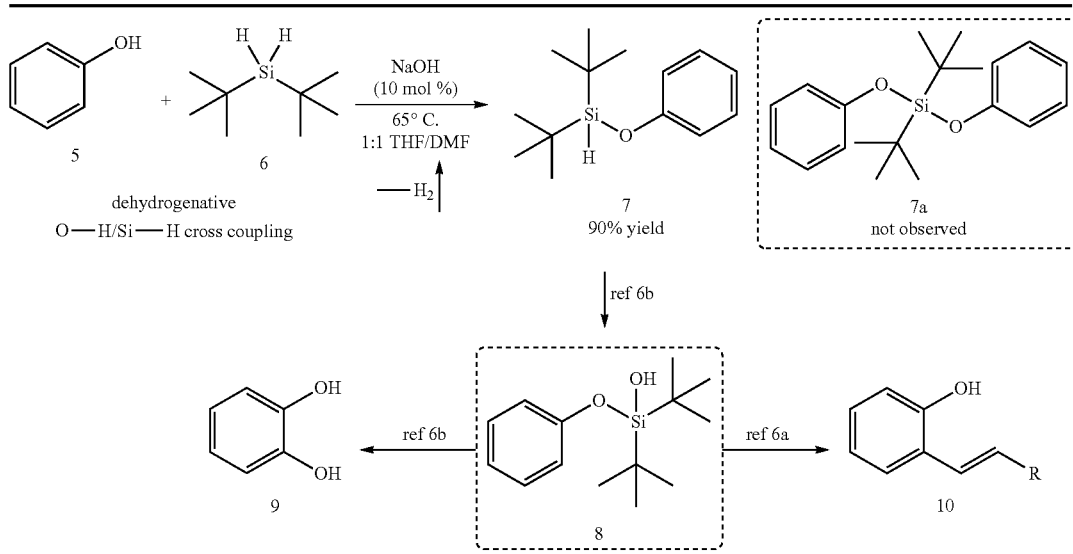

[a] Reaction performed with 0.5 mmol of starting material and 0.5 mL of THF.
[b] Yield of isolated material after purification.
Ref 6a refers to the methods described in Huang, C., et al., *J. Am. Chem. Soc.* 2011, 133, 12406-12409; Ref 6b refers to the methods described in Huang, C., et al., *J. Am. Chem. Soc.* 2011, 133, 17630-17633, both of which are incorporated by reference for their teachings of these methods.

For example, the reaction of phenol 5 with the bulky and commercially available di-tert-butylsilane 6 with 10 mol % NaOH furnished the corresponding di-tert-buylhydrosilyl ether 7 in high yield and without undesirable double activation of the Si—H bond, which would have otherwise led to the formation of 7a (Table 3). Silane 7 was readily advanced to silanol 8, which contains a directing group for palladium-catalyzed C—H functionalization reactions such as ortho-oxidation to generate catechols (Table 3, 8→9) and ortho-alkenylation to access α-hydroxy styrenes (8→10).

Cognizant of the importance of heteroatom-substituted arylsilanes in C—C and C—X bond-forming reactions, the catalytic Si—O bond construction method was tested for the expedient and cost-efficient synthesis of novel cross-coupling reagents. Toward this aim, the silicon analogue of PhB(pin)-Ph$^{Me}$Si(pin) (Table 4, 13) where Me is chosen as a non-transferrable group—was prepared and evaluated for its suitability as an aryl transfer reagent. This would be beneficial given the increased abundance and lower cost of Si relative to B, and the potential for improved stability or overall utility of the silicon reagent. However, these efforts faced the potential challenges of a one-step preparation of the proposed silicon-based aryl transfer reagent involving a silylene protection of a 1,2-diol, which is challenging, even in the case of simple, non-sterically hindered diols. Poor cyclization reactivity, uncontrollable oligomerization, or rearrangements, all of which are known to occur. Prior to the present efforts, this compound has only been prepared by two strategies: refluxing pinacol in THF for 24 h with a) the dichlorosilane in the presence of stoichiometric pyridine, or b) the dihydrosilane in the presence of a catalytic quantity of Cp$_2$TiCl$_2$/n-BuLi. The yields were 20-50% and 67% respectively and the product was not fully characterized. The success of the efforts described herein, based on the mild catalyst system disclosed herein provide a convenient route toward these interesting dioxasilacycles and their derivatives.

Thus, combining the commercially available and inexpensive SiPhMeSiH$_2$ 11 with the di-tertiary 1,2-diol pinacol 12 in a 1:1 stoichiometry at ambient temperature resulted in the immediate and vigorous evolution of hydrogen upon addition of NaOH (10 mol %).

TABLE 4

Multi-gram scale catalytic synthesis of PhSiMe(pin) and discovery of an aryl transfer reagent[a, b, c]

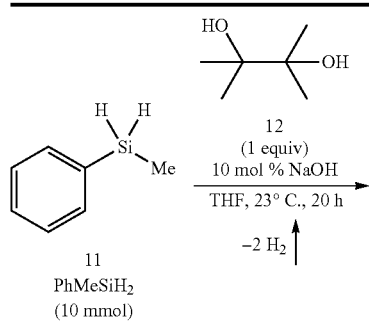

TABLE 4-continued

Multi-gram scale catalytic synthesis of PhSiMe(pin) and discovery of an aryl transfer reagent[a, b, c]

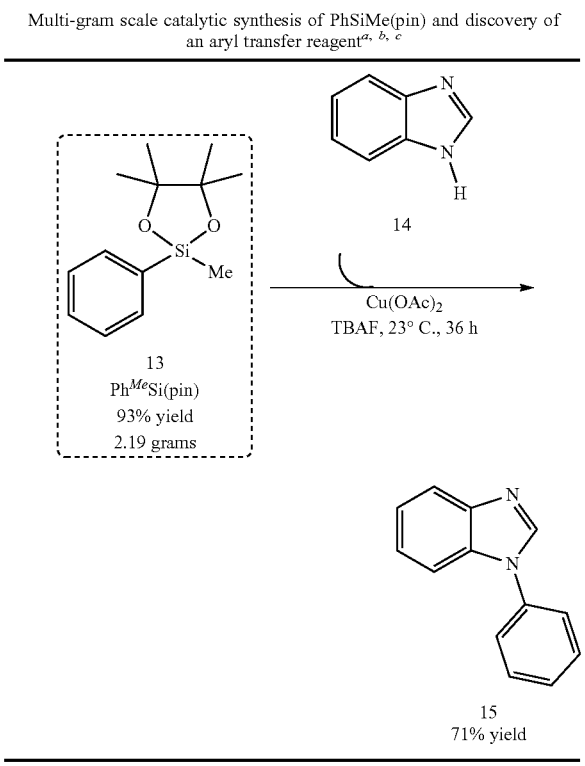

[a]Reactions performed with 0.5 mmol of starting material and 0.5 mL of THF at the prescribed temperature.
[b]Cu-mediated reaction performed on 0.5 mmol scale.
[c]Yield of isolated material after purification.

Surprisingly, the reaction was complete in 20 hours, giving a high yield (2.19 grams, 93% yield) of the corresponding colourless, distillable oil PhSi$^{Me}$(pin) 13 (Scheme 3, 11→13). No oligomers, polymers, or uncyclized products were detected. With this compound in hand, its ability to transfer the phenyl moiety bound to silicon in a Hiyama-type cross-coupling reaction could finally be investigated. To test this, the PhSi$^{Me}$(pin) reagent was treated with benzimidazole 14, Cu(OAc)$_2$, and TBAF and the mixture was stirred at ambient temperature for 36 h to provide the desired N-arylation product 15 in 71% yield. Comparing these results with the 74% yield reported in C. Cheng and J. F. Hartwig, Science, 343 (6173), 853-857 (2014) using 1,2-dimethyl-4-(1-methyl-2-trimethylsilanyl-1-trimethylsilanyloxy-ethyl)-benzene under comparable conditions demonstrates the ability of these pinacol (and related) derivatives to react in a similar fashion with Cheng's R—SiMe(OTMS)$_2$ derivatives, including for example cross coupling with aryl halides to form biaromatics, addition of silylarenes to acrylates, and amination of benzimidizoles. The ability to provide a convenient and high-yielding catalytic silylene protection of pinacol is demonstrated, generating Ph$^{Me}$Si(pin) in a single step from commercially available materials, provides an intriguing complement to boron-based cross-coupling reagents.

As those skilled in the art will appreciate, numerous modifications and variations of the present invention are possible in light of these teachings, and all such are contemplated hereby. All references cited within this disclosure are incorporated by reference herein for all purposes, or at least for their teachings in the context presented.

What is claimed:

1. A composition comprising (a) at least one hydrosilane; (b) sodium hydroxide and/or potassium hydroxide; (c) an organic substrate having at least one organic alcohol moiety; (d) an aprotic polar solvent; and (e) a silyl ether derived or derivable from the dehydrogenative coupling of the at least one hydrosilane and the at least one alcohol moiety, the composition being substantially devoid of crown ether, transition metal ions or complexes, alkoxides, hydrides, alkyl lithium reagents, or fluoride ion;
wherein the hydrosilane has a structure of Formula (I) or of Formula (II):

$(R)_{3-m}Si(H)_{m+1}$ (I)

$(R)_{2-m}(H)_{m+1}Si-Si(R)_{3-m}(H)_m$ (II)

where: m is independently 0, 1, or 2; and each R is independently optionally substituted $C_{1-24}$ alkyl or heteroalkyl, optionally substituted $C_{2-24}$ alkenyl or heteroalkenyl, optionally substituted $C_{2-24}$ alkynyl or heteroalkynyl, optionally substituted 6 to 18 ring membered aryl or 5 to 18 ring membered heteroaryl, optionally substituted 6 to 18 ring-membered alkaryl or 5 to 18 ring-membered heteroalkaryl, optionally substituted 6 to 18 ring-membered aralkyl or 5 to 18 ring-membered heteroaralkyl, optionally substituted —O—$C_{1-24}$ alkyl or heteroalkyl, optionally substituted 6 to 18 ring-membered aryloxy or 5 to 18 ring-membered heteroaryloxy, optionally substituted 6 to 18 ring-membered alkaryloxy or 5 to 18 ring-membered heteroalkaryloxy, or optionally substituted 6 to 18 ring-membered aralkoxy or 5 to 18 ring-membered heteroaralkoxy, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, 5 to 12 ring-membered arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, siloxazanyl, boronato, boryl, or halogen, where the substituents may optionally provide a tether to an insoluble or sparingly soluble support media comprising alumina, silica, or carbon.

2. The composition of claim 1, wherein the aprotic polar solvent is present as an aprotic oxygen donor solvent, the composition containing less than 500 ppm water.

3. The composition of claim 1, wherein the aprotic polar solvent comprises acetonitrile, dimethylacetamide, dimethyl formamide, dimethyl sulfoxide, dimethoxyethane (DME), an optionally substituted dioxane, a dialkyl ether, hexamethylphosphoramide (HMPA), an optionally substituted THF, a furan, or N-methyl pyrrolidone (NMP).

4. The composition of claim 1, wherein the hydrosilane has a structure of Formula (I) or of Formula (II):

$(R)_{3-m}Si(H)_{m+1}$ (I)

$(R)_{2-m}(H)_{m+1}Si-Si(R)_{3-m}(H)_m$ (II)

where: m is independently 0, 1, or 2; and each R is independently optionally substituted $C_{1-24}$ alkyl or heteroalkyl, optionally substituted $C_{2-24}$ alkenyl or heteroalkenyl, optionally substituted $C_{2-24}$ alkynyl or heteroalkynyl, optionally substituted 6 to 18 ring membered aryl or 5 to 18 ring membered heteroaryl, optionally substituted 6 to 18 ring-membered alkaryl or 5 to 18 ring-membered heteroalkaryl, optionally substituted 6 to 18 ring-membered aralkyl or 5 to 18 ring-membered heteroaralkyl, and, if substituted, the substituents are independently phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, 5 to 12 ring-membered arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, siloxazanyl, boronato, boryl, or halogen, where the substituents may optionally provide a tether to an insoluble or sparingly soluble support media comprising alumina, silica, or carbon.

5. The composition of claim 1, wherein the hydrosilane is $(R)_3SiH$, $(R)_2SiH_2$, or $(R)SiH_3$, where R is independently $C_{1-6}$alkyl, $C_{2-6}$alkenyl, $C_{6-24}$aryl, a 5- or 6-ring membered heteroaryl, aralkyl, or heteroaralkyl compound or moiety.

6. The composition of claim 1 comprising the sodium hydroxide (NaOH).

7. The composition of claim 1 comprising the potassium hydroxide (KOH).

8. The composition of claim 4, wherein the hydrosilane is a hydrosilane of Formula (I), where m is 1 or 2.

9. The composition of claim 4, wherein the hydrosilane is a hydrosilane of Formula (I), where m is 1, and R is an optionally substituted tertiary $C_{1-12}$ alkyl group.

10. The composition of claim 1, wherein the hydrosilane is $EtMe_2SiH$, $Et_3SiH$, $(n-Bu)_3SiH$, $(i-Pr)_3SiH$, $Et_2SiH_2$, $Ph_2MeSiH$, $(t-Bu)Me_2SiH$, $(t-Bu)_2SiH_2$, $PhMeSiH_2$, $PhMe_2SiH$, $BnMe_2SiH$, $(EtO)_3SiH$, $Me_2(pyridinyl)SiH$, $(i-Pr)_2(pyridinyl)SiH$, $Me_3Si-SiMe_2H$.

11. The composition of claim 1, wherein the organic substrate having at least one organic alcohol moiety has a structure of Formula (IIIA):

$R^1-OH$ (IIIA), where $R^1$ comprises an optionally substituted $C_{1-24}$ alkyl, optionally substituted $C_{2-24}$ alkenyl, optionally substituted $C_{2-24}$ alkynyl, optionally substituted $C_{6-24}$ aryl, optionally substituted $C_{1-24}$ heteroalkyl, optionally substituted 5- or 6-ring membered heteroaryl, optionally substituted $C_{7-24}$ aralkyl, optionally substituted heteroaralkyl, or optionally substituted metallocene.

12. The composition of claim 1, wherein the organic substrate having at least one organic alcohol moiety has a structure of Formula (IIIB):

$HO-R^2-OH$ (IIIB), where $R^2$ comprises an optionally substituted $C_{2-12}$ alkylene, optionally substituted $C_{2-12}$ alkenylene, optionally substituted $C_{6-24}$ arylene, optionally substituted $C_{1-12}$ heteroalkylene, or an optionally substituted 5- or 6-ring membered heteroarylene.

13. The composition of claim 1, wherein the organic substrate having at least one organic alcohol moiety comprises an optionally substituted catechol moiety or has a Formula (IV):

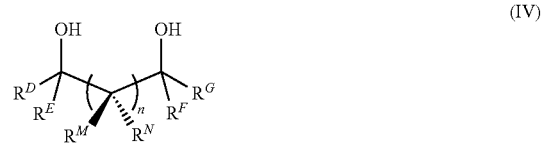

(IV)

wherein n is from 0 to 6;

$R^M$ and $R^N$ are independently H or methyl $R^D$, $R^E$, $R^F$, and $R^G$ are independently H, $C_{1-6}$ alkyl, optionally substituted phenyl, optionally substituted benzyl, optionally substituted 5- or 6-ring membered heteroaryl, wherein the optional substituents are $C_{1-3}$ alkyl, $C_{1-3}$ alkoxy, or halo.

14. The composition of claim 1, wherein the organic substrate having at least one organic alcohol moiety is polymeric.

15. The composition of claim 1, wherein the at least one organic alcohol moiety comprises an aliphatic alcohol moiety.

16. The composition of claim 1, wherein the at least one organic alcohol moiety comprises an aromatic or α-methyl aromatic alcohol moiety.

17. The composition of claim 1, wherein the at least one organic alcohol moiety comprises an optionally substituted benzylic alcohol moiety.

18. The composition of claim 1, wherein at least one organic alcohol moiety is an optionally substituted phenol and the at least one hydrosilane is (tert-butyl)$_2$Si(H)$_2$, the silyl ether comprises a di-tert-butyl silyl phenyl ether.

19. The composition of claim 18, wherein the substituted phenol has a structure of Formula (V), and the di-tert-butyl silyl phenyl ether has a structure of Formula (VI), where n is 0, 1, 2, 3, 4, or 5, and $R^A$ is optionally at least one of aldehyde (—CHO), $C_{1-6}$ alkyl, $C_{1-6}$ alkylcarbonyl (—C(O)—$C_{1-6}$alkyl), $C_{1-6}$ alkoxy, $C_{1-6}$ alkoxycarbonyl (—C(O)—$C_{1-6}$alkyl), —C(O)—$C_{6-24}$ aryl), —C(O)—(5- or 6 membered heteroaryl), halo, nitrile, or nitro

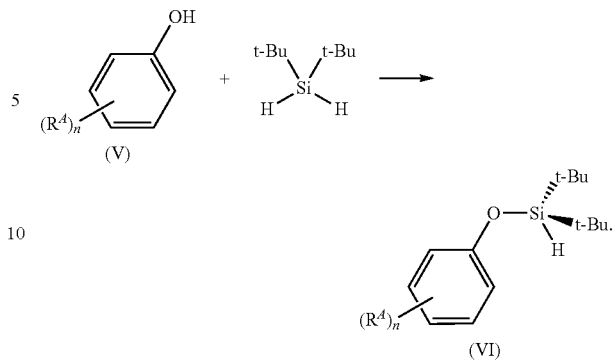

20. The composition of claim 1, wherein the hydrosilane has a structure of Formula (I) or of Formula (II):

$$(R)_{3-m}Si(H)_{m+1} \quad (I)$$

$$(R)_{2-m}(H)_{m+1}Si—Si(R)_{3-m}(H)_m \quad (II)$$

where: m is independently 0, 1, or 2; and each R is independently an unsubstituted $C_{1-24}$ alkyl or heteroalkyl, an unsubstituted $C_{2-24}$ alkenyl or heteroalkenyl, an unsubstituted $C_{2-24}$ alkynyl or heteroalkynyl, an unsubstituted 6 to 18 ring membered aryl or 5 to 18 ring membered heteroaryl, an unsubstituted 6 to 18 ring-membered alkaryl or 5 to 18 ring-membered heteroalkaryl, or an unsubstituted 6 to 18 ring-membered aralkyl or 5 to 18 ring-membered heteroaralkyl.

21. The composition of claim 20, further comprising the silyl ether derived or derivable from the dehydrogenative coupling of the at least one hydrosilane and the at least one alcohol moiety.

* * * * *